US012740830B2

(12) United States Patent
Hlad et al.

(10) Patent No.: US 12,740,830 B2
(45) Date of Patent: Sep. 22, 2026

(54) PATIENT-SPECIFIC SOFT TISSUE REARRANGEMENT

(71) Applicant: Treace Medical Concepts, Inc., Ponte Vedra, FL (US)

(72) Inventors: Lee M. Hlad, Waycross, GA (US); James Q. Spitler, Winter Garden, FL (US)

(73) Assignee: Treace Medical Concepts, Inc., Ponte Vedra, FL (US)

( * ) Notice: Subject to any disclaimer, the term of this patent is extended or adjusted under 35 U.S.C. 154(b) by 198 days.

(21) Appl. No.: 18/373,131

(22) Filed: Sep. 26, 2023

(65) Prior Publication Data

US 2024/0099778 A1 Mar. 28, 2024

Related U.S. Application Data

(60) Provisional application No. 63/410,599, filed on Sep. 27, 2022.

(51) Int. Cl.
*A61B 34/10* (2016.01)
*A61B 17/17* (2006.01)
(Continued)

(52) U.S. Cl.
CPC .......... *A61B 34/10* (2016.02); *A61B 17/1796* (2013.01); *A61F 2/0811* (2013.01); *A61B 2017/00526* (2013.01); *A61B 2017/565* (2013.01); *A61B 2017/568* (2013.01); *A61B 2034/105* (2016.02); *A61B 2034/107* (2016.02);
(Continued)

(58) Field of Classification Search
CPC ..................................................... A61B 34/10
See application file for complete search history.

(56) References Cited

U.S. PATENT DOCUMENTS 3,664,022 A 5/1972 Small
4,069,824 A 1/1978 Weinstock
(Continued)

FOREIGN PATENT DOCUMENTS

AU 2009227957 B2 7/2014
AU 2009222469 B2 2/2015
(Continued)

OTHER PUBLICATIONS

"Foot and Ankle Instrument Set," Smith & Nephew, 2013, 2 pages.
(Continued)

*Primary Examiner* — Christian A Sevilla
(74) *Attorney, Agent, or Firm* — Fredrikson & Byron, P.A.

(57) ABSTRACT

An apparatus, system, and method are disclosed for remediating a condition present in a patient. In some implementations, the apparatus may include a body and a trajectory port that extends through the body. The trajectory port guides a tool to form a bone tunnel in a bone of a patient. The trajectory port is defined at least partially on a bone model of at least a portion of bone of the patient. The apparatus may include a bone engagement feature that extends from the body, the bone engagement feature configured to engage at least a portion of the bone such that the bone engagement feature positions the bone tunnel guide in a position that corresponds to a modeled position of a bone tunnel guide model engaging a bone model.

20 Claims, 20 Drawing Sheets

(51) Int. Cl.
*A61F 2/08* (2006.01)
*A61B 17/00* (2006.01)
*A61B 17/56* (2006.01)

(52) U.S. Cl.
CPC . *A61B 2034/108* (2016.02); *A61F 2002/0852* (2013.01); *A61F 2002/0882* (2013.01)

(56) References Cited

U.S. PATENT DOCUMENTS 4,159,716 A 7/1979 Borchers
4,187,840 A 2/1980 Watanabe
4,335,715 A 6/1982 Kirkley
4,338,927 A 7/1982 Volkov et al.
4,349,018 A 9/1982 Chambers
4,409,973 A 10/1983 Neufeld
4,436,684 A 3/1984 White
4,440,168 A 4/1984 Warren
4,509,511 A 4/1985 Neufeld
4,565,191 A 1/1986 Slocum
4,570,624 A 2/1986 Wu
4,628,919 A 12/1986 Clyburn
4,736,737 A 4/1988 Fargie et al.
4,750,481 A 6/1988 Reese
4,754,746 A 7/1988 Cox
4,757,810 A 7/1988 Reese
4,839,822 A 6/1989 Dormond et al.
4,895,141 A 1/1990 Koeneman et al.
4,959,066 A 9/1990 Dunn et al.
4,978,347 A 12/1990 Ilizarov
4,988,349 A 1/1991 Pennig
4,995,875 A 2/1991 Coes
5,049,149 A 9/1991 Schmidt
5,053,039 A 10/1991 Hofmann et al.
5,112,334 A 5/1992 Alchermes et al.
5,147,364 A 9/1992 Comparetto
5,171,244 A 12/1992 Caspari et al.
5,176,685 A 1/1993 Rayhack
5,207,676 A 5/1993 Canadell et al.
5,254,119 A 10/1993 Schreiber
5,312,412 A 5/1994 Whipple
5,358,504 A 10/1994 Paley et al.
5,364,402 A 11/1994 Mumme et al.
5,374,271 A 12/1994 Hwang
5,405,354 A * 4/1995 Sarrett ............... A61B 17/0469 223/102
5,417,694 A 5/1995 Marik et al.
5,449,360 A 9/1995 Schreiber
5,470,335 A 11/1995 Du Toit
5,490,854 A 2/1996 Fisher et al.
5,529,075 A 6/1996 Clark
5,540,695 A 7/1996 Levy
5,578,038 A 11/1996 Slocum
5,586,564 A 12/1996 Barrett et al.
5,601,565 A 2/1997 Huebner
5,613,969 A 3/1997 Jenkins, Jr.
5,620,442 A 4/1997 Bailey et al.
5,643,270 A 7/1997 Combs
5,662,656 A 9/1997 White
5,667,510 A 9/1997 Combs
H1706 H 1/1998 Mason
5,722,978 A 3/1998 Jenkins, Jr.
5,749,875 A 5/1998 Puddu
5,779,709 A 7/1998 Harris, Jr. et al.
5,788,695 A 8/1998 Richardson
5,803,924 A 9/1998 Oni et al.
5,810,822 A 9/1998 Mortier
5,836,950 A 11/1998 Hansson
5,839,438 A 11/1998 Graettinger et al.
5,843,085 A 12/1998 Graser
5,893,553 A 4/1999 Pinkous
5,911,724 A 6/1999 Wehrli
5,935,128 A 8/1999 Carter et al.
5,941,877 A 8/1999 Viegas et al.
5,951,556 A 9/1999 Faccioli et al.
5,957,927 A 9/1999 Magee et al.
5,980,526 A 11/1999 Johnson et al.
5,984,931 A 11/1999 Greenfield
6,007,535 A 12/1999 Rayhack et al.
6,030,391 A 2/2000 Brainard et al.
6,162,223 A 12/2000 Orsak et al.
6,171,309 B1 1/2001 Huebner
6,203,545 B1 3/2001 Stoffella
6,248,109 B1 6/2001 Stoffella
6,391,031 B1 5/2002 Toomey
6,416,465 B2 7/2002 Brau
6,478,799 B1 11/2002 Williamson
6,511,481 B2 1/2003 Von Hoffmann et al.
6,676,662 B1 1/2004 Bagga et al.
6,712,824 B2 3/2004 Millard et al.
6,719,773 B1 4/2004 Boucher et al.
6,743,233 B1 6/2004 Baldwin et al.
6,755,838 B2 6/2004 Trnka
6,780,190 B2 8/2004 Maroney
6,796,986 B2 9/2004 Duffner
6,859,661 B2 2/2005 Tuke
6,944,518 B2 9/2005 Roose
6,964,645 B1 11/2005 Smits
7,033,361 B2 4/2006 Collazo
7,097,647 B2 8/2006 Segler
7,153,310 B2 12/2006 Ralph et al.
7,182,766 B1 2/2007 Mogul
7,241,298 B2 7/2007 Nemec et al.
7,282,054 B2 10/2007 Steffensmeier et al.
7,351,203 B2 4/2008 Jelliffe et al.
7,377,924 B2 5/2008 Raistrick et al.
7,465,303 B2 12/2008 Riccione et al.
7,473,255 B2 1/2009 Mcgarity et al.
7,540,874 B2 6/2009 Trumble et al.
7,572,258 B2 8/2009 Stiernborg
7,641,660 B2 1/2010 Lakin et al.
D610,257 S 2/2010 Horton
7,670,345 B2 3/2010 Plassky et al.
7,686,811 B2 3/2010 Byrd et al.
7,691,108 B2 4/2010 Lavallee
7,763,026 B2 7/2010 Egger et al.
7,789,885 B2 9/2010 Metzger
D629,900 S 12/2010 Fisher
7,875,058 B2 1/2011 Holmes, Jr.
7,972,338 B2 7/2011 O'Brien
7,983,777 B2 7/2011 Melton et al.
D646,389 S 10/2011 Claypool et al.
8,057,473 B2 11/2011 Orsak et al.
8,057,478 B2 11/2011 Kuczynski et al.
D651,315 S 12/2011 Bertoni et al.
D651,316 S 12/2011 May et al.
8,080,010 B2 12/2011 Schulz et al.
8,080,045 B2 12/2011 Wotton
8,114,087 B2 2/2012 Long et al.
8,123,753 B2 2/2012 Poncet
8,147,530 B2 4/2012 Strnad et al.
8,167,918 B2 5/2012 Strnad et al.
8,172,848 B2 5/2012 Tomko et al.
8,187,280 B2 5/2012 May et al.
8,192,441 B2 6/2012 Collazo
8,197,487 B2 6/2012 Poncet et al.
8,206,153 B2 6/2012 Suttin et al.
8,231,623 B1 7/2012 Jordan
8,231,663 B2 7/2012 Kay et al.
8,246,561 B1 8/2012 Agee et al.
8,246,680 B2 8/2012 Betz et al.
D666,721 S 9/2012 Wright et al.
8,262,664 B2 9/2012 Justin et al.
8,262,665 B2 9/2012 Massoud
8,277,455 B2 10/2012 Couture et al.
8,282,644 B2 10/2012 Edwards
8,282,645 B2 10/2012 Lawrence et al.
8,287,541 B2 10/2012 Nelson et al.
8,292,966 B2 10/2012 Morton
8,303,596 B2 11/2012 Plaky et al.
8,323,281 B2 12/2012 Hotchkiss et al.
8,323,289 B2 12/2012 Re
8,357,111 B2 1/2013 Caillouette et al.
8,377,105 B2 2/2013 Buscher
8,388,690 B2 3/2013 Singhatat et al.

(56) References Cited

U.S. PATENT DOCUMENTS

D679,395 S 4/2013 Wright et al.
8,435,246 B2 5/2013 Fisher et al.
8,475,462 B2 7/2013 Thomas et al.
8,484,001 B2 7/2013 Glozman et al.
8,518,045 B2 8/2013 Szanto
8,523,870 B2 9/2013 Green, II et al.
8,529,568 B2 9/2013 Bouadi
8,532,807 B2 9/2013 Metzger
8,551,106 B2 10/2013 Harrold
D694,884 S 12/2013 Mooradian et al.
D695,402 S 12/2013 Dacosta et al.
8,641,721 B2 2/2014 Aram et al.
8,652,142 B2 2/2014 Geissler
8,657,820 B2 2/2014 Kubiak et al.
D701,303 S 3/2014 Cook
8,663,234 B2 3/2014 Grimm et al.
8,668,700 B2 3/2014 Catanzarite et al.
8,685,030 B2 4/2014 Gtte et al.
8,696,719 B2 4/2014 Lofthouse et al.
8,702,686 B2 4/2014 Geebelen et al.
8,702,712 B2 4/2014 Jordan et al.
8,715,289 B2 5/2014 Smith
8,715,363 B2 5/2014 Ratron et al.
8,728,084 B2 5/2014 Berelsman et al.
8,758,354 B2 6/2014 Habegger et al.
8,777,948 B2 7/2014 Bernsteiner
8,784,457 B2 7/2014 Graham
8,795,286 B2 8/2014 Sand et al.
8,808,298 B2 8/2014 Raub et al.
8,808,301 B1 8/2014 Nofsinger
8,808,302 B2 8/2014 Roose et al.
8,828,012 B2 9/2014 May et al.
8,838,263 B2 9/2014 Sivak et al.
8,858,602 B2 10/2014 Weiner et al.
8,864,773 B2 10/2014 Paul et al.
8,882,778 B2 11/2014 Ranft
8,882,816 B2 11/2014 Kartalian et al.
8,892,235 B2 11/2014 Choi et al.
8,898,043 B2 11/2014 Ashby et al.
D720,456 S 12/2014 Dacosta et al.
8,900,247 B2 12/2014 Tseng et al.
8,911,444 B2 12/2014 Bailey
8,920,428 B2 12/2014 Zakaria et al.
8,926,612 B2 1/2015 Graham
8,932,299 B2 1/2015 Bono et al.
8,939,982 B2 1/2015 Chellaoui
8,939,984 B2 1/2015 Budoff
8,945,132 B2 2/2015 Play et al.
8,965,075 B2 2/2015 Arnaud et al.
8,974,460 B2 3/2015 De La Fuente et al.
8,979,856 B2 3/2015 Catanzarite et al.
8,992,531 B2 3/2015 Chow et al.
8,992,532 B2 3/2015 Wong
8,998,903 B2 4/2015 Price et al.
8,998,904 B2 4/2015 Zeetser et al.
8,998,907 B2 4/2015 Myers
8,998,909 B2 4/2015 Gillman et al.
9,005,207 B2 4/2015 Dodds et al.
9,011,451 B2 4/2015 Long et al.
9,011,452 B2 4/2015 Iannotti et al.
9,011,456 B2 4/2015 Ranawat et al.
9,014,835 B2 4/2015 Azernikov et al.
9,017,329 B2 4/2015 Tyber et al.
9,017,336 B2 4/2015 Park et al.
9,023,052 B2 5/2015 Lietz et al.
9,044,250 B2 6/2015 Olsen et al.
9,060,788 B2 6/2015 Bollinger
9,060,822 B2 6/2015 Wright et al.
9,089,376 B2 7/2015 Medoff et al.
9,101,421 B2 8/2015 Blacklidge
9,107,715 B2 8/2015 Blitz et al.
9,113,915 B2 8/2015 Thomas et al.
9,113,957 B2 8/2015 Axelson, Jr. et al.
9,138,237 B2 9/2015 Meade et al.
9,138,332 B2 9/2015 Harris et al.
D740,424 S 10/2015 Dacosta et al.
9,173,665 B2 11/2015 Couture
9,173,691 B2 11/2015 Orbay et al.
9,186,154 B2 11/2015 Li
9,186,160 B1 11/2015 Song
9,198,678 B2 12/2015 Frey et al.
9,204,897 B2 12/2015 Jones et al.
9,211,128 B2 12/2015 Gillman et al.
9,220,509 B2 12/2015 Boyer et al.
9,220,518 B2 12/2015 Neal et al.
9,220,519 B2 12/2015 Kaneyama et al.
9,220,551 B2 12/2015 Waizenegger
9,232,951 B2 1/2016 Johannaber
9,232,955 B2 1/2016 Bonin, Jr. et al.
9,254,155 B2 2/2016 Tannotti et al.
9,295,497 B2 3/2016 Schoenefeld et al.
9,301,768 B2 4/2016 Buza et al.
9,301,783 B2 4/2016 Gerold et al.
9,308,006 B2 4/2016 Martin et al.
9,308,037 B2 4/2016 Richter et al.
9,320,609 B2 4/2016 Schon et al.
9,345,497 B2 5/2016 Gonzalvez et al.
9,351,738 B2 5/2016 Aram et al.
9,351,743 B2 5/2016 Kehres et al.
9,370,380 B2 6/2016 Riccione
9,375,220 B2 6/2016 Horan et al.
9,402,636 B2 8/2016 Collazo
9,402,640 B2 8/2016 Reynolds et al.
9,408,641 B2 8/2016 Zhang et al.
9,414,846 B2 8/2016 Gillman et al.
9,414,847 B2 8/2016 Kurtz
9,414,877 B2 8/2016 Helenbolt et al.
9,421,021 B2 8/2016 Keppler
9,427,240 B2 8/2016 Von Zabern et al.
D765,844 S 9/2016 Dacosta
D766,434 S 9/2016 Dacosta
D766,437 S 9/2016 Dacosta
D766,438 S 9/2016 Dacosta
D766,439 S 9/2016 Dacosta
9,433,452 B2 9/2016 Weiner et al.
9,445,823 B2 9/2016 Harris et al.
9,452,050 B2 9/2016 Miles et al.
9,456,902 B2 10/2016 Hacking et al.
9,463,034 B2 10/2016 Wong et al.
9,492,182 B2 11/2016 Keefer
9,517,145 B2 12/2016 Meridew et al.
9,522,023 B2 12/2016 Haddad et al.
9,526,514 B2 12/2016 Kelley et al.
9,545,276 B2 1/2017 Buchanan et al.
9,561,041 B2 2/2017 Snider et al.
9,566,103 B2 2/2017 Mayer
9,579,106 B2 2/2017 Lo et al.
9,579,107 B2 2/2017 Schoenefeld
9,579,112 B2 2/2017 Catanzarite et al.
9,592,084 B2 3/2017 Grant
9,603,605 B2 3/2017 Collazo
9,603,640 B2 3/2017 Palmer et al.
9,622,820 B2 4/2017 Baloch et al.
9,629,726 B2 4/2017 Reiley et al.
9,652,889 B2 5/2017 Young et al.
9,662,220 B2 5/2017 Warburton
9,668,746 B2 6/2017 Lee et al.
9,675,471 B2 6/2017 Bojarski et al.
9,687,261 B2 6/2017 Serbousek et al.
9,693,787 B2 7/2017 Ammann et al.
9,693,878 B2 7/2017 Kunz et al.
9,700,433 B2 7/2017 Myers
9,713,484 B2 7/2017 Sammarco
9,737,311 B2 8/2017 Lavallee et al.
9,737,367 B2 8/2017 Steines et al.
9,750,538 B2 9/2017 Soffiatti et al.
9,785,747 B2 10/2017 Geebelen
9,788,958 B2 10/2017 Melamed et al.
9,788,975 B2 10/2017 Li
9,795,392 B2 10/2017 Zajac
9,795,394 B2 10/2017 Bonutti
9,814,474 B2 11/2017 Montoya et al.
9,820,868 B2 11/2017 Witt et al.
9,826,981 B2 11/2017 Schoenefeld et al.

(56) References Cited

U.S. PATENT DOCUMENTS 9,839,438 B2 12/2017 Eash
9,848,929 B2 12/2017 Dacosta et al.
9,849,019 B2 12/2017 Miller et al.
9,877,754 B2 1/2018 Patel et al.
9,883,954 B1 2/2018 Murphy
9,888,931 B2 2/2018 Bake
9,888,950 B2 2/2018 Perez et al.
9,918,658 B2 3/2018 Mccaulley et al.
9,918,769 B2 3/2018 Provencher et al.
9,925,049 B2 3/2018 Goldstein et al.
9,925,068 B2 3/2018 Bays et al.
9,956,089 B2 5/2018 Kelman et al.
9,968,456 B2 5/2018 Song
9,980,760 B2 5/2018 Dacosta et al.
9,987,092 B2 6/2018 Hladio et al.
9,990,765 B2 6/2018 Ju et al.
9,993,256 B2 6/2018 Lipman et al.
10,002,227 B2 6/2018 Netravali et al.
10,004,516 B2 6/2018 Johannaber
10,010,431 B2 7/2018 Eraly et al.
10,016,177 B2 7/2018 Aram et al.
10,022,170 B2 7/2018 Leemrijse et al.
10,028,756 B2 7/2018 Liu
10,034,753 B2 7/2018 Dressler et al.
10,052,114 B2 8/2018 Keppler et al.
10,055,536 B2 8/2018 Maes et al.
10,058,335 B2 8/2018 Lee et al.
10,089,413 B2 10/2018 Wirx-Speetjens et al.
10,098,761 B2 10/2018 Sherman et al.
10,105,145 B2 10/2018 Lavallee
10,123,807 B2 11/2018 Geebelen
10,130,378 B2 11/2018 Bryan
10,149,722 B2 12/2018 Aram et al.
10,159,480 B2 12/2018 Tuten
10,159,499 B2 12/2018 Dacosta et al.
10,159,512 B2 12/2018 Robinson
10,201,357 B2 2/2019 Aram et al.
10,206,692 B2 2/2019 Sanders
10,217,530 B2 2/2019 Couture et al.
10,219,812 B2 3/2019 Torrie et al.
10,226,292 B2 3/2019 Lundquist et al.
10,231,745 B2 3/2019 Geebelen et al.
10,238,382 B2 3/2019 Terrill et al.
10,251,654 B2 4/2019 Fritzinger
10,251,690 B2 4/2019 Katrana et al.
10,262,084 B2 4/2019 Lavallee et al.
10,265,080 B2 4/2019 Hughes et al.
10,271,886 B2 4/2019 Abiven
10,278,713 B2 5/2019 Richter et al.
10,282,488 B2 5/2019 Eash
10,286,197 B2 5/2019 Pouliot et al.
10,325,065 B2 6/2019 Li et al.
10,327,829 B2 6/2019 Dacosta et al.
10,342,529 B2 7/2019 Fallin et al.
10,350,022 B2 7/2019 Jansen et al.
10,357,261 B2 7/2019 Kugler et al.
10,357,299 B2 7/2019 Weiner et al.
10,363,052 B2 7/2019 Park et al.
10,398,510 B2 9/2019 Goto
10,420,613 B2 9/2019 Azevedo Da Silva et al.
10,456,205 B2 10/2019 Meridew et al.
10,512,470 B1 12/2019 Bays et al.
10,524,808 B1 1/2020 Hissong et al.
10,524,845 B2 1/2020 Orsak et al.
10,537,392 B2 1/2020 Millahn et al.
10,543,100 B2 1/2020 Couture et al.
10,548,667 B2 2/2020 Flett et al.
10,548,668 B2 2/2020 Furrer et al.
10,582,969 B2 3/2020 Couture et al.
10,610,241 B2 4/2020 Wagner et al.
10,631,878 B2 4/2020 Fritzinger
10,631,902 B2 4/2020 Weiner et al.
10,653,432 B2 5/2020 Luttrell et al.
10,653,464 B2 5/2020 Hill et al.
10,653,467 B2 5/2020 Brumfield et al.
10,675,096 B2 6/2020 Utz et al.
10,682,147 B2 6/2020 Grant et al.
10,709,567 B2 7/2020 Welker et al.
10,716,581 B2 7/2020 Fritzinger et al.
10,722,309 B2 7/2020 Gillman
10,722,310 B2 7/2020 Luby
10,779,867 B2 9/2020 Penzimer et al.
10,779,890 B2 9/2020 Weir
10,786,291 B2 9/2020 Weiner et al.
10,792,081 B2 10/2020 Weiner et al.
10,806,469 B2 10/2020 Fiechter et al.
10,849,665 B2 12/2020 Singh et al.
10,849,670 B2 12/2020 Santrock et al.
10,856,891 B2 12/2020 Rhodes et al.
10,856,925 B1 12/2020 Pontell
10,869,722 B2 12/2020 Caldwell et al.
10,874,408 B2 12/2020 Couture
10,881,416 B2 1/2021 Couture et al.
10,881,417 B2 1/2021 Mahfouz
10,888,340 B2 1/2021 Awtrey et al.
10,905,444 B2 2/2021 Siccardi et al.
10,912,574 B2 2/2021 Kim et al.
10,925,622 B2 2/2021 Kehres et al.
10,939,926 B2 3/2021 Kam et al.
10,939,939 B1 3/2021 Gil et al.
10,973,529 B2 4/2021 Lavallee et al.
11,000,327 B2 5/2021 Schlotterback et al.
11,020,128 B2 6/2021 Guilloux et al.
11,033,336 B2 6/2021 Bohl
11,065,011 B2 7/2021 Bake et al.
11,074,688 B2 7/2021 Chabin et al.
11,090,069 B2 8/2021 Park
11,090,161 B2 8/2021 Hodorek
11,112,770 B2 9/2021 Roh et al.
11,116,518 B2 9/2021 Hafez
11,129,625 B2 9/2021 Song et al.
11,129,678 B2 9/2021 Park
11,154,362 B2 10/2021 Kim et al.
11,158,047 B2 10/2021 Shah
11,160,567 B2 11/2021 Fallin et al.
11,160,568 B1 11/2021 Park
11,166,732 B2 11/2021 Maxson et al.
11,172,945 B1 11/2021 Lian
11,179,165 B2 11/2021 Schoenefeld
11,179,168 B2 11/2021 Dacosta et al.
11,207,134 B2 12/2021 Hafez
11,213,305 B2 1/2022 Iannotti et al.
11,213,406 B2 1/2022 Rodriguez et al.
11,219,526 B2 1/2022 Mahfouz
11,224,448 B2 1/2022 Bailey
11,259,817 B2 3/2022 Fallin et al.
11,284,909 B2 3/2022 Castricini et al.
11,304,705 B2 4/2022 Fallin et al.
11,304,735 B2 4/2022 Sayger et al.
11,324,522 B2 5/2022 Metzger et al.
11,324,607 B2 5/2022 Mauldin et al.
11,331,148 B2 5/2022 Fritzinger
11,331,205 B2 5/2022 Parr
11,344,347 B2 5/2022 Treace et al.
11,389,221 B2 7/2022 Tyber et al.
11,399,849 B2 8/2022 Larche et al.
11,419,726 B2 8/2022 Miller et al.
11,426,184 B2 8/2022 Rivet-Sabourin et al.
11,432,931 B2 9/2022 Lang
11,436,801 B2 9/2022 Haslam et al.
11,439,412 B2 9/2022 Woodard et al.
11,457,980 B2 10/2022 Bonny et al.
11,484,354 B2 11/2022 Singh et al.
11,497,557 B2 11/2022 Haslam et al.
11,508,102 B2 11/2022 Su et al.
11,510,738 B2 11/2022 Stifter et al.
11,532,402 B2 12/2022 Farley et al.
11,557,036 B2 1/2023 Mansi et al.
11,583,298 B2 2/2023 Robichaud et al.
11,596,421 B2 3/2023 Saltzman et al.
11,596,443 B2 3/2023 Treace et al.
11,602,386 B2 3/2023 Smith et al.
11,607,250 B2 3/2023 Treace et al.
11,627,954 B2 4/2023 May et al.

(56) References Cited

U.S. PATENT DOCUMENTS

| | | | |
|---|---|---|---|
| 11,628,003 B2 | 4/2023 | Nachtrab et al. | |
| 11,633,195 B2 | 4/2023 | Dhillon | |
| 11,648,019 B2 | 5/2023 | Bays et al. | |
| 11,653,938 B2 | 5/2023 | Siegler | |
| 11,684,423 B2 | 6/2023 | Jaramaz et al. | |
| 11,690,725 B2 | 7/2023 | Gemon et al. | |
| 11,717,359 B2 | 8/2023 | Chi | |
| 11,741,277 B2 | 8/2023 | Dayal et al. | |
| 11,751,892 B2 | 9/2023 | Woodard et al. | |
| 11,756,051 B2 | 9/2023 | Indani et al. | |
| 11,766,268 B2 | 9/2023 | Iannotti et al. | |
| 11,779,467 B2 | 10/2023 | Mimnaugh et al. | |
| 11,786,257 B2 | 10/2023 | Dayton et al. | |
| 11,793,549 B2 | 10/2023 | Rhodes et al. | |
| 11,812,978 B2 | 11/2023 | Trabish et al. | |
| 11,819,223 B2 | 11/2023 | Lee | |
| 11,819,224 B2 | 11/2023 | Allard et al. | |
| 11,849,933 B2 | 12/2023 | Denham et al. | |
| 11,849,957 B2 | 12/2023 | Couture et al. | |
| 11,849,961 B2 | 12/2023 | Khatibi et al. | |
| 11,849,962 B2 | 12/2023 | Singh et al. | |
| 11,854,683 B2 | 12/2023 | Casey et al. | |
| D1,011,524 S | 1/2024 | Santrock et al. | |
| 11,857,206 B2 | 1/2024 | Robichaud et al. | |
| 11,864,778 B2 | 1/2024 | Mcginley et al. | |
| 11,864,959 B2 | 1/2024 | Basta | |
| 11,911,046 B2 | 2/2024 | Carroll et al. | |
| 11,925,417 B2 | 3/2024 | Mosnier et al. | |
| 11,931,106 B2 | 3/2024 | Perler et al. | |
| 11,944,546 B2 | 4/2024 | Puncreobutr et al. | |
| 11,950,786 B2 | 4/2024 | Courtis et al. | |
| 11,963,687 B2 | 4/2024 | Langhorn et al. | |
| 11,963,703 B2 | 4/2024 | Dayton et al. | |
| 11,963,729 B2 | 4/2024 | Aljuri et al. | |
| 11,980,377 B2 | 5/2024 | Mauldin et al. | |
| 12,004,789 B2 | 6/2024 | Mcaleer et al. | |
| 12,004,814 B2 | 6/2024 | Ryan et al. | |
| D1,034,985 S | 7/2024 | Hartson et al. | |
| 12,035,929 B2 | 7/2024 | Athwal et al. | |
| 12,045,943 B2 | 7/2024 | Chaoui et al. | |
| 12,048,600 B2 | 7/2024 | Azernikov et al. | |
| 12,050,999 B2 | 7/2024 | Poltaretskyi et al. | |
| 12,053,242 B2 | 8/2024 | Landon et al. | |
| 12,062,183 B2 | 8/2024 | Chaoui et al. | |
| 12,097,129 B2 | 9/2024 | Deransart et al. | |
| 12,115,083 B2 | 10/2024 | Mullen et al. | |
| 12,121,272 B2 | 10/2024 | Marien et al. | |
| 2002/0107519 A1 | 8/2002 | Dixon et al. | |
| 2003/0236522 A1 | 12/2003 | Long et al. | |
| 2004/0010259 A1 | 1/2004 | Keller et al. | |
| 2004/0039394 A1 | 2/2004 | Conti et al. | |
| 2004/0039396 A1 | 2/2004 | Couture et al. | |
| 2004/0097946 A1 | 5/2004 | Dietzel et al. | |
| 2004/0138669 A1 | 7/2004 | Horn | |
| 2004/0260291 A1* | 12/2004 | Jensen | A61B 17/8057 606/915 |
| 2005/0059978 A1 | 3/2005 | Sherry et al. | |
| 2005/0080424 A1 | 4/2005 | Cuckler et al. | |
| 2005/0267482 A1 | 12/2005 | Hyde | |
| 2005/0273112 A1 | 12/2005 | Mcnamara | |
| 2006/0129163 A1 | 6/2006 | Mcguire | |
| 2006/0206044 A1 | 9/2006 | Simon | |
| 2006/0229621 A1 | 10/2006 | Cadmus | |
| 2006/0241607 A1 | 10/2006 | Myerson et al. | |
| 2006/0241608 A1 | 10/2006 | Myerson et al. | |
| 2006/0264961 A1 | 11/2006 | Murray-Brown | |
| 2007/0010818 A1 | 1/2007 | Stone et al. | |
| 2007/0123857 A1 | 5/2007 | Deffenbaugh et al. | |
| 2007/0233138 A1 | 10/2007 | Figueroa et al. | |
| 2007/0265634 A1 | 11/2007 | Weinstein | |
| 2007/0276383 A1 | 11/2007 | Rayhack | |
| 2008/0009863 A1 | 1/2008 | Bond et al. | |
| 2008/0039850 A1 | 2/2008 | Rowley et al. | |
| 2008/0091197 A1 | 4/2008 | Coughlin | |
| 2008/0140081 A1 | 6/2008 | Heavener et al. | |
| 2008/0161815 A1 | 7/2008 | Schoenefeld et al. | |
| 2008/0172054 A1 | 7/2008 | Claypool et al. | |
| 2008/0288004 A1 | 11/2008 | Schendel | |
| 2009/0036931 A1 | 2/2009 | Pech et al. | |
| 2009/0089081 A1 | 4/2009 | Haddad | |
| 2009/0093849 A1 | 4/2009 | Grabowski | |
| 2009/0105767 A1 | 4/2009 | Reiley | |
| 2009/0198244 A1 | 8/2009 | Leibel | |
| 2009/0216089 A1 | 8/2009 | Davidson | |
| 2009/0222047 A1 | 9/2009 | Graham | |
| 2009/0254092 A1 | 10/2009 | Albiol Llorach | |
| 2009/0254126 A1 | 10/2009 | Orbay et al. | |
| 2009/0265012 A1 | 10/2009 | Engh et al. | |
| 2009/0287309 A1 | 11/2009 | Walch et al. | |
| 2010/0069910 A1 | 3/2010 | Hasselman | |
| 2010/0082035 A1* | 4/2010 | Keefer | A61B 17/1666 606/91 |
| 2010/0130981 A1 | 5/2010 | Richards | |
| 2010/0145351 A1* | 6/2010 | Ashman | A61B 17/1796 606/96 |
| 2010/0168799 A1 | 7/2010 | Schumer | |
| 2010/0185202 A1 | 7/2010 | Lester et al. | |
| 2010/0217270 A1 | 8/2010 | Polinski et al. | |
| 2010/0256687 A1 | 10/2010 | Neufeld et al. | |
| 2010/0274253 A1 | 10/2010 | Ure | |
| 2010/0318088 A1 | 12/2010 | Warne et al. | |
| 2011/0009865 A1 | 1/2011 | Orfaly | |
| 2011/0015639 A1* | 1/2011 | Metzger | A61B 17/175 623/22.21 |
| 2011/0106093 A1* | 5/2011 | Romano | A61B 17/1675 606/88 |
| 2012/0041445 A1* | 2/2012 | Roose | A61B 17/1746 606/96 |
| 2012/0065689 A1 | 3/2012 | Prasad et al. | |
| 2012/0116203 A1 | 5/2012 | Vancraen et al. | |
| 2012/0123420 A1 | 5/2012 | Honiball | |
| 2012/0130434 A1 | 5/2012 | Stemniski | |
| 2012/0150242 A1 | 6/2012 | Mannion | |
| 2012/0191199 A1 | 7/2012 | Raemisch | |
| 2012/0234329 A1 | 9/2012 | Vancraen et al. | |
| 2012/0253350 A1 | 10/2012 | Anthony et al. | |
| 2012/0265301 A1 | 10/2012 | Demers et al. | |
| 2012/0277745 A1 | 11/2012 | Lizee | |
| 2013/0211410 A1 | 8/2013 | Landes et al. | |
| 2013/0236874 A1 | 9/2013 | Tannotti et al. | |
| 2013/0237989 A1 | 9/2013 | Bonutti | |
| 2013/0274778 A1 | 10/2013 | Mercier et al. | |
| 2013/0289570 A1 | 10/2013 | Chao | |
| 2013/0292870 A1 | 11/2013 | Roger | |
| 2014/0005672 A1 | 1/2014 | Edwards et al. | |
| 2014/0039501 A1 | 2/2014 | Schickendantz et al. | |
| 2014/0074099 A1 | 3/2014 | Vigneron et al. | |
| 2014/0094861 A1 | 4/2014 | Fallin | |
| 2014/0163568 A1 | 6/2014 | Wong et al. | |
| 2014/0257402 A1 | 9/2014 | Barsoum | |
| 2014/0259629 A1 | 9/2014 | Dion et al. | |
| 2014/0263674 A1 | 9/2014 | Cerveny | |
| 2014/0343555 A1 | 11/2014 | Russi et al. | |
| 2014/0371866 A1 | 12/2014 | Chao et al. | |
| 2014/0371897 A1 | 12/2014 | Lin et al. | |
| 2015/0032215 A1 | 1/2015 | Slamin et al. | |
| 2015/0045903 A1 | 2/2015 | Neal | |
| 2015/0066094 A1 | 3/2015 | Anderson et al. | |
| 2015/0081029 A1 | 3/2015 | Bojarski et al. | |
| 2015/0088142 A1 | 3/2015 | Gibson | |
| 2015/0093283 A1 | 4/2015 | Miller et al. | |
| 2015/0112348 A1 | 4/2015 | Schoenefeld et al. | |
| 2015/0142000 A1 | 5/2015 | Seedhom et al. | |
| 2015/0182342 A1 | 7/2015 | Hafez | |
| 2015/0227679 A1 | 8/2015 | Kamer et al. | |
| 2015/0230843 A1 | 8/2015 | Palmer et al. | |
| 2015/0305752 A1 | 10/2015 | Eash | |
| 2015/0342616 A1 | 12/2015 | Fryman | |
| 2015/0351780 A1 | 12/2015 | Anderson et al. | |
| 2015/0351916 A1 | 12/2015 | Kosarek et al. | |
| 2016/0015426 A1 | 1/2016 | Dayton | |
| 2016/0038161 A1 | 2/2016 | Gibson | |
| 2016/0100773 A1 | 4/2016 | Ching et al. | |
| 2016/0100847 A1 | 4/2016 | Maxson | |

(56) References Cited

U.S. PATENT DOCUMENTS

2016/0151165 A1 6/2016 Fallin et al.
2016/0175089 A1 6/2016 Fallin et al.
2016/0192951 A1 7/2016 Gelaude et al.
2016/0199198 A1 7/2016 Dietz et al.
2016/0256176 A9 9/2016 Lowery et al.
2016/0270829 A1 9/2016 Duggal et al.
2016/0270855 A1 9/2016 Kunz et al.
2016/0287395 A1 10/2016 Khalili et al.
2016/0338715 A1 11/2016 Bojarski et al.
2016/0354128 A1 12/2016 Jeng et al.
2016/0367270 A1 12/2016 Garlock et al.
2017/0014169 A1 1/2017 Dean et al.
2017/0020537 A1 1/2017 Tuten
2017/0027593 A1 2/2017 Bojarski et al.
2017/0079803 A1 3/2017 Lang
2017/0143511 A1 5/2017 Cachia
2017/0209189 A9 7/2017 Hatch et al.
2017/0231645 A1 8/2017 Metzger et al.
2017/0245906 A1 8/2017 Kugler et al.
2017/0245935 A1 8/2017 Kugler et al.
2017/0249440 A1 8/2017 Lang et al.
2017/0281353 A1 10/2017 Al Hares et al.
2017/0360578 A1 12/2017 Shin et al.
2018/0021145 A1 1/2018 Seavey et al.
2018/0028325 A1 2/2018 Bojarski et al.
2018/0049758 A1 2/2018 Amis et al.
2018/0116804 A1 5/2018 Hafez et al.
2018/0221071 A1 8/2018 Isch
2018/0235706 A1 8/2018 Asseln et al.
2018/0242987 A1 8/2018 Lintula et al.
2018/0289423 A1 10/2018 Singh et al.
2018/0317986 A1 11/2018 Jackman et al.
2018/0344326 A1 12/2018 Chan et al.
2019/0000629 A1 1/2019 Winslow
2019/0008532 A1 1/2019 Fitz et al.
2019/0117239 A1 4/2019 Verma
2019/0175277 A1 6/2019 Chav et al.
2019/0175351 A1 6/2019 Bojarski et al.
2019/0307495 A1 10/2019 Geldwert
2019/0365543 A1 12/2019 Slamin et al.
2020/0008813 A1 1/2020 Bonny et al.
2020/0046425 A1 2/2020 Lopes et al.
2020/0100909 A1 4/2020 Lang et al.
2020/0155323 A1 5/2020 Lang et al.
2020/0163721 A1 5/2020 Aghazadeh
2020/0214719 A1 7/2020 Fraone et al.
2020/0337714 A1 10/2020 Hafez et al.
2020/0356073 A1 11/2020 Tokushima
2020/0405322 A1 12/2020 Brailovski et al.
2021/0007760 A1 1/2021 Reisin
2021/0022781 A1 1/2021 Dacosta et al.
2021/0030429 A1 2/2021 Rose et al.
2021/0045756 A1 2/2021 Zakhary et al.
2021/0059691 A1 3/2021 Zille
2021/0059837 A1 3/2021 Rhodes
2021/0077120 A1 3/2021 Hatch et al.
2021/0077192 A1* 3/2021 Perler .................... A61B 34/10
2021/0085338 A1 3/2021 Dacosta et al.
2021/0090248 A1 3/2021 Choi et al.
2021/0106427 A1 4/2021 Mahfouz
2021/0113223 A1 4/2021 Schaumann et al.
2021/0121297 A1 4/2021 Cavanagh et al.
2021/0137537 A1 5/2021 Zille
2021/0161543 A1 6/2021 Mcauliffe et al.
2021/0186704 A1 6/2021 Fitz et al.
2021/0192759 A1 6/2021 Lang
2021/0196290 A1 7/2021 Iannotti et al.
2021/0212705 A1 7/2021 Reynolds et al.
2021/0219989 A1 7/2021 Chao
2021/0244477 A1 8/2021 Singh et al.
2021/0256171 A1 8/2021 Hosseini
2021/0275196 A1 9/2021 Wodajo
2021/0282790 A1 9/2021 Sellman et al.
2021/0282823 A1 9/2021 Day et al.
2021/0290250 A1 9/2021 Denham et al.
2021/0298766 A1 9/2021 Loring et al.
2021/0307833 A1 10/2021 Farley et al.
2021/0307834 A1 10/2021 Gillman et al.
2021/0346038 A1* 11/2021 Fiechter ............ A61B 17/1757
2021/0378752 A1 12/2021 Paul et al.
2021/0386437 A1 12/2021 Dacosta et al.
2021/0391058 A1 12/2021 Kostrzewski et al.
2021/0393304 A1 12/2021 Geldwert
2022/0039965 A1 2/2022 Casey et al.
2022/0087822 A1 3/2022 Radermacher et al.
2022/0096157 A1 3/2022 Pollock et al.
2022/0133484 A1 5/2022 Lang
2022/0160405 A1 5/2022 Casey et al.
2022/0167998 A1 6/2022 Siccardi et al.
2022/0192685 A1 6/2022 Gazonnet et al.
2022/0202495 A1 6/2022 Pack
2022/0211387 A1 7/2022 Perler et al.
2022/0233203 A1 7/2022 Rhodes et al.
2022/0249106 A1 8/2022 Akallal et al.
2022/0249143 A1 8/2022 Hollis et al.
2022/0270762 A1 8/2022 Crawford et al.
2022/0273450 A1 9/2022 Steines et al.
2022/0296285 A1 9/2022 Besque et al.
2022/0313284 A1 10/2022 Korman
2022/0323086 A1 10/2022 Stemniski et al.
2022/0338934 A1 10/2022 Perler et al.
2022/0346806 A1 11/2022 Leemrijse et al.
2023/0013727 A1 1/2023 Korman et al.
2023/0014384 A1 1/2023 Cordonnier et al.
2023/0077222 A1 3/2023 Awtrey
2023/0157705 A1 5/2023 Reynolds
2023/0190306 A1 6/2023 Kowalczyk et al.
2023/0281842 A1 9/2023 Ribeiro et al.
2023/0310013 A1 10/2023 Perler et al.
2023/0310051 A1 10/2023 Hafez et al.
2023/0363773 A1 11/2023 Perler et al.
2023/0371966 A1 11/2023 Spitler
2023/0389937 A1 12/2023 Penner et al.
2023/0404673 A1 12/2023 Spitler et al.
2024/0005504 A1 1/2024 Ribeiro et al.
2024/0008880 A1 1/2024 Spitler et al.

FOREIGN PATENT DOCUMENTS

AU 2015203808 B2 9/2017
AU 2020220169 A1 9/2020
AU 2021286392 A1 1/2022
CA 2491824 A1 9/2005
CA 2608464 C 7/2012
CA 2854997 A1 5/2013
CA 2713309 C 7/2013
CH 695846 A5 9/2006
CN 2930668 Y 8/2007
CN 201558162 U 8/2010
CN 201572172 U 9/2010
CN 201586060 U 9/2010
CN 201912210 U 8/2011
CN 101237835 B 11/2012
CN 202801773 U 3/2013
CN 103462675 A 12/2013
CN 103505276 A 1/2014
CN 203458450 U 3/2014
CN 102860860 B 5/2014
CN 203576647 U 5/2014
CN 104490460 A 4/2015
CN 104510523 A 4/2015
CN 104523327 A 4/2015
CN 104546102 A 4/2015
CN 204379413 U 6/2015
CN 204410951 U 6/2015
CN 204428143 U 7/2015
CN 204428144 U 7/2015
CN 204428145 U 7/2015
CN 204446081 U 7/2015
CN 106236185 A 12/2016
CN 205924106 U 2/2017
CN 206151532 U 5/2017
CN 105105853 B 7/2017
CN 108030532 A 5/2018

(56) References Cited

FOREIGN PATENT DOCUMENTS

| | | | |
|---|---|---|---|
| CN | 207721902 | U | 8/2018 |
| CN | 112914724 | B | 2/2022 |
| CN | 117297772 | B | 2/2024 |
| CN | 117322951 | B | 2/2024 |
| CN | 109223098 | B | 5/2024 |
| DE | 2910627 | A1 | 9/1980 |
| DE | 202006010241 | U1 | 3/2007 |
| DE | 102007053058 | B3 | 4/2009 |
| EP | 685206 | B1 | 9/2000 |
| EP | 1508316 | B1 | 5/2007 |
| EP | 1897509 | B1 | 7/2009 |
| EP | 2124832 | B1 | 8/2012 |
| EP | 2750617 | A1 | 7/2014 |
| EP | 2856951 | A1 | 4/2015 |
| EP | 2624764 | B1 | 12/2015 |
| EP | 3000443 | A3 | 7/2016 |
| EP | 2083758 | B1 | 11/2017 |
| EP | 2632349 | B1 | 3/2018 |
| EP | 3013256 | B1 | 11/2018 |
| EP | 3171795 | B1 | 11/2018 |
| EP | 3672535 | A1 | 7/2020 |
| EP | 2558010 | B1 | 5/2021 |
| EP | 3948895 | A1 | 2/2022 |
| EP | 3740141 | B1 | 4/2022 |
| EP | 2844162 | B1 | 7/2022 |
| FR | 2362616 | A1 | 3/1978 |
| FR | 2764183 | A1 | 12/1998 |
| FR | 2953120 | B1 | 1/2012 |
| FR | 3030221 | A1 | 6/2016 |
| FR | 3117328 | B1 | 3/2023 |
| GB | 2154143 | A | 9/1985 |
| GB | 2154144 | A | 9/1985 |
| GB | 2334214 | B | 1/2003 |
| GB | 2589960 | A | 6/2021 |
| JP | S635739 | A | 1/1988 |
| JP | 2004174265 | A | 6/2004 |
| JP | 2006158972 | A | 6/2006 |
| JP | 4134243 | B2 | 8/2008 |
| JP | 2011092405 | A | 5/2011 |
| JP | 4796943 | B2 | 10/2011 |
| JP | 2014511207 | A | 5/2014 |
| JP | 2014521384 | A | 8/2014 |
| KR | 100904142 | B1 | 6/2009 |
| KR | 1020160090006 | A | 7/2016 |
| KR | 1020180118476 | A | 10/2018 |
| KR | 101952368 | B1 | 2/2019 |
| MD | 756Z | B1 | 7/1997 |
| RU | 2098036 | C1 | 12/1997 |
| RU | 2195892 | C2 | 1/2003 |
| RU | 2320287 | C1 | 3/2008 |
| RU | 2321366 | C2 | 4/2008 |
| RU | 2321369 | C1 | 4/2008 |
| RU | 2346663 | C2 | 2/2009 |
| RU | 2412662 | C1 | 2/2011 |
| RU | 182499 | U1 | 8/2018 |
| RU | 2789960 | C2 | 2/2023 |
| SU | 1333328 | A2 | 8/1987 |
| WO | 0166022 | A1 | 9/2001 |
| WO | 03075775 | A1 | 9/2003 |
| WO | 2004089227 | A2 | 10/2004 |
| WO | 2008051064 | A1 | 5/2008 |
| WO | 2009001083 | A1 | 12/2008 |
| WO | 2009029798 | A1 | 3/2009 |
| WO | 2009032101 | A2 | 3/2009 |
| WO | 2010099231 | A3 | 11/2010 |
| WO | 2011005327 | A1 | 1/2011 |
| WO | 2011037885 | A1 | 3/2011 |
| WO | 2012024317 | A2 | 2/2012 |
| WO | 2012029008 | A1 | 3/2012 |
| WO | 2012176077 | A1 | 12/2012 |
| WO | 2013026786 | A1 | 2/2013 |
| WO | 2013041618 | A1 | 3/2013 |
| WO | 2013134387 | A1 | 9/2013 |
| WO | 2013156816 | A2 | 10/2013 |
| WO | 2014020561 | A1 | 2/2014 |
| WO | 2014020562 | A1 | 2/2014 |
| WO | 2014022055 | A1 | 2/2014 |
| WO | 2014085882 | A1 | 6/2014 |
| WO | 2014147099 | A1 | 9/2014 |
| WO | 2014152219 | A2 | 9/2014 |
| WO | 2014200017 | A1 | 12/2014 |
| WO | 2015003284 | A2 | 1/2015 |
| WO | 2015094409 | A1 | 6/2015 |
| WO | 2015127515 | A2 | 9/2015 |
| WO | 2016012731 | A1 | 1/2016 |
| WO | 2016102025 | A1 | 6/2016 |
| WO | 2017031000 | A1 | 2/2017 |
| WO | 2017122076 | A2 | 7/2017 |
| WO | 2017151833 | A1 | 9/2017 |
| WO | 2018167369 | A1 | 9/2018 |
| WO | 2019060780 | A2 | 3/2019 |
| WO | 2019052622 | A4 | 5/2019 |
| WO | 2019180747 | A1 | 9/2019 |
| WO | 2020060349 | A1 | 3/2020 |
| WO | 2021054518 | A1 | 3/2021 |
| WO | 2021091071 | A1 | 5/2021 |
| WO | 2021118733 | A1 | 6/2021 |
| WO | 2021127625 | A1 | 6/2021 |
| WO | 2021240290 | A1 | 12/2021 |
| WO | 2022155208 | A1 | 7/2022 |
| WO | 2022182312 | A1 | 9/2022 |
| WO | 2023096516 | A1 | 6/2023 |
| WO | 2024025840 | A1 | 2/2024 |

OTHER PUBLICATIONS

"Lapidus Pearls: Gaining Joint Exposure to Decrease Non-Union," Youtube, Retrieved online from <https://www.youtube.com/watch?v=-jqJyE7pj-Y>, dated Nov. 2, 2009, 3 pages.

"Reconstructive Surgery of the Foot & Ankle," The Podiatry Institute, Update 2015, Conference Program, May 2015, 28 pages.

"Speed Continuous Active Compression Implant," BioMedical Enterprises, Inc., A120-029 Rev. 3, 2013, 4 pages.

"Visionaire: Patient Matched Cutting Blocks Surgical Procedure," Smith & Nephew, Inc., 2009, 2 pages.

Acumed "Acumed Osteotomy System" with partial English Translation, 2014, pp. 19.

Additive Orthopaedics, "The First and Only FDA Approved Patient Specific Talus Spacer", https://totaltalusreplacement.com, Downloaded: Mar. 4, 2022, pp. 11.

Aiyer et al. "Prevalence of Metatarsus Adductus in Patients Undergoing Hallux Valgus Surgery" Foot & Ankle International 2014, vol. 35(12), pp. 1292-1297.

Albano et al. "Biomechanical Study of Transcortical or Transtrabecular Bone Fixation of Patellar Tendon Graft With Bioabsorbable Pins in ACL Reconstruction in Sheep" Rev Bras Ortop. 2012, 47(1), pp. 43-49.

Alvine et al. "Peg and Dowel Fusion of the Proximal Interphalangeal Joint" Foot & Ankle vol. 1, No. 2, 1980 American Orthopaedic Foot Society, pp. 5.

Arthrex "Chevron Osteotomy" https://www.arthrex.com/foot-ankle/chevron-osteotomy, Retrieved Nov. 30, 2022, pp. 7.

Arthrex "Comprehensive Foot System" https://www.arthrex.com/resources/animation/8U3iaPvY6kO8bwFAwZF50Q/comprehensive-foot-system?referringTeam=foot_and_ankle, Published Aug. 27, 2013, pp. 3.

Arthrex, "Distal Tibia Allograft Workstation for Glenoid Bone Loss, Surgical Technique" Arthrex.com, 2018, pp. 8.

Baravarian, "Why the Lapidus Procedure is Ideal for Bunions" Podiatry Today, https://www.hmpgloballearningnetwork.com/site/podiatry/article/5542, May 2006 pp. 8.

Bauer et al. "Offset-V Osteotomy of the First Metatarsal Shaft in Hallux Abducto Valgus" Chapter 29, McGlamry's Comprehensive Textbook of Foot and Ankle Surgery, Fourth Edition, 2013, pp. 26.

Bednarz et al. "Modified Lapidus Procedure for the Treatment of Hypermobile Hallux Valgus" Foot & Ankle, American Orthopaedic Foot & Ankle Society, 2000, pp. 6.

Bennett et al. "Intraosseous Sliding Plate Fixation Used in Double Osteotomy Bunionectomy" Foot & Ankle International, 2019, vol. 40(1), pp. 85-88.

(56) References Cited

OTHER PUBLICATIONS

Biopro "Accu-Cut Osteotomy Guide System Accurate and consistent hallux valgus correction" Document Dates Sep. 16, 2019, pp. 2.
Boffeli et al. "Can We Abandon Saw Wedge Resection in Lapidus Fusion? A Comparative Study of Joint Preparation Techniques Regarding Correction of Deformity, Union Rate, and Preservation of First Ray Length" The Journal of Foot & Ankle Surgery, 58, 2019, pp. 1118-1124.
Bouaicha et al. "Fixation of Maximal Shift Scarf Osteotomy with Inside-Out Plating: Technique Tip" Foot & Ankle International, vol. 32, No. 5, May 2011, pp. 567-569.
Buda et al. "Effect of Fixation Type and Bone Graft on Tarsometatarsal Fusion" Foot & Ankle International 2018, vol. 39(12), pp. 1394-1402.
Carr et al. "Correctional Osteotomy for Metatarsus Primus Varus and Hallux Valgus*" The Journal of Bone and Joint Surgery, vol. 50-A, No. 7, Oct. 1968, pp. 1353-1367.
Catanese et al. "Measuring Sesamoid Position in Hallux Valgus When Is the Sesamoid Axial View Necessary?" Foot & Ankle Specialist, Downloaded Aug. 15, 2016, pp. 1-3.
Chesser et al. "New Advances With The Tarsometatarsal" Podiatry Today, vol. 30, Issue 10, Oct. 2017, pp. 28-36.
Chomej et al. "Lateralising DMMO (MIS) for simultaneous correction of a pes adductus during surgical treatment of a hallux valgus" Journal Pre-proof, The Foot, Accepted Jul. 16, 2020, pp. 33.
Cichero et al. "Different fixation constructs and the risk of non-union following first metatarsophalangeal joint arthrodesis" Foot and Ankle Surgery, 27, 2021, Accepted Oct. 15, 2020, pp. 789-792.
Coetzee et al., "Revision Hallux Valgus Correction," Operative Techniques in Foot and Ankle Surgery, Section I, Chapter 15, 2011, pp. 84-96.
Collan et al., "The biomechanics of the first metatarsal bone in hallux valgus: A preliminary study utilizing a weight bearing extremity CT," Foot and Ankle Surgery, vol. 19, 2013, pp. 155-161.
"Futura Forefoot Implant Arthroplasty Products," Tornier, Inc., 2008, 14 pages.
"HAT-TRICK Lesser Toe Repair System, Foot and Ankle Technique Guide, Metatarsal Shortening Osteotomy Surgical Technique," Smith & Nephew, 2014, 16 pages.
"HAT-TRICK Lesser Toe Repair System," Smith & Nephew, Brochure, Aug. 2014, 12 pages.
"Hoffmann II Compact External Fixation System", Stryker, Brochure, Literature No. 5075-1-500, 2006, 12 pages.
"Hoffmann II Micro Lengthener", Stryker, Operative Technique, Literature No. 5075-2-002, 2008, 12 pages.
"Hoffmann Small System External Fixator Orthopedic Instruments," Stryker, retrieved Dec. 19, 2014, from the Internet: <http://www.alibaba.com/product-detail/Stryker-Hoffmann-Small-System-External-Fixator_1438850129.html>, 3 pages.
Patient to Patient Precision, Accu-Cut, Osteotomy Guide System, BioPro, Foot & Ankle International Journal, vol. 23, No. 8, Aug. 2002, 2 pages.
Blomer "Problems and complications of knee endoprostheses from a manufacturer's point of view" Orthopade 200, 29, pp. 688-696, English Abstract.
"Prophecy Inbone Preoperative Navigation Guides", Wright Medical Technology, Inc., Nov. 2013, 6 pages.
"Rayhack Ulnar Shortening Generation II Low-Profile Locking System Surgical Technique," Wright Medical Technology, Inc., Dec. 2013, 20 pages.
Smith & Nephew scores a HAT-TRICK with its entry into the high-growth hammer toe repair market, Smith & Nephew, Jul. 31, 2014, 2 pages.
"Lag Screw Target Bow," Stryker Leibinger GmbH & Co. KG, Germany 2004, 8 pages.
Anderson et al, "Uncemented STAR Total Ankle Protheses" Journal of Bone Joint Surgery America, Sep. 2004, Abstract of Article, pp. 6.
Coetzee et al., "The Lapidus Procedure: A Prospective Cohort Outcome Study," Foot & Ankle International, vol. 25, No. 8, Aug. 2004, pp. 526-531.
Claim Chart for Fishco, "A Straightforward Guide to the Lapidus Bunionectomy," HMP Global (Sep. 6, 2013), Exhibit B2 of Defendant Fusion Orthopedics LLC's Invalidity Contentions, No. CV-22-00490-PHX-SRB, US District Court for the District of Arizona, Aug. 27, 2022, 67 pages.
Claim Chart for Fishco, "Making the Lapidus Easy," The Podiatry Institute (Apr. 2014), Exhibit B1 of Defendant Fusion Orthopedics LLC's Invalidity Contentions, No. CV-22-00490-PHX-SRB, US District Court for the District of Arizona, Aug. 27, 2022, 97 pages.
Claim Chart for Groves Public Use (Mar. 26, 2014), Exhibit B4 of Defendant Fusion Orthopedics LLC's Invalidity Contentions, No. CV-22-00490-PHX-SRB, US District Court for the District of Arizona, Aug. 27, 2022, 161 pages.
Claim Chart for Groves, "Functional Position Joint Sectioning: Pre-Load Method for Lapidus Arthrodesis," Update 2015: Proceedings of the Annual Meeting of the Podiatry Institute, Chpt. 6, pp. 23-29 (Apr. 2015), Exhibit B3 of Defendant Fusion Orthopedics LLC's Invalidity Contentions, No. CV-22-00490-PHX-SRB, US District Court for the District of Arizona, Aug. 27, 2022, 151 pages.
Claim Chart for Mote, "First Metatarsal-Cuneiform Arthrodesis for the Treatment of First Ray Pathology: A Technical Guide," The Journal Foot & Ankle Surgery (Sep. 1, 2009), Exhibit B5 of Defendant Fusion Orthopedics LLC's Invalidity Contentions, No. CV-22-00490-PHX-SRB, US District Court for the District of Arizona, Aug. 27, 2022, 21 pages.
Claim Chart for U.S. Pat. No. 10,376,268 to Fallin et al., entitled "Indexed Tri-Planar Osteotomy Guide and Method," issued Aug. 13, 2019, Exhibit B6 of Defendant Fusion Orthopedics LLC's Invalidity Contentions, No. CV-22-00490-PHX-SRB, US District Court for the District of Arizona, Aug. 27, 2022, 155 pages.
Claim Chart for U.S. Pat. No. 8,282,645 to Lawrence et al., entitled "Metatarsal Bone Implant Cutting Guide," issued Jan. 18, 2010, Exhibit B7 of Defendant Fusion Orthopedics LLC's Invalidity Contentions, No. CV-22-00490-PHX-SRB, US District Court for the District of Arizona, Aug. 27, 2022, 76 pages.
Claim Chart for U.S. Pat. No. 9,452,057 to Dacosta et al., entitled "Bone Implants and Cutting Apparatuses and Methods," issued Apr. 8, 2011, Exhibit B8 of Defendant Fusion Orthopedics LLC's Invalidity Contentions, No. CV-22-00490-PHX-SRB, US District Court for the District of Arizona, Aug. 27, 2022, 110 pages.
D'Amico et al., "Motion of the First Ray: Clarification Through Investigation," Journal of the American Podiatry Association, vol. 69, No. 1, Jan. 1979, pp. 17-23.
Dayton et al., "Biwinged Excision for Round Pedal Lesions," The Journal of Foot and Ankle Surgery, vol. 35, No. 3, 1996, pp. 244-249.
Coughlin "Proximal Metatarsal Osteotomy and Distal Soft Tissue Reconstruction for Hallux Valgus in Juveniles" Orthopaedics and Traumatology, vol. 7, Published: Jun. 1999, pp. 133-143.
Dayton et al., "Medial Incision Approach to the First Metatarsophalangeal Joint," The Journal of Foot and Ankle Surgery, vol. 40, No. 6, Nov./Dec. 2001, pp. 414-417.
Dayton et al., "Reduction of the Intermetatarsal Angle after First Metatarsophalangeal Joint Arthrodesis in Patients with Moderate and Severe Metatarsus Primus Adductus," The Journal of Foot and Ankle Surgery, vol. 41, No. 5, Sep./Oct. 2002, pp. 316-319.
Dayton et al., "Use of the Z Osteotomy for Tailor Bunionectomy," The Journal of Foot and Ankle Surgery, vol. 42, No. 3, May/Jun. 2003, pp. 167-169.
Dayton et al., "Early Weightbearing After First Metatarsophalangeal Joint Arthrodesis: A Retrospective Observational Case Analysis," The Journal of Foot and Ankle Surgery, vol. 43, No. 3, May/Jun. 2004, pp. 156-159.
Dayton et al., "Dorsal Suspension Stitch: An Alternative Stabilization After Flexor Tenotomy for Flexible Hammer Digit Syndrome," The Journal of Foot and Ankle Surgery, vol. 48, No. 5, Sep./Oct. 2009, pp. 602-605.
Dayton et al., "The Extended Knee Hemilithotomy Position for Gastrocnemius Recession," The Journal of Foot and Ankle Surgery, vol. 49, 2010, pp. 214-216.

(56) References Cited

OTHER PUBLICATIONS

Dayton et al., "A User-Friendly Method of Pin Site Management for External Fixators," Foot and Ankle Specialist, Sep. 16, 2011, 4 pages.
Dayton et al., "Hallux Varus as Complication of Foot Compartment Syndrome," The Journal of Foot and Ankle Surgery, vol. 50, 2011, pp. 504-506.
Dayton et al., "Measurement of Mid-Calcaneal Length on Plain Radiographs: Reliability of a New Method," Foot and Ankle Specialist, vol. 4, No. 5, Oct. 2011, pp. 280-283.
Cottom, "Fixation of the Lapidus Arthrodesis with a Plantar Interfragmentary Screw and Medial Low Profile Locking Plate," The Journal of Foot & Ankle Surgery, vol. 51, 2012, pp. 517-522.
Dayton et al., "Does Postoperative Showering or Bathing of a Surgical Site Increase the Incidence of Infection? A Systematic Review of the Literature," The Journal of Foot and Ankle Surgery, vol. 52, 2013, pp. 612-614.
Dayton et al., "Effectiveness of a Locking Plate in Preserving Midcalcaneal Length and Positional Outcome after Evans Calcaneal Osteotomy: A Retrospective Pilot Study," The Journal of Foot and Ankle Surgery, vol. 52, 2013, pp. 710-713.
Dayton et al., "Principles of Management of Growth Plate Fractures in the Foot and Ankle," Clinics in Podiatric Medicine and Surgery, Pediatric Foot Deformities, Oct. 2013, 17 pages.
Crawford et al. "Metatarsus Adductus: Radiographic and Pathomechanical Analysis" Chapter 5, https://www.podiatryinstitute.com/pdfs/Update_2014/2014_05.pdf, Published 2014, pp. 25-30.
Dayton et al., "Clarification of the Anatomic Definition of the Bunion Deformity," The Journal of Foot and Ankle Surgery, vol. 53, 2014, pp. 160-163.
Dayton et al., "Observed Changes in First Metatarsal and Medial Cuneiform Positions after First Metatarsophalangeal Joint Arthrodesis," The Journal of Foot and Ankle Surgery, vol. 53, 2014, pp. 32-35.
Dayton et al., "Observed Changes in Radiographic Measurements of the First Ray after Frontal Plane Rotation of the First Metatarsal in a Cadaveric Foot Model," The Journal of Foot and Ankle Surgery, Article in Press, 2014, 5 pages.
Dayton et al., "Observed Changes in Radiographic Measurements of the First Ray after Frontal and Transverse Plane Rotation of the Hallux: Does the Hallux Drive the Metatarsal in a Bunion Deformity?," The Journal of Foot and Ankle Surgery, Article in Press, 2014, 4 pages.
Dayton et al., "Observed Changes in Radiographic Measurements of the First Ray after Frontal and Transverse Plane Rotation of the Hallux: Does the Hallux Drive the Metatarsal in a Bunion Deformity?," The Journal of Foot and Ankle Surgery, vol. 53, 2014, pp. 584-587.
Dayton et al., "Reduction of the Intermetatarsal Angle after First Metatarsal Phalangeal Joint Arthrodesis: A Systematic Review," The Journal of Foot and Ankle Surgery, Article in Press, 2014, 4 pages.
Dayton et al., "Technique for Minimally Invasive Reduction of Calcaneal Fractures Using Small Bilateral External Fixation," The Journal of Foot and Ankle Surgery, Article in Press, 2014, 7 pages.
Dayton, "Tarsal-Metatarsal Joint: Primary & Revision Arthrodesis" Disclosure: Speaker for Orthofix and Biomet, Apr. 2014, pp. 38.
Dalat et al. "Does arthrodesis of the first metatarsophalangeal joint correct the intermetatarsal M1M2 angle? Analysis of a continuous series of 208 arthrodeses fixed with plates" Orthopaedics & Traumatology: Surgery & Research 101, 2015, pp. 709-714.
Dayton et al., "A new triplanar paradigm for bunion management," Lower Extremity Review, Apr. 2015, 9 pages.
Dayton et al., "Comparison of Complications for Internal and External Fixation for Charcot Reconstruction: A Systematic Review," The Journal of Foot and Ankle Surgery, Article in Press, 2015, 4 pages.
Dayton et al., "Complications of Metatarsal Suture Techniques for Bunion Correction: A Systematic Review of the Literature," The Journal of Foot and Ankle Surgery, Article in Press, 2015, 3 pages.
Dayton et al., "Is Our Current Paradigm for Evaluation and Management of the Bunion Deformity Flawed? A Discussion of Procedure Philosophy Relative to Anatomy," The Journal of Foot and Ankle Surgery, vol. 54, 2015, pp. 102-111.
Dayton et al., "Quantitative Analysis of the Degree of Frontal Rotation Required to Anatomically Align the First Metatarsal Phalangeal Joint During Modified Tarsal-Metatarsal Arthrodesis Without Capsular Balancing," The Journal of Foot and Ankle Surgery, 2015, pp. 1-6.
Dayton et al. "Comparison of Tibial Sesamoid Position on Anteroposterior and Axial Radiographs Before and After Triplane Tarsal Metatarsal Joint Arthrodesis" The Journal of Foot & Ankle Surgery 56, 2017, pp. 1041-1046.
Dayton "Evidence-Based Bunion Surgery: A Critical Examination of Current and Emerging Concepts and Techniques" Springer International Publishing, 2017, pp. 254.
Dayton et al. "Biomechanical Characteristics of Biplane Multiplanar Tension-Side Fixation for Lapidus Fusion" The Journal of Foot & Ankle Surgery, 2018, pp. 1-5.
Dayton et al. "Progression of Healing on Serial Radiographs Following First Ray Arthrodesis in the Foot Using a Biplanar Plating Technique Without Compression" The Journal of Foot & Ankle Surgery, 2018, pp. 1-7.
Cruz et al., "Does Hallux Valgus Exhibit a Deformity Inherent to the First Metatarsal Bone?" The Journal of Foot & Ankle Surgery, vol. 58, No. 6, Nov. 2019, pp. 1210-1214.
Dahlgren et al., "First Tarsometatarsal Fusion Using Saw Preparation vs. Standard Preparation of the Joint: A Cadaver Study," Foot & Ankle Orthopaedics, vol. 4, No. 4, Oct. 2019, 2 pages.
Conti et al., "Effect of the Modified Lapidus Procedure for Hallux Valgus on Foot Width," Foot & Ankle International, Feb. 1, 2020, published online: Oct. 30, 2019, 6 pages.
Conti et al., "Effect of the Modified Lapidus Procedure on Pronation of the First Ray in Hallux Valgus," Foot & Ankle International, Feb. 1, 2020, published online: Oct. 16, 2019, 8 pages.
Dayton et al. "Comparison of Radiographic Measurements Before and After Triplane Tarsometatarsal Arthrodesis for Hallux Valgus" The Journal of Foot & Ankle Surgery 59, 2020, pp. 291-297.
Curran et al. "Functional Capabilities After First Metatarsal Phalangeal Joint Arthrodesis Using a Locking Plate and Compression Screw Construct" The Journal of Foot & Ankle Surgery, 2021, pp. 1-5.
De Carvalho, et al. "Automated Three-dimensional distance and coverage mapping of hallux valgus: a case-control study" Journal of Foot and Ankle, 2022; 16(1), pp. 5.
Dayton et al., "Comparison of the Mechanical Characteristics of a Universal Small Biplane Plating Technique Without Compression Screw and Single Anatomic Plate With Compression Screw," The Journal of Foot & Ankle Surgery, vol. 55, No. 3, May/Jun. 2016, published online: Feb. 9, 2016, pp. 567-571.
Dayton et al., "Relationship of Frontal Plane Rotation of First Metatarsal to Proximal Articular Set Angle and Hallux Alignment in Patients Undergoing Tarsometatarsal Arthrodesis for Hallux Abducto Valgus: A Case Series and Critical Review of the Literature," The Journal of Foot & Ankle Surgery, 2013, Article in Press, Mar. 1, 2013, 7 pages.
Dayton et al., "Relationship Of Frontal Plane Rotation Of First Metatarsal To Proximal Articular Set Angle And Hallux Alignment In Patients Undergoing Tarsometatarsal Arthrodesis For Hallux Abducto Valgus: A Case Series And Critical Review Of The Literature," The Journal of Foot and Ankle Surgery, vol. 52, No. 3, May/Jun. 2013, pp. 348-354.
De Geer et al., "A New Measure of Tibial Sesamoid Position in Hallux Valgus in Relation to the Coronal Rotation of the First Metatarsal in CT Scans," Foot and Ankle International, Mar. 26, 2015, 9 pages.
De Heer et al., "Procedure-Specific Hardware Removal After Evans Osteotomy" Journal of the American Podiatric Medical Association, vol. 110, No. 2, Mar./Apr. 2020, pp. 1-7.
DeCarbo et al., "Locking Plates: Do They Prevent Complications?," Podiatry Today, Apr. 2014, 7 pages.
DeCarbo et al., "Resurfacing Interpositional Arthroplasty for Degenerative Joint Disease of the First Metatarsalphalangeal Joint," Podiatry Management, Jan. 2013, pp. 137-142.

(56) References Cited

OTHER PUBLICATIONS

Wendl et al., "Navigation in der Knieendoprothetik," OP-Journal, vol. 17, 2002, pp. 22-27, including English Abstract.
Whipple et al., "Zimmer Herbert Whipple Bone Screw System: Surgical Techniques for Fixation of Scaphoid and Other Small Bone Fractures," Zimmer, 2003, 59 pages.
Weber et al., "A Simple System For Navigation Of Bone Alignment Osteotomies Of The Tibia," International Congress Series, vol. 1268, Jan. 2004, pp. 608-613, (Abstract Only).
Wukich et al., "Hypermobility of the First Tarsometatarsal Joint," Foot and Ankle Clinics, vol. 10, No. 1, Mar. 2005, pp. 157-166.
Weber et al., "Use of the First Ray Splay Test to Assess Transverse Plane Instability Before First Metatarsocuneiform Fusion," The Journal of Foot and Ankle Surgery, vol. 45, No. 4, Jul./Aug. 2006, pp. 278-282.
Vitek et al., "Die Behandlung des Hallux rigidus mit Cheilektomie und Akin-Moberg-Osteotomie unter Verwendung einer neuen Schnittlehre und eines neuen Schraubensystems," Orthopadische Praxis, vol. 44, Nov. 2008, pp. 563-566, including English Abstract on p. 564.
Vitek, "Neue Techniken in der Fuchirurgie Das V-tek-System," ABW Wissenschaftsverlag GmbH, 2009, 11 pages, including English Abstract.
Yakacki et al. "Compression Forces of Internal and External Ankle Fixation Devices with Simulated Bone Resorption," Foot and Ankle International, vol. 31, No. 1, Jan. 2010, pp. 76-85, (Abstract Only).
Weil et al., "Anatomic Plantar Plate Repair Using the Weil Metatarsal Osteotomy Approach," Foot & Ankle Specialist, vol. 4, No. 3, 2011, pp. 145-150.
Wienke et al., "Bone Stimulation For Nonunions: What the Evidence Reveals," Podiatry Today, vol. 24, No. 9, Sep. 2011, pp. 52-57.
Williams et al., "Metatarsus adductus: Development of a non-surgical treatment pathway," Journal of Paediatrics and Child Health, vol. 49, 2013, pp. E428-433.
Yasuda et al., "Proximal Supination Osteotomy of the First Metatarsal for Hallux Valgus," Foot and Ankle International, vol. 36, No. 6, Jun. 2015, pp. 696-704.
Walker et al., "The Role of First Ray Insufficiency in the Development of Metatarsalgia," Foot and Ankle Clinics, vol. 24, No. 4, Dec. 2019, published online: Sep. 5, 2019, pp. 641-648.
Weigelt et al., "Risk Factors for Nonunion After First Metatarsophalangeal Joint Arthrodesis With a Dorsal Locking Plate and Compression Screw Construct: Correction of Hallux Valgus Is Key," The Journal of Foot & Ankle Surgery, vol. 60, No. 6, Nov./Dec. 2021, pp. 1179-1183.
Wright Medical, "How Blueprint Works—from CT to 3D [CAW-9389]", https://www.wrightmeded.com/videos/how-blueprint-works-from-ct-to-3d-caw-9389, video time mark 32 seconds to 48 seconds, Dated May 26, 2022.
International Searching Authority, "International Search Report and Written Opinion", From Application No. PCT/US2023/33733, Mailed Feb. 14, 2024, pp. 9.
Hunt et al., "Locked Versus Nonlocked Plate Fixation For Hallux MTP Arthrodesis," Foot and Ankle International, vol. 32, No. 7, Jul. 2011, pp. 704-709.
Integra, "Integra Large Qwix Positioning and Fixation Screw, Surgical Technique," 2012, 16 pages.
Jackson III et al., "The Surgical Learning Curve for Modified Lapidus Procedure for Hallux Valgus Deformity," Foot & Ankle Specialist, Jul. 2021, 5 pages.
Jeuken et al., "Long-term Follow-up of a Randomized Controlled Trial Comparing Scarf to Chevron Osteotomy in Hallux Valgus Correction," Foot & Ankle International, vol. 37, No. 7, 2016, pp. 687-695.
Kilmartin et al., "Combined rotation scarf and Akin osteotomies for hallux valgus: a patient focused 9 year follow up of 50 patients," Journal of Foot and Ankle Research, vol. 3, No. 2, 2010, 12 pages.
Kim et al., "A Multicenter Retrospective Review of Outcomes for Arthrodesis, Hemi-Metallic Joint Implant, and Resectional Arthroplasty in the Surgical Treatment of End-Stage Hallux Rigidus," The Journal of Foot and Ankle Surgery, vol. 51, 2012, pp. 50-56.
Kim et al., "A New Measure of Tibial Sesamoid Position in Hallux Valgus in Relation to the Coronal Rotation of the First Metatarsal in CT Scans," Foot and Ankle International, vol. 36, No. 8, 2015, pp. 944-952.
Klos et al., "Modified Lapidus arthrodesis with plantar plate and compression screw for treatment of hallux valgus with hypermobility of the first ray: A preliminary report," Foot and Ankle Surgery, vol. 19, 2013, pp. 239-244.
KLS Martin Group, "Individual Patient Solutions IPS Implants", https://www.klsmartin.com/en-na/products/individual-patient-solutions/ips-implants/, Downloaded: Jun. 1, 2022, pp. 8.
Kurup et al., "Midfoot arthritis—current concepts review," Journal of Clinical Orthopaedics and Trauma, vol. 11, 2020, pp. 399-405.
La Reaux et al., "Metatarsus adductus and hallux abducto valgus: their correlation," The Journal of Foot Surgery, vol. 26, No. 4, Jul. 1987, pp. 304-308, Abstract Only.
Langan et al., "Maintenance of Correction of the Modified Lapidus Procedure With a First Metatarsal to Intermediate Cuneiform Cross-Screw Technique," Foot & Ankle International, vol. 41, No. 4, Apr. 1, 2020, published online: Dec. 26, 2019, pp. 426-436.
Lapidus, "The Author's Bunion Operation From 1931 to 1959," Clinical Orthopaedics, vol. 16, 1960, pp. 119-135.
Latif et al., "First metatarsophalangeal fusion using joint specific dorsal plate with interfragmentary screw augmentation: Clinical and radiological outcomes," Foot and Ankle Surgery, vol. 25, 2019, pp. 132-136.
Le et al., "Tarsometatarsal Arthrodesis," Operative Techniques in Foot and Ankle Surgery, Section II, Chapter 40, 2011, pp. 281-285.
Lee et al., "Technique Tip: Lateral Soft-Tissue Release for Correction of Hallux Valgus Through a Medial Incision Using A Dorsal Flap Over the First Metatarsal," Foot & Ankle International, vol. 28, No. 8, Aug. 2007, pp. 949-951.
Li et al., "Evolution of Thinking of the Lapidus Procedure and Fixation," Foot and Ankle Clinics, vol. 25, No. 1, Mar. 2020, published online: Dec. 16, 2019, pp. 18 pages.
Lieske et al., "Implantation einer Sprunggelenktotalendo-prothese vom Typ Salto 2," Operative Orthopdie und Traumatologie, vol. 26, No. 4, 2014, pp. 401-413, including English Abstract on p. 403.
Little, "Joint Arthrodesis For Hallux Valgus," Clinics in Podiatric Medicine and Surgery, Hallux Abducto Valgus Surgery, updated Apr. 19, 2014, retrieved online from < https://www.footankleinstitute.com/first-metatarsophalangeal-joint-arthrodesis-in-the-treatment-of-hallux-valgus>, 7 pages.
Lopez et al., "Metatarsalgia: Assessment Algorithm and Decision Making," Foot and Ankle Clinics, vol. 24, No. 4, Dec. 2019, published online: Sep. 25, 2019, pp. 561-569.
MAC (Multi Axial Correction) Fixation System, Biomet Trauma, retrieved Dec. 19, 2014, from the Internet: <http://footandanklefixation.com/product/biomet-trauma-mac-multi-axial-correction-fixation-system>, 7 pages.
Machacek Jr. et al., "Salvage of a Failed Keller Resection Arthroplasty," The Journal of Bone and Joint Surgery, vol. 86A, No. 6, Jun. 2004, pp. 1131-1138.
Magin, "Computernavigierter Gelenkersatz am Knie mit dem Orthopilot," Operative Orthopdie und Traumatologie, vol. 22, No. 1, 2010, pp. 63-80, including English Abstract on p. 64.
Magin, "Die belastungsstabile Lapidus-Arthrodese bei Hallux-valgus-Deformitt mittels IVP-Plattenfixateur (V-TEK-System)," Operative Orthopdie und Traumatologie, vol. 26, No. 2, 2014, pp. 184-195, including English Abstract on p. 186.
Marshall et al., "The identification and appraisal of assessment tools used to evaluate metatarsus adductus: a systematic review of their measurement properties," Journal of Foot and Ankle Research, vol. 11, No. 25, 2018, 10 pages.
Mcaleer et al., "A systematic approach to the surgical correction of combined hallux valgus and metatarsus adductus deformities," The Journal of Foot & Ankle Surgery, May 21, 2021, 6 pages.
Mcaleer et al., "Radiographic Outcomes Following Triplanar Correction of Combined Hallux Valgus and Metatarsus Adductus Deformities," ACFAS Scientific Conference, Poster, Feb. 2022, 1 page.

(56) References Cited

OTHER PUBLICATIONS

Mccabe et al., "Anatomical reconstruction of first ray instability hallux valgus with a medial anatomical TMTJ1 plate," Foot and Ankle Surgery, vol. 27, No. 8, Dec. 2021, pp. 869-873.
Mehtar et al., "Outcomes of bilateral simultaneous hallux MTPJ fusion," Foot and Ankle Surgery, vol. 27, 2021, pp. 213-216.
Michelangelo Bunion System, Surgical Technique, "Instratek Incorporated, publication date unknown, 4 pages."
Miller et al., "Variable Angle Locking Compression Plate as Alternative Fixation for Jones Fractures: A Case Series," Kansas Journal of Medicine, vol. 12, No. 2, May 2019, pp. 28-32.
Mini Joint Distractor, Arthrex, retrieved Dec. 19, 2014, from the Internet: <http://www.arthrex.com/foot-ankle/mini-joint-distractor/products>, 2 pages.
MiniRail System, Small Bone Innovations, Surgical Technique, 2010, 24 pages.
Miyake et al., "Three-Dimensional Corrective Osteotomy for Malunited Diaphyseal Forearm Fractures Using Custom-Made Surgical Guides Based on Computer Simulation," JBJS Essential Surgical Techniques, vol. 2, No. 4, 2012, 11 pages.
Mizuno et al., "Detorsion Osteotomy of the First Metatarsal Bone in Hallux Valgus," Japanese Orthopaedic Association, Tokyo, 1956; 30:813-819.
Modular Rail System: External Fixator, Smith & Nephew, Surgical Technique, 2013, 44 pages.
Monnich et al., "A Hand Guided Robotic Planning System for Laser Osteotomy in Surgery," World Congress on Medical Physics and Biomedical Engineering vol. 25/6: Surgery, Nimimal Invasive Interventions, Endoscopy and Image Guided Therapy, Sep. 7-12, 2009, pp. 59-62, (Abstract Only).
Moore et al., "Effect Of Ankle Flexion Angle On Axial Alignment Of Total Ankle Replacement," Foot and Ankle International, vol. 31, No. 12, Dec. 2010, pp. 1093-1098, (Abstract Only).
Mortier et al., "Axial Rotation of the First Metatarsal Head in a Normal Population and Hallux Valgus Patients," Orthopaedics and Traumatology: Surgery and Research, vol. 98, 2012, pp. 677-683.
Mote et al., "First Metatarsal-Cuneiform Arthrodesis for the Treatment of First Ray Pathology: A Technical Guide," JFAS Techniques Guide, vol. 48, No. 5, Sep./Oct. 2009, pp. 593-601.
Musculoskeletal Key "Arthrodesis of the Tarsmetatarsal Joint" https://musculoskeletalkey.com/arthrodesis-of-the-tarsometatarsal-joint/, Retrieved May 8, 2020, pp. 11.
Myerson, "Cuneiform-Metatarsal Arthrodesis," The Foot and Ankle, Chapter 9, 1997, pp. 107-117.
Nagy et al., "The AO Ulnar Shortening Osteotomy System Indications and Surgical Technique," Journal of Wrist Surgery, vol. 3, No. 2, 2014, pp. 91-97.
NexFix from Nexa Orthopedics, MetaFix I from Merete Medical, Inc. and The BioPro Lower Extremities from BioPro, found in Foot & Ankle International Journal, vol. 28, No. 1, Jan. 2007, 4 pages.
Nix et al., "Prevalence of hallux valgus in the general population: a systematic review and meta-analysis," Journal of Foot and Ankle Research, vol. 3, No. 21, 2010, 9 pages.
Novastep, "Pecaplasty Percutaneous Bunion Correction" Downloaded Jun. 29, 2022, pp. 24.
Novastep, "Pecaplasty Percutaneous Bunion Correction—Brochure Pecaplasty Targeting Guide" Downloaded Dec. 15, 2021, pp. 4.
Odenbring et al., "A guide instrument for high tibial osteotomy," Acta Orthopaedica Scandinavica, vol. 60, No. 4, 1989, pp. 449-451.
Okuda et al., "Proximal Metatarsal Osteotomy for Hallux Valgus: Comparison of Outcome for Moderate and Severe Deformities," Foot and Ankle International, vol. 29, No. 7, Jul. 2008, pp. 664-670.
Instratek, "Michelangelo Bunion System, Surgical Technique", Instratek Incorporated, publication date unknown, 4 pages.
Tricot et al., "3D-corrective osteotomy using surgical guides for posttraumatic distal humeral deformity," Acta Orthopaedica Belgica, vol. 78, No. 4, 2012, pp. 538-542.
Vaida et al., "Effect on Foot Width With Triplanar Tarsometatarsal Arthrodesis for Hallux Valgus," Foot & Ankle Orthopaedics, vol. 5, No. 3, 2020, pp. 1-5.
Nyska, Synergy 3D Med, "Anatomical Model: Calcaneus", 2022, pp. 3.
Okuda et al., "Postoperative Incomplete Reduction of the Sesamoids as a Risk Factor for Recurrence of Hallux Valgus," The Journal of Bone and Joint Surgery, vol. 91-A, No. 1, Jul. 2009, pp. 1637-1645.
Okuda et al., "The Shape of the Lateral Edge of the First Metatarsal Head as a Risk Factor for Recurrence of Hallux Valgus," The Journal of Bone and Joint Surgery, vol. 89, 2007, pp. 2163-2172.
Osher et al., "Accurate Determination of Relative Metatarsal Protrusion with a Small Intermetatarsal Angle: A Novel Simplified Method," The Journal of Foot & Ankle Surgery, vol. 53, No. 5, Sep./Oct. 2014, published online: Jun. 3, 2014, pp. 548-556.
Otsuki et al., "Developing a novel custom cutting guide for curved per-acetabular osteotomy," International Orthopaedics (SICOT), vol. 37, 2013, pp. 1033-1038.
Park et al., "Comparative analysis of clinical outcomes of fixed-angle versus variable-angle locking compression plate for the treatment of Lisfranc injuries," Foot and Ankle Surgery, vol. 26, 2020, pp. 338-342.
Patel et al., "Modified Lapidus Arthrodesis: Rate of Nonunion in 227 Cases," The Journal of Foot & Ankle Surgery, vol. 43, No. 1, Jan./Feb. 2004, pp. 37-42.
Pentikainen et al., "Preoperative Radiological Factors Correlated to Long-Term Recurrence of Hallux Valgus Following Distal Chevron Osteotomy," Foot & Ankle International, vol. 35, No. 12, 2014, pp. 1262-1267.
Perler, "Cuboid Suspension in Charcot Reconstruction. Using 3D Imaging for Planning, Printing and Execution for Complex Deformity Correction" Downloaded Apr. 2021, pp. 4.
Peters et al., "Flexor Hallucis Longus Tendon Laceration as a Complication of Total Ankle Arthroplasty," Foot & Ankle International, vol. 34, No. 1, 2013, pp. 148-149.
Ray et al., "Hallux Valgus," Foot & Ankle Orthopaedics, vol. 4, No. 2, 2019, pp. 1-12.
Ray et al., "Multicenter Early Radiographic Outcomes of Triplanar Tarsometatarsal Arthrodesis With Early Weightbearing," Foot & Ankle International, vol. 40, No. 8, Aug. 1, 2019, published online: May 5, 2019, 7 pages.
Rodriguez et al., "Ilizarov method of fixation for the management of pilon and distal tibial fractures in the compromised diabetic patient: A technique guide," The Foot and Ankle Journal Online, vol. 7, No. 2, 2014, 9 pages.
Rx-Fix Mini Rail External Fixator, Wright Medical Technology, Brochure, Aug. 15, 2014, 2 pages.
Saltzman et al., "Prospective Controlled Trial of STAR Total Ankle Replacement Versus Ankle Fusion: Initial Results," Foot & Ankle International, vol. 30, No. 7, Jul. 2009, pp. 579-596.
Sammarco, "Surgical Strategies: Mau Osteotomy for Correction of Moderate and Severe Hallux Valgus Deformity," Foot & Ankle International, vol. 28, No. 7, Jul. 2007, pp. 857-864.
Sandhu et al., "Digital Arthrodesis With a One-Piece Memory Nitinol Intramedullary Fixation Device: A Retrospective Review," Foot and Ankle Specialist, vol. 6, No. 5, Oct. 2013, pp. 364-366.
Santrock et al., "Hallux Valgus Deformity and Treatment: A Three-Dimensional Approach: Lapiplasty," Foot & Ankle Clinics, vol. 23, No. 2, 2018, pp. 281-295.
Scanlan et al. "Technique Tip: Subtalar Joint Fusion Using a Parallel Guide and Double Screw Fixation," The Journal of Foot and Ankle Surgery, vol. 49, Issue 3, May-Jun. 2010, pp. 305-309, (Abstract Only).
Schon et al., "Cuneiform-Metatarsal Arthrodesis for Hallux Valgus," The Foot and Ankle, Second Edition, Chapter 8, 2002, pp. 99-117.
Scranton Jr. et al, "Anatomic Variations in the First Ray: Part I. Anatomic Aspects Related to Bunion Surgery," Clinical Orthopaedics and Related Research, vol. 151, Sep. 1980, pp. 244-255.
Shima et al., "Operative Treatment for Hallux Valgus With Moderate to Severe Metatarsus Adductus," Foot & Ankle International, vol. 40, No. 6, 2019, pp. 641-647.
Shurnas et al., "Proximal Metatarsal Opening Wedge Osteotomy," Operative Techniques in Foot and Ankle Surgery, Section I, Chapter 13, 2011, pp. 73-78.

(56) References Cited

OTHER PUBLICATIONS

Siddiqui et al. "Fixation Of Metatarsal Fracture With Bone Plate In A Dromedary Heifer," Open Veterinary Journal, vol. 3, No. 1, 2013, pp. 17-20.
Sidekick Stealth Rearfoot Fixator, Wright Medical Technology, Surgical Technique, Dec. 2, 2013, 20 pages.
Simons et al., "Short-Term Clinical Outcome of Hemiarthroplasty Versus Arthrodesis for End-Stage Hallux Rigidus," The Journal of Foot & Ankle Surgery, vol. 54, 2015, pp. 848-851.
Simpson et al., "Computer-Assisted Distraction Ostegogenesis By Ilizarov's Method," International Journal of Medical Robots and Computer Assisted Surgery, vol. 4, No. 4, Dec. 2008, pp. 310-320, (Abstract Only).
Small Bone External Fixation System, Acumed, Surgical Technique, Effective date Sep. 2014, 8 pages.
Smith et al., "Intraoperative Multiplanar Alignment System to Guide Triplanar Correction of Hallux Valgus Deformity," Techniques in Foot & Ankle Surgery, 2017, 8 pages.
Smith et al., "Opening Wedge Osteotomies for Correction of Hallux Valgus: A Review of Wedge Plate Fixation," Foot and Ankle Specialist, vol. 2, No. 6, Dec. 2009, pp. 277-282.
Smith et al., "Understanding Frontal Plane Correction in Hallux Valgus Repair," Clinics in Podiatric Medicine and Surgery, vol. 35, 2018, pp. 27-36.
Sokoloff, "Lapidus Procedure," Textbook of Bunion Surgery, Chapter 15, 1981, pp. 277-287.
Stableloc External Fixation System, Acumed, Product Overview, Effective date Sep. 2015, 4 pages.
Stahl et al., "Derotation Of Post-Traumatic Femoral Deformities By Closed Intramedullary Sawing," Injury, vol. 37, No. 2, Feb. 2006, pp. 145-151, (Abstract Only).
Stamatis et al., "Mini Locking Plate as Medial Buttress for Oblique Osteotomy for Hallux Valgus," Foot & Ankle International, vol. 31, No. 10, Oct. 2010, pp. 920-922.
Stryker, "PROstep Minimally Invasive Surgery" https://www.stryker.com/us/en/foot-and-ankle/products/prostep.html, Downloaded Jun. 23, 2023, pp. 10.
Synergy 3D Med, "Anatomical Model: Calcaneus" Downloaded Mar. 2, 2023, pp. 2.
Synopsys, "Medical Image Segmentation with Machine Learning—Simpleware Automated Solution Modules", https://www.synopsys.com/simpleware/software/auto-segmenter-modules.html#simpleware-as-ortho, 2022, pp. 12.
Talbot et al., "Assessing Sesamoid Subluxation: How Good is the AP Radiograph?," Foot and Ankle International, vol. 19, No. 8, Aug. 1998, pp. 547-554.
TempFix Spanning the Ankle Joint Half Pin and Transfixing Pin Techniques, Biomet Orthopedics, Surgical Technique, 2012, 16 pages.
Tornier Technology, "Tornier Blueprint 3D Planning + PSI", https://www.wrightemedia.com/ProductFiles/Files/PDFs/CAW-8609_EN_HR_LE.pdf, Feb. 2017, pp. 12.
Total Ankle Institute, "Prophecy: Preoperative Navigation Guides", https://www.totalankleinstitute.com/infinity-products/prophecy-preoperative-navigation-guides/, 2019, pp. 6.
Toth et al., "The Effect of First Ray Shortening in the Development of Metatarsalgia in the Second Through Fourth Rays After Metatarsal Osteotomy," Foot & Ankle International, vol. 28, No. 1, Jan. 2007, pp. 61-63.
Treace "FastGrafter Autograft Harvesting System" Downloaded from https://www.lapiplasty.com/surgeons/other-products/fastgrafter/, Dec. 4, 2024, pp. 8.
Treace Medical Concepts, "Adductoplasty Midfoot Correction System", https://www.lapiplasty.com/surgeons/other-products/adductoplasty-system/, Downloaded May 2, 2022, pp. 9.
Use for BME Speed Nitinol Staple Fixation for the Lapidus Procedure, "date unknown, 1 page."
Virzi et al. "Comprehensive Review of 3D Segmentation Software Tools for MRI Usable for Pelvic Surgery Planning", Journal of Digital Imaging (2020) 33, pp. 99-110.
Prior Art Publications, Exhibit A of Defendant Fusion Orthopedics LLC's Invalidity Contentions, No. CV-22-00490-PHX-SRB, US District Court for the District of Arizona, Aug. 27, 2022, 3 pages.
Decarbo et al., "The Weil Osteotomy: A Refresher," Techniques in Foot and Ankle Surgery, vol. 13, No. 4, Dec. 2014, pp. 191-198.
Defendant Fusion Orthopedics LLC's Invalidity Contentions, No. CV-22-00490-PHX-SRB, US District Court for the District of Arizona, Aug. 27, 2022, 41 pages.
Didomenico et al., "Correction of Frontal Plane Rotation of Sesamoid Apparatus during the Lapidus Procedure: A Novel Approach," The Journal of Foot and Ankle Surgery, vol. 53, 2014, pp. 248-251.
Didomenico et al., "Lapidus Bunionectomy: First Metatarsal-Cuneiform Arthrodesis," McGlamrys Comprehensive Textbook of Foot and Ankle Surgery, Fourth Edition, vol. 1, Chapter 31, 2013, 24 pages.
Dinapoli et al., "Metatarsal Osteotomy for the Correction of Metatarsus Adductus," Reconstructive Surgery of the Foot and Leg, 1989, pp. 242-250.
Disior, "Bonelogic Foot & Ankle Module", https://www.disior.com/foot--ankle.html, Downloaded Jun. 1, 2022, pp. 6.
Dobbe et al. "Patient-Tailored Plate For Bone Fixation And Accurate 3D Positioning In Corrective Osteotomy," Medical and Biological Engineering and Computing, vol. 51, No. 1-2, Feb. 2013, pp. 19-27, (Abstract Only).
Doty et al., "Hallux valgus and hypermobility of the first ray: facts and fiction," International Orthopaedics, vol. 37, 2013, pp. 1655-1660.
Dubovik et al., "Talonavicular Joint Arthrodesis and Medial Displacement Calcaneal Osteotomy for Treatment of Patients With Planovalgus Deformity" Traumatology and Orthopedics of Russia, vol. 18, No. 3, Sep. 30, 2012, pp. 83-88.
Easley et al., "Current Concepts Review: Hallux Valgus Part I: Pathomechanics, Clinical Assessment, and Nonoperative Management," Foot and Ankle International, vol. 28, No. 5, May 2007, pp. 654-659.
Easley et al., "Current Concepts Review: Hallux Valgus Part II: Operative Treatment," Foot and Ankle International, vol. 28, No. 6, Jun. 2007, pp. 748-758.
Easley et al., "What is the Best Treatment for Hallux Valgus?," Evidence-Based Orthopaedics—The Best Answers to Clinical Questions, Chapter 73, 2009, pp. 479-491.
EBI Extra Small Rail Fixator, Biomet Trauma, retrieved Dec. 19, 2014, from the Internet: <http://footandanklefixation.com/product/biomet-trauma-ebi-extra-small-rail-fixator>, 7 pages.
Holmes, Jr., "Correction of the Intermetatarsal Angle Component of Hallux Valgus Using Fiberwire-Attached Endo-buttons," Revista Internacional de Ciencias Podologicas, vol. 6, No. 2, 2012, pp. 73-79.
Eustace et al., "Hallux valgus, first metatarsal pronation and collapse of the medial longitudinal arch—a radiological correlation," Skeletal Radiology, vol. 23, 1994, pp. 191-194.
Fallin et al., US Provisional Application Entitled Indexed Tri-Planar Osteotomy Guide and Method, U.S. Appl. No. 62/118,378, filed Feb. 19, 2015, 62 pages.
Fazal et al., "First metatarsophalangeal joint arthrodesis with two orthogonal two hole plates," Acta Orthopaedica et Traumatologica Turcica, vol. 52, 2018, pp. 363-366.
Feilmeier et al., "Incidence of Surgical Site Infection in the Foot and Ankle with Early Exposure and Showering of Surgical Sites: A Prospective Observation," The Journal of Foot and Ankle Surgery, vol. 53, 2014, pp. 173-175.
Feilmeier et al., "Reduction of Intermetatarsal Angle after First Metatarsophalangeal Joint Arthrodesis in Patients with Hallux Valgus," The Journal of Foot and Ankle Surgery, vol. 53, 2014, pp. 29-31.
Ferrari et al., "A Radiographic Study of the Relationship Between Metatarsus Adductus and Hallux Valgus," The Journal of Foot and Ankle Surgery, vol. 42, No. 1, 2003, pp. 9-14.
Ferreyra et al., "Can we correct first metatarsal rotation and sesamoid position with the 3D Lapidus procedure?," Foot and Ankle Surgery, vol. 28, No. 3, Apr. 2022, pp. 313-318.
Fibretuff, "3D Printing, CNC Machining, Molding and Extruding Biocompatible material's with "bone like" Qualities for 3D Printing" https://fibretuff.us, Downloaded Feb. 24, 2023, pp. 22.

(56) References Cited

OTHER PUBLICATIONS

Fishco, "A Straightforward Guide To The Lapidus Bunionectomy," Podiatry Today, Retrieved online from <https://www.hmpglobal-learningnetwork.com/site/podiatry/blogged/straightforward-guide-lapidus-bunionectomy>, dated Sep. 6, 2013, 5 pages.
Fishco, "Making the Lapidus Easy," The Podiatry Institute, Update 2014, Chapter 14, 2014, pp. 91-93.
Flavin et al., "Arthrodesis of the First Metatarsophalangeal Joint Using a Dorsal Titanium Contoured Plate," Foot & Ankle International, vol. 25, No. 11, Nov. 2004, pp. 783-787.
Fleming et al., "Results of Modified Lapidus Arthrodesis Procedure Using Medial Eminence as an Interpositional Autograft," The Journal of Foot & Ankle Surgery, vol. 50, 2011, pp. 272-275.
Fraissler et al., "Treatment of hallux valgus deformity," Efort Open Reviews, vol. 1, Aug. 2016, pp. 295-302.
Fuhrmann, "Arthrodesis of the First Tarsometatarsal Joint for Correction of the Advanced Splayfoot Accompanied by a Hallux Valgus," Operative Orthopadie und Traumatologie, No. 2, 2005, pp. 195-210.
Galli et al., "Enhanced Lapidus Arthrodesis: Crossed Screw Technique With Middle Cuneiform Fixation Further Reduces Sagittal Mobility," The Journal of Foot & Ankle Surgery, vol. 54, vol. 3, May/Jun. 2015, pp. 437-440.
Garthwait, "Accu-Cut System Facilitates Enhanced Precision," Podiatry Today, vol. 18, No. 6, Jun. 2005, 6 pages.
Gerard et al., "The Modified Lapidus Procedure," Orthopedics, vol. 31, No. 3, Mar. 2008, 7 pages.
Ghali et al., "The Management of Metatarsus Adductus et Supinatus," The Journal of Bone and Joint Surgery, vol. 66-B, No. 3, May 1984, pp. 376-380.
Giannoudis et al., "Hallux Valgus Correction," Practical Procedures in Elective Orthopaedic Surgery, Pelvis and Lower Extremity, Chapter 38, 2012, 22 pages.
Gonzalez Del Pino et al., "Variable Angle Locking Intercarpal Fusion System for Four-Corner Arthrodesis: Indications and Surgical Technique," Journal of Wrist Surgery, vol. 1, No. 1, Aug. 2012, pp. 73-78.
Gotte, "Entwicklung eines Assistenzrobotersystems fr die Knieendoprothetik," Forschungsberichte, Technische Universitat Munchen, 165, 2002, 11 pages, including partial English Translation.
Gould et al., "A Prospective Evaluation of First Metatarsophalangeal Fusion Using an Innovative Dorsal Compression Plating System," The Journal of Foot & Ankle Surgery, vol. 60, 2021, pp. 891-896.
Gregg et al., "Plantar plate repair and Weil osteotomy for metatarsophalangeal joint instability," Foot and Ankle Surgery, vol. 13, 2007, pp. 116-121.
Greiner, "The Jargon of Pedal Movements," Foot & Ankle International, vol. 28, No. 1, Jan. 2007, pp. 109-125.
Grondal et al., "A Guide Plate for Accurate Positioning of First Metatarsophalangeal Joint during Fusion," Operative Orthopdie Und Traumatologie, vol. 16, No. 2, 2004, pp. 167-178 (Abstract Only).
Groves, "Functional Position Joint Sectioning: Pre-Load Method for Lapidus Arthrodesis," The Podiatry Institute, Update 2015, Chapter 6, 2015, pp. 23-29.
Groves, "Operative Report," St. Tammany Parish Hospital, Date of Procedure, Mar. 26, 2014, 2 pages.
Gutteck et al., "Comparative study of Lapidus bunionectomy using different osteosynthesis methods," Foot and Ankle Surgery, vol. 19, 2013, pp. 218-221.
Gutteck et al., "Is it feasible to rely on intraoperative X ray in correcting hallux valgus?," Archives of Orthopaedic and Trauma Surgery, vol. 133, 2013, pp. 753-755.
Hardy et al., "Observations on Hallux Valgus," The Journal of Bone and Joint Surgery, vol. 33B, No. 3, Aug. 1951,pp. 376-391.
Hatch et al., "Analysis of Shortening and Elevation of the First Ray With Instrumented Triplane First Tarsometatarsal Arthrodesis," Foot & Ankle Orthopaedics, vol. 5, No. 4, 2020, pp. 1-8.
Hatch et al., "Triplane Hallux Abducto Valgus Classification," The Journal of Foot & Ankle Surgery, vol. 57, No. 5, Sep./Oct. 2018, published online: May 18, 2018, pp. 972-981.
Hetherington et al., "Evaluation of surgical experience and the use of an osteotomy guide on the apical angle of an Austin osteotomy," The Foot, vol. 18, 2008, pp. 159-164.
Hirao et al., "Computer assisted planning and custom-made surgical guide for malunited pronation deformity after first metatarsophalangeal joint arthrodesis in rheumatoid arthritis: A case report," Computer Aided Surgery, vol. 19, Nos. 1-3, 2014, pp. 13-19.
Ho et al., "Hallux rigidus," Efort Open Reviews, vol. 2, Jan. 2017, pp. 13-20.

* cited by examiner

PATIENT-SPECIFIC SOFT TISSUE REARRANGEMENT

CROSS-REFERENCE TO RELATED APPLICATIONS

This application claims the benefit of U.S. Provisional Application No. 63/410,599, filed Sep. 27, 2022, which is hereby incorporated by reference in its entirety.

TECHNICAL FIELD

The present disclosure relates to surgical devices, systems, instruments, and methods. More specifically, the present disclosure relates to patient-specific instruments, implants, instruments, and/or methods of designing and using the same for tendon transfer and/or soft tissue rearrangement.

BACKGROUND

Various bone conditions may be corrected using surgical procedures, in which one or more tendons, ligaments, and/or bones may be cut, replaced, repositioned, reoriented, reattached, fixated and/or fused. These surgical procedures require the surgeon to accurately locate, position, deploy, and/or orient one or more osteotomy cuts, fixation guides, fixators, bone tunnels, grafts, implants, points of attachment for ends of grafts or soft tissue, and the like. Determining and locating an optimal location and trajectory for one or more steps of the surgical procedures, securing instruments to guide or assist in steps of the surgical procedures such as performing osteotomies, deploying fixation, grafts, and/or implants, and the like, can be challenging, given conventional techniques and instruments.

One of the challenges with conventional techniques is how to translate, map, or convert from a model of a patient's anatomy and/or virtual instrumentation to the real, physical world for performing a surgical procedure. Furthermore, surgical procedures can be extra challenging when working on anatomy such as bones of a patient's ankle, foot, or hand which are small in size, have unique surface configurations, landmarks, and/or deformities that called for extra accuracy and/or precision. In certain surgical procedures such as soft tissue rearrangement, one goal may be to maintain a desired alignment and/or balance of axes and/or weights using a surgical procedure. Accomplishing this goal can require extra precision and accuracy in positioning and/or orienting soft tissue and/or grafts.

Soft tissue rearrangement can include tendon transfer or ligament transfer surgical procedures. Various bone conditions may be corrected using tendon transfers, in which one or more tendons are cut, replaced, repositioned, reoriented and/or reattached. These surgical procedures include a surgeon properly locating, positioning, and/or orienting points of attachment for ends of transferred tendons or new tendons or tendon grafts. Determining and locating an optimal location and trajectory to tendon attachment can be challenging, given conventional techniques and instruments. What is needed is one or more guides to facilitate locating, aligning, orienting, planning, preparing for, initiating, and/or completing a soft tissue rearrangement. Existing solutions for guiding a soft tissue rearrangement are inadequate and error prone.

SUMMARY

The various apparatus, devices, systems, and/or methods of the present disclosure have been developed in response to the present state of the art, and in particular, in response to the problems and needs in the art that have not yet been fully solved by currently available technology.

Some implementations herein relate to an apparatus, such as a bone tunnel guide. For example, a bone tunnel guide may include a body having a superior side, an inferior side, a medial side, a lateral side, a posterior side, and an anterior side. The bone tunnel guide may also include a trajectory port that extends through the body, the trajectory port configured to guide a tool for forming a bone tunnel in a bone of a patient, the trajectory port defined at least partially based on a bone model of at least a portion of the bone, the bone model based on medical imaging the bone of the patient. The bone tunnel guide may furthermore include a bone engagement feature that extends from the body, the bone engagement feature configured to engage at least a portion of the bone such that the bone engagement feature positions the bone tunnel guide in a position that corresponds to a modeled position of a bone tunnel guide model engaging a bone model.

The described implementations may also include one or more of the following features. A bone tunnel guide where at least one aspect of the bone tunnel guide is configured based at least partially on user directions provided before the bone tunnel guide is fabricated. A bone tunnel guide where the bone engagement feature may include at least one patient-specific aspect unique to the patient. A bone tunnel guide where the patient-specific aspect may include a bone engagement surface on a bone-facing surface of the bone engagement feature, the bone engagement surface configured to engage at least one landmark of the bone of the patient. A bone tunnel guide where the bone engagement surface corresponds to a surface of the bone such that bone tunnel guide provides haptic feedback to a user when the bone tunnel guide translates to the position corresponding to the modeled position of the bone tunnel guide model engaging the bone model. A bone tunnel guide may include a plurality of bone engagement features, each extending away from the trajectory port. A bone tunnel guide where a number of bone engagement features of the plurality of bone engagement features is directly proportional to a number of landmark configurations near, or at, the modeled position of the bone tunnel guide model engaging the bone model. A bone tunnel guide where a number of bone engagement features of the plurality of bone engagement features is determined at least partially by user directions. A bone tunnel guide may include: a handle configured to secure the bone tunnel guide in place for formation of a bone tunnel by way of the trajectory port. A bone tunnel guide where the handle may include a shaft having a proximal end and a distal end, the distal end having a coupler having external threads configured to engage internal threads formed in the body. A bone tunnel guide where the trajectory port may include a port body that extends away from the body, the port body having a length that enables a user to grasp the port body to secure the bone tunnel guide in place for formation of a bone tunnel by way of the trajectory port. A bone tunnel guide may include a bone engagement surface on at least part of the inferior side of the body, the bone engagement surface defined at least partially based on the bone model. A bone tunnel guide may include a landmark registration feature configured to engage a landmark of the bone. A bone tunnel guide where a configuration of the bone engagement feature is directly proportional to a landmark configuration of the bone indicated on the bone model. A bone tunnel guide where the bone tunnel guide is fabricated from one of a polymer and metal.

Some implementations herein relate to a system. For example, a tendon transfer system may include a tendon trajectory guide having: a body having a superior side, an inferior side, a medial side, a lateral, a posterior side, and an anterior side; a trajectory port that extends through the body, the trajectory port configured to guide a tool for forming a bone tunnel in a foot bone of a patient, the trajectory port defined at least partially on a bone model of at least a portion of the foot bone, the bone model based on medical imaging of the foot bone of the patient; and a bone engagement surface on the inferior side of the body, the bone engagement surface configured to engage a surface of the foot bone such that the bone engagement surface positions the tendon trajectory guide at a desired position on the foot bone.

A Tendon transfer system may also include an inserter having: a proximal end; a distal end; an elongated body between the proximal end and the distal end; and where the distal end may include a point and the proximal end may include an opening System may furthermore include a handle having a first coupler configured to removably engage with a second coupler connected to the tendon trajectory guide.

The described implementations may also include one or more of the following features. A tendon transfer system may include a plurality of appendages that extend laterally from the body, each appendage having an appendage inferior surface and having a bone engagement surface on the appendage inferior surface.

Some implementations herein relate to a method for generating a patient-specific tendon transfer anchor guide for remediating a bone condition present in a patient's foot. For example, a method may include receiving an order for a patient-specific tendon transfer anchor guide for a particular soft tissue transfer surgical procedure, the patient-specific tendon transfer anchor guide having: a body having a superior side, an inferior side, a medial side, a lateral, a posterior side, and an anterior side; a trajectory port that extends through the body, the trajectory port configured to guide a tool for forming a bone tunnel in a foot bone of a patient; a bone engagement surface on the inferior side of the body, the bone engagement surface configured to engage a surface of the foot bone such that the bone engagement surface positions the patient-specific tendon transfer anchor guide at a position on the foot bone that satisfies a desired position for a bone tunnel in the foot bone; an appendage that extends laterally from the body, the appendage having an appendage inferior surface; and where the bone engagement surface extends across at least a portion of the inferior side of the body and at least a portion of the appendage inferior surface.

A method may also include preparing a draft design of the patient-specific tendon transfer anchor guide, the draft design defined based at least partially on a bone model of at least a portion of a foot bone of the patient, the bone model based on medical imaging of a patient's foot. A method may furthermore include sharing the draft design with a user of the patient-specific tendon transfer anchor guide. A method may in addition include fabricating the patient-specific tendon transfer anchor guide based on the draft design.

The described implementations may also include one or more of the following features. A method may include revising the draft design based at least partially on user directions and fabricating the patient-specific tendon transfer anchor guide in response to approval of the draft design by the user. A method may include where revising further may include adding a second appendage extending from the patient-specific tendon transfer anchor guide, the second appendage having an appendage inferior surface that may include at least a portion of the bone engagement surface.

BRIEF DESCRIPTION OF THE DRAWINGS

The advantages, nature, and additional features of exemplary embodiments of the disclosure will become more fully apparent from the following description and appended claims, taken in conjunction with the accompanying drawings. Understanding that these drawings depict only exemplary embodiments and are, therefore, not to be considered limiting of the disclosure's scope, the exemplary embodiments of the disclosure will be described with additional specificity and detail through use of the accompanying drawings.

DETAILED DESCRIPTION

Figure 1A:
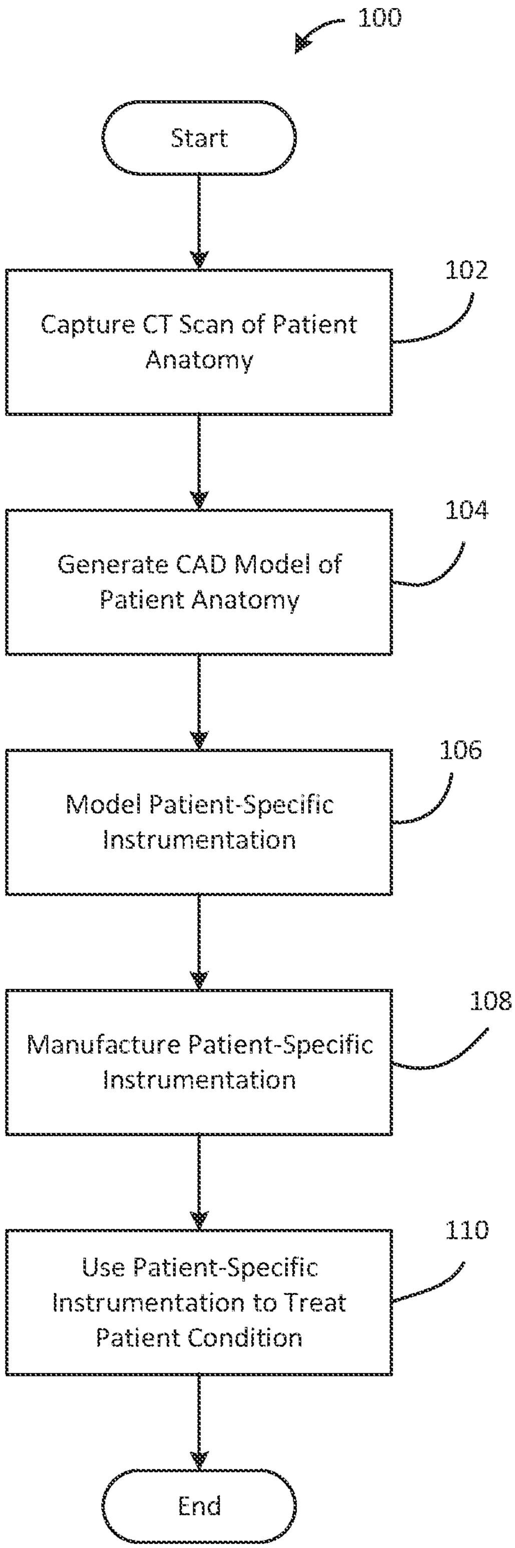
FIG. 1A is a flowchart diagram depicting a method for remediating a condition, according to one embodiment.

Exemplary embodiments of the disclosure will be best understood by reference to the drawings, wherein like parts are designated by like numerals throughout. It will be readily understood that the components, as generally described and illustrated in the Figures herein, could be arranged and designed in a wide variety of different configurations. Thus, the following more detailed description of the embodiments of the apparatus, system, and method is not intended to limit the scope of the disclosure but is merely representative of exemplary embodiments.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature can pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Standard medical planes of reference and descriptive terminology are employed in this disclosure. While these terms are commonly used to refer to the human body, certain terms are applicable to physical objects in general. A standard system of three mutually perpendicular reference planes is employed. A sagittal plane divides a body into right and left portions. A coronal plane divides a body into anterior and posterior portions. A transverse plane divides a body into superior and inferior portions. A mid-sagittal, mid-coronal, or mid-transverse plane divides a body into equal portions, which may be bilaterally symmetric. The intersection of the sagittal and coronal planes defines a superior-inferior or cephalad-caudal axis. The intersection of the sagittal and transverse planes defines an anterior-posterior axis. The intersection of the coronal and transverse planes defines a medial-lateral axis. The superior-inferior or cephalad-caudal axis, the anterior-posterior axis, and the medial-lateral axis are mutually perpendicular.

Anterior means toward the front of a body. Posterior means toward the back of a body. Superior or cephalad means toward the head. Inferior or caudal means toward the feet or tail. Medial means toward the midline of a body, particularly toward a plane of bilateral symmetry of the body. Lateral means away from the midline of a body or away from a plane of bilateral symmetry of the body. Axial means toward a central axis of a body. Abaxial means away from a central axis of a body. Ipsilateral means on the same side of the body. Contralateral means on the opposite side of the body from the side which has a particular condition or structure. Proximal means toward the trunk of the body. Proximal may also mean toward a user, viewer, or operator. Distal means away from the trunk. Distal may also mean away from a user, viewer, or operator. Dorsal means toward the top of the foot or other body structure. Plantar means toward the sole of the foot or toward the bottom of the body structure.

Antegrade means forward moving from a proximal location/position to a distal location/position or moving in a forward direction. Retrograde means backward moving from a distal location/position to a proximal location/position or moving in a backwards direction. Sagittal refers to a midline of a patient's anatomy, which divides the body into left or right halves. The sagittal plane may be in the center of the body, splitting it into two halves. Prone means a body of a person lying face down. Supine means a body of a person lying face up.

As used herein, "coupling", "coupling member", or "coupler" refers to a mechanical device, apparatus, member, component, system, assembly, or structure, that is organized, configured, designed, arranged, or engineered to connect, or facilitate the connection of, two or more parts, objects, or structures. In certain embodiments, a coupling can connect adjacent parts or objects at their ends. In certain embodiments, a coupling can be used to connect two shafts together at their ends for the purpose of transmitting power. In other embodiments, a coupling can be used to join two pieces of rotating equipment while permitting some degree of misalignment or end movement or both. In certain embodiments, couplings may not allow disconnection of the two parts, such as shafts during operation. (Search "coupling" on Wikipedia.com Jul. 26, 2021. CC-BY-SA 3.0 Modified. Accessed Jul. 27, 2021.) A coupler may be flexible, semi-flexible, pliable, elastic, or rigid. A coupler may join two structures either directly by connecting directly to one structure and/or directly to the other or indirectly by connecting indirectly (by way of one or more intermediary structures) to one structure, to the other structure, or to both structures.

"Patient specific" refers to a feature, an attribute, a characteristic, a structure, function, structure, device, guide, tool, instrument, apparatus, member, component, system, assembly, module, or subsystem or the like that is adjusted, tailored, modified, organized, configured, designed, arranged, engineered, and/or fabricated to specifically address the anatomy, physiology, condition, abnormalities, needs, or desires of a particular patient or surgeon serving the particular patient. In one aspect, a patient specific attribute or feature is unique to a single patient and may include features unique to the patient such as a number of cut channels, a number of bone attachment features, a number of bone engagement surfaces, a number of resection features, a depth of one or more cutting channels, an angle for one or more resection channels, a surface contour, component position, component orientation, a trajectory for an instrument, implant, or anatomical part of a patient, a lateral offset, and/or other features.

"Patient-specific instrument" refers to an instrument, implant, or guide designed, engineered, and/or fabricated for use with a specific patient. In one aspect, a patient-specific instrument is unique to a patient and may include features unique to the patient such as a surface contour or other features.

"Patient-specific positioning guide" or "Patient-specific positioner" refers to an instrument, implant, positioner, structure, or guide designed, engineered, and/or fabricated for use as a positioner with a specific patient. In one aspect, a patient-specific positioning guide is unique to a patient and may include features unique to the patient such as patient-specific offsets, translation distances, openings, angles, orientations, anchor a surface contour or other features.

"Patient-specific cutting guide" refers to a cutting guide designed, engineered, and/or fabricated for use with a specific patient. In one aspect, a patient-specific cutting guide is unique to a patient and may include features unique to the patient such as a surface contour or other features.

"Patient-specific resection guide" refers to a guide designed, engineered, and/or fabricated for use in resection for a specific patient. In one aspect, a patient-specific resection guide is unique to a patient and may include features unique to the patient such as a surface contour or other features.

"Patient-specific trajectory guide" refers to a trajectory guide designed, engineered, and/or fabricated for use with a specific patient. In one aspect, a patient-specific trajectory guide is unique to a single patient and may include features unique to the patient such as a surface contour or other features.

"Patient specific instrument" (PSI) refers to a structure, device, guide, tool, instrument, apparatus, member, component, system, assembly, module, or subsystem that is adjusted, tailored, modified, organized, configured, designed, arranged, engineered, and/or fabricated to specifically address the anatomy, physiology, condition, abnormalities, needs, or desires of a particular patient. In certain aspects, one patient. In one aspect, a patient specific instrument is unique to a single patient and may include features unique to the patient such as a surface contour, component position, component orientation, and/or other features. In other aspects, one patient specific instrument may be useable with a number of patients having a particular class of characteristics.

As used herein, "tunnel" refers to a duct, an opening, a void, a passage, or other channel in a body or structure of an apparatus, instrument, structure, part, bone, member, device, component, system, or assembly. In certain embodiments, a tunnel is narrower and longer than the tunnel is wide. A tunnel can have a variety of shapes and/or cross-sections and may be straight or include curves or bends. In certain embodiments, a tunnel may have a circular cross section. In certain embodiments, a tunnel may extend partially into, or wholly through a body or structure. Where a tunnel extends partially into a body or structure, the tunnel may also be referred to as an opening, a cave, or the like.

As used herein, an "indicator" refers to an apparatus, device, component, system, assembly, mechanism, hardware, software, firmware, circuit, module, set of data, text, number, code, symbol, a mark, or logic structured, organized, configured, programmed, designed, arranged, or engineered to convey information or indicate a state, condition, mode, context, location, or position to another apparatus, device, component, system, assembly, mechanism, hardware, software, firmware, circuit, module, and/or a user of an apparatus, device, component, system, assembly, mechanism, hardware, software, firmware, circuit, module that includes, or is associated with the indicator. The indicator can include one or more of an audible signal, a token, a presence of a signal, an absence of a signal, a tactile signal, a visual signal or indication, a visual marker, a visual icon, a visual symbol, a visual code, a visual mark, and/or the like. In certain embodiments, "indicator" can be used with an adjective describing the indicator. For example, a "mode indicator" is an indicator that identifies or indicates a mode.

As used herein, a "handle" or "knob" refers to a structure used to hold, control, or manipulate a device, apparatus, component, tool, or the like. A "handle" may be designed to be grasped and/or held using one or two hands of a user. In certain embodiments, a handle or knob may be an elongated structure. In one embodiment, a knob may be a shorter stubby structure.

As used herein, "implant" refers to a medical device manufactured to replace a missing biological structure, support a damaged biological structure, or enhance an existing biological structure. Often medical implants are man-made devices, but implants can also be natural occurring structures. The surface of implants that contact the body may be made of, or include a biomedical material such as titanium, cobalt chrome, stainless steel, carbon fiber, another metallic alloy, silicone, polymer, Synthetic polyvinyl alcohol (PVA) hydrogels, biomaterials, biocompatible polymers such as PolyEther Ether Ketone (PEEK) or a polylactide polymer (e.g. PLLA) and/or others, or apatite, or any combination of these depending on what is functional and/or economical. Implants can have a variety of configurations and can be wholly, partially, and/or include a number of components that are flexible, semiflexible, pliable, elastic, supple, semi-rigid, or rigid. In some cases implants contain electronics, e.g. artificial pacemaker and cochlear implants. Some implants are bioactive, such as subcutaneous drug delivery devices in the form of implantable pills or drug-eluting stents. Orthopedic implants may be used to alleviate issues with bones and/or joints of a patient's body. Orthopedic implants can be used to treat bone fractures, osteoarthritis, scoliosis, spinal stenosis, discomfort, and pain. Examples of orthopedic implants include, but are not limited to, a wide variety of pins, rods, screws, anchors, spacers, sutures, all-suture implants, ball all-suture implants, self-locking suture implants, cross-threaded suture implants, plates used to anchor fractured bones while the bones heal or fuse together, and the like. (Search "implant (medicine)" on Wikipedia.com May 26, 2021. CC-BY-SA 3.0 Modified. Accessed Jun. 30, 2021.)

As used herein, a "body" refers to a main or central part of a structure. The body may serve as a structural component to connect, interconnect, surround, enclose, and/or protect one or more other structural components. A body may be made from a variety of materials including, but not limited to, metal, plastic, ceramic, wood, fiberglass, acrylic, carbon, biocompatible materials, biodegradable materials or the like. A body may be formed of any biocompatible materials, including but not limited to biocompatible metals such as Titanium, Titanium alloys, stainless steel alloys, cobalt-chromium steel alloys, nickel-titanium alloys, shape memory alloys such as Nitinol, biocompatible ceramics, and biocompatible polymers such as Polyether ether ketone (PEEK) or a polylactide polymer (e.g. PLLA) and/or others. In one embodiment, a body may include a housing or frame or framework for a larger system, component, structure, or device. A body may include a modifier that identifies a particular function, location, orientation, operation, and/or a particular structure relating to the body. Examples of such modifiers applied to a body, include, but are not limited to, "inferior body," "superior body," "lateral body," "medial body," and the like.

As used herein, "bone engagement surface" refers to a surface of an object, instrument, or apparatus, such as an implant that is oriented toward or faces one or more bones of a patient. In one aspect, the bone engagement surface may abut, touch, or contact a surface of a bone. In another aspect, the bone engagement surface or parts of the bone engagement surface may be close to, but not abut, touch, or contact a surface of the bone. In certain aspects, the bone engagement surface can be configured to engage with a surface of one or more bones. Such a bone engagement surface may include projections, eminences, and/or recesses that correspond to and/or match anatomical features, bony topography, landmarks, projections, and/or recesses of the one or more bone surfaces.

"Bone engagement feature" refers to a structure, feature, component, aspect configured to contact, touch, abut, and/or engage with a bone, a bone part, and/or a bone fragment. A bone engagement feature may enable temporary engagement with a bone or bone fragment or permanent engagement with a bone or bone fragment. A bone engagement feature may include a bone engagement surface and a body section that supports the bone engagement surface. In certain embodiments, a bone engagement feature may include a bone probe. In one embodiment, a bone engagement feature may include a landmark registration feature.

"Frangible" refers to a type of material designed, engineered, and/or configured to break easily under an expected force. Frangible objects may be designed to break easily under the expected force to provide a safety feature, a convenience feature, or the like. Frangible objects can be made from metal, plastic, ceramics, wood, paper, or the like. Frangible also includes something that is breakable or fragile; especially something that is intentionally made so. (Search "frangible" on wordhippo.com. WordHippo, 2023. Web. Accessed 11 May 2023. Modified.)

As used herein, "side" refers to a structure or part of a structure including, but not limited to: one of a longer bounding surfaces or lines of an object especially contrasted with the ends, a line or surface forming a border or face of an object, either surface of a thin object, a bounding line or structure of a geometric figure or shape, and the like. (search "side" on Merriam-Webster.com. Merriam-Webster, 2021. Web. 3 Aug. 2021. Modified.) A side can also refer to a geometric edge of a polygon (two-dimensional shape) and/or a face or surface of a polyhedron (three-dimensional shape). (Search "side" on Wikipedia.com Jul. 21, 2021. CC-BY-SA 3.0 Modified. Accessed Aug. 3, 2021.) Side can also refer to a location on a structure. For example, a side can be a location on a structure at, or near, a furthest position away from a central axis of the structure. As used herein, the term "side" can include one or more modifiers that define and/or orient and/or distinguish the side of an object from others based on based on where and/or how the object is deployed within or in relation to a second object. For example, in the context of an implant for a patient, sides of the implant may be labeled based on where the sides are relative to the patient when the implant is deployed. As one example, an "anterior side" of an implant, instrument, anatomical structure, or other structure refers to a side that is anterior to other sides of the structure in relation to a patient when the structure is deployed in the patient. As another example, in the context of an instrument used with a patient, sides of the instrument may be labeled based on where the sides are when the instrument is being used for its purpose. As one example, a "front side" of an instrument refers to a side that is facing a user of the instrument when the instrument is in use.

As used herein, a "deploy" or "deployment" refers to an act, action, process, system, method, means, or apparatus for inserting an implant or prosthesis into a part, body part, and/or patient. "Deploy" or "deployment" can also refer to an act, action, process, system, method, means, or apparatus for placing something into therapeutic use. A device, system, component, medication, drug, compound, or nutrient may be deployed by a human operator, a mechanical device, an automated system, a computer system or program, a robotic system, or the like.

"Joint" or "Articulation" refers to the connection made between bones in a human or animal body which link the skeletal system to form a functional whole. Joints may be biomechanically classified as a simple joint, a compound joint, or a complex joint. Joints may be classified anatomically into groups such as joints of hand, elbow joints, wrist joints, axillary joints, sternoclavicular joints, vertebral articulations, temporomandibular joints, sacroiliac joints, hip joints, knee joints, articulations of foot, and the like. (Search "joint" on Wikipedia.com Dec. 19, 2021. CC-BY-SA 3.0 Modified. Accessed Jan. 20, 2022.)

"Tissue" refers to a structure that makes up a one or more anatomical structures of a patient (i.e., human or animal). Tissue can be soft tissue or hard tissue. "Soft tissue" refers to tissue of a patient (i.e., human or animal). Examples of soft tissue include but are not limited to skin, ligament, tendon, fascia, fat muscle, fibrous tissue, blood vessels, lymph vessels, brain tissue, and/or nerves. "Hard tissue" refers to any human or animal tissue that is not soft tissue. Examples of hard tissue include bone, teeth, tooth enamel, dentin, cementum, cartilage or the like.

"Topographical" refers to the physical distribution of parts, structures, or features on the surface of, or within, an organ or other anatomical structure, or organism. (Search "define topographical" on google.com. Oxford Languages, Copyright 2022. Oxford University Press. Web., Modified. Accessed 15 Feb. 2022.)

"Boundary" refers to a structure, line, or area where an object, surface, line, area, or operation is or is expected to begin and/or end. A boundary can be similar to a border.

"Landmark registration feature" refers to a structure configured to engage, contact, or abut a feature, aspect, attribute, or characteristic of a first object to orient and/or position a second object that includes the landmark registration feature with respect to the first object. A variety of structures can serve as a landmark registration feature. For example, a surface, a probe, a finger, a wing, an arm, an opening, or the like can function as landmark registration features. A landmark registration feature can be of a variety of shapes and thus can include a protrusion, a projection, a tuberosity, a cavity, a void, a divot, a tab, an extension, a hook, a curve, or the like.

"Landmark" refers to a structure on, in, or around a structure that can be used to serve as a reference for positioning, orienting, translating, rotating, or otherwise manipulating a second object or structure. For example, a landmark may include a protrusion, a projection, a tuberosity, a cavity, a void, a divot, a tab, an extension, a hook, a curve, or the like. In the context of bones of a patient, a landmark can include any protuberance, eminence, bony topography, anatomical features, calcifications, void, divot, concave section, sesamoid, bone spur or other feature on, or extending from, a bone of a patient. A landmark refers to any structure of an anatomical structure that is referenced, contacted, engaged with and/or associated with a landmark registration feature. In certain embodiments, a landmark is unique to one patient.

"Probe bone engagement surface" refers to a bone engagement surface on one surface of a probe or part of a probe.

"Landmark configuration" refers to an arrangement and/or organization of landmarks within, about, or around a certain area. In the context of bones, a landmark configuration may include a grouping of two or more landmarks on or about a specific surface of a bone. In one embodiment, a landmark configuration can include landmarks that abut and/or are covered by a bone engagement surface as the bone engagement surface is brought closer to a surface of the bone.

"Configuration" refers to an arrangement, setup, design, organization, or values of one or more parts, features, settings, components, aspects, structures, or the like as a module, component, apparatus, device, system, framework, platform, dashboard, assembly, or the like. Examples of configurations can include how dials are setup on a dashboard, levers are set on a control board, switches are set within a controller, bones are arranged within a hand, foot, or limb, or the like.

"Bone attachment feature" refers to a structure, feature, component, aspect configured to securely connect, couple, attach, and/or engage a structure, component, object, or body with a bone and/or a bone fragment. Examples of a bone attachment feature, include, but are not limited to, a pin, K-wire, screw, or other fastener alone, or in combination with, a hole, passage, and/or opening.

"Feedback" refers to a reactionary response to an action, a product, service, or task. (Search "feedback" on wordhippo.com. WordHippo, 2023. Web. Modified. Accessed 28 Aug. 2023.) "Haptic" refers to a signal, feeling, or action that a user or receiver can feel using their sense of touch. Thus, haptic feedback is a kind of feedback that a user can feel or detect using their sense of touch.

"Tendon trajectory guide" refers to any structure, apparatus, surface, device, system, feature, or aspect configured to indicate, identify, guide, place, position, or otherwise assist in marking or deploying a fastener or other structure along a desired trajectory for one or more subsequent steps in a procedure.

"Bone tunnel guide" refers to any structure, apparatus, surface, device, system, feature, or aspect configured to indicate, identify, guide, place, position, or otherwise assist in marking, forming, or deploying a fastener in order to form a bone tunnel. A bone tunnel is a tunnel that extends into and/or through one or more bones.

As used herein, "patient-specific osteotomy procedure" refers to an osteotomy procedure that has been adjusted, tailored, modified, or configured to specifically address the needs or desires or a particular patient. In certain aspects, one patient-specific osteotomy procedure may be useable in connection with only one patient. In other aspects, one patient-specific osteotomy procedure may be useable with a number of patients having a particular class of characteristics.

"Ankle fusion procedure" refers to a surgical procedure that seeks to immobilize an ankle joint of a patient. The surgery fuses two or more bones of the ankle of the patient. The surgery involves the use of screws, plates, medical nails, and other hardware or fasteners to achieve bone union. Ankle fusion is considered to be the gold standard for treatment of end-stage ankle arthritis. Ankle fusion trades joint mobility for relief from pain. (Search "ankle fusion" on Wikipedia.com Dec. 21, 2022. CC-BY-SA 3.0 Modified. Accessed Jun. 28, 2023.) An ankle fusion procedure may also be referred to as ankle arthrodesis, talocrural joint fusion, tibiotalar arthrodesis, and tibiotalocalcaneal arthrodesis. An ankle fusion procedure can be performed using a variety of approaches to the ankle including an anterior approach, a posterior approach, a lateral approach and a medial approach. Each approach may use common or different instrumentation or implants for the procedure.

"Deformity" refers to any abnormality in or of an organism, a part of an organism, or an anatomical structure of a patient that appears or functions differently than is considered normal, or is common, in relation to the same organism, a part of an organism, or an anatomical structure of other subjects of the same species as the patient. (Search "deformity" on Wikipedia.com Jun. 13, 2023. CC-BY-SA 3.0 Modified. Accessed Jun. 28, 2023.)

"Prescription" or "Prescribed" refers to an instruction, request, direction, determination, designation, authorization, and/or order, as by a physician or nurse practitioner, for the administration of a medicine, preparation of an implant, preparation of an instrument, or other intervention. Often a prescription is written. Prescription can also refer to the prescribed medicine or intervention. (Search "prescription" on wordhippo.com. WordHippo, 2023. Web. Accessed 3 May 2023. Modified.)

"User directions" refers to any request, instruction, direction, input, feedback, prescription, designation, order, directive, or the like from a user of an apparatus, system, device, component, subsystem, or other object. User directions can be created, sent, and/or received in a variety of forms and/or formats, including, but not limited to, a user action in a user interface, a prescription, a form, a conversation, an electronic mail message, a text message, a gesture by the user, or the like. In the context of an osteotomy procedure, user directions can include a set of default settings or choices or instructions for fabrication of a patient-specific instrument or set of instruments, an online form completed by a user (e.g., surgeon), a set of modifications to an original set of user directions, and the like.

"Position" refers to a place or location. (Search "position" on wordhippo.com. WordHippo, 2022. Web. Modified. Accessed 9 Aug. 2022.) Often, a position refers to a place or location of a first object in relation to a place or location of another object. One object can be positioned on, in, or relative to a second object. In addition, a position can refer to a place or location of a first object in relation to a place or location of another object in a virtual environment. For example, a model of one object can be positioned relative to a model of another object in a virtual environment such as a modeling software program.

"Contour" refers to an outline representing or bounding a shape or form of an object. Contour can also refer to an outside limit of an object, area, or surface of the object. (Search "contour" on wordhippo.com. WordHippo, 2023. Web. Modified. Accessed 13 Jun. 2023.)

As used herein, a "stop" refers to an apparatus, instrument, structure, member, device, component, system, or assembly structured, organized, configured, designed, arranged, or engineered to prevent, limit, impede, stop, or restrict motion or movement and/or operation of the another object, member, structure, component, part, apparatus, system, or assembly. In one embodiment, a stop may be used to manage and/or control a cutting tool.

As used herein, a "fastener", "fixation device", or "fastener system" refers to any structure configured, designed, or engineered to join two structures. Fasteners may be made of a variety of materials including metal, plastic, composite materials, metal alloys, plastic composites, and the like. Examples of fasteners include, but are not limited to screws, rivets, bolts, nails, snaps, hook and loop, set screws, bone screws, nuts, posts, pins, thumb screws, and the like. Other examples of fasteners include, but are not limited to wires, Kirschner wires (K-wire), anchors, bone anchors, plates, bone plates, intramedullary nails or rods or pins, implants, sutures, soft sutures, soft anchors, tethers, interbody cages, fusion cages, and the like.

In certain embodiments, the term fastener may refer to a fastener system that includes two or more structures configured to combine to serve as a fastener. An example of a fastener system is a rod or shaft having external threads and an opening or bore within another structure having corresponding internal threads configured to engage the external threads of the rod or shaft.

In certain embodiments, the term fastener may be used with an adjective that identifies an object or structure that the fastener may be particularly configured, designed, or engineered to engage, connect to, join, contact, or couple together with one or more other structures of the same or different types. For example, a "bone fastener" may refer to an apparatus for joining or connecting one or more bones, one or more bone portions, soft tissue and a bone or bone portion, hard tissue and a bone or bone portion, an apparatus and a bone or portion of bone, or the like.

In certain embodiments, a fastener may be a temporary fastener. A temporary fastener is configured to engage and serve a fastening function for a relatively short period of time. Typically, a temporary fastener is configured to be used until another procedure or operation is completed and/or until a particular event. In certain embodiments, a user may remove or disengage a temporary fastener. Alternatively, or in addition, another structure, event, or machine may cause the temporary fastener to become disengaged.

As used herein, a "fixator" refers to an apparatus, instrument, structure, device, component, member, system, assembly, or module structured, organized, configured, designed, arranged, or engineered to connect two bones or bone fragments or a single bone or bone fragment and another fixator to position and retain the bone or bone fragments in a desired position and/or orientation. Examples of fixators include both those for external fixation as well as those for internal fixation and include, but are not limited to pins, wires, Kirschner wires, screws, anchors, bone anchors, plates, bone plates, intramedullary nails or rods or pins, implants, interbody cages, fusion cages, and the like. Fixation refers to the act of deploying or using a fixator to fix two structures together.

As used herein, an "anchor" refers to an apparatus, instrument, structure, member, part, device, component, system, or assembly structured, organized, configured, designed, arranged, or engineered to secure, retain, stop, and/or hold, an object to or at a fixed point, position, or location. Often, an anchor is coupled and/or connected to a flexible member such as a tether, chain, rope, wire, thread, suture, suture tape, or other like object. Alternatively, or in addition, an anchor may also be coupled, connected, and/or joined to a rigid object or structure. In certain embodiments, an anchor can be a fixation device. Said another way, a fixation device can function as an anchor. In certain embodiments, the term anchor may be used as an adjective that describes a function, feature, or purpose for the noun the adjective 'anchor' describes. For example, an anchor hole is a hole that serves as or can be used as an anchor.

"Connector" refers to any structure configured, engineered, designed, adapted, and/or arranged to connect one structure, component, element, or apparatus to another structure, component, element, or apparatus. A connector can be rigid, pliable, elastic, flexible, and/or semiflexible. Examples of a connector include but are not limited to any fastener.

"Clearance" refers to a space or opening that provides an unobstructed area to permit one object to move freely in relation to another object.

"Correction," in a medical context, refers to a process, procedure, device, instrument, apparatus, system, implant, or the like that is configured, designed, developed, fabricated, configured, and/or organized to adjust, translate, move, orient, rotate, or otherwise change an anatomical structure from an original position, location, and/or orientation to a new position, location, and/or orientation that provides a benefit to a patient. The benefit may be one of appearance, anatomical function, pain relief, increased mobility, increased strength, and the like.

"Uniplanar correction" refers to a medical correction, which can include an osteo correction, in one plane (e.g., one of a sagittal plane, a transverse plane, and a coronal/frontal plane) of an anatomical structure such as a foot, hand, or body of a patient.

"Biplanar correction" refers to a medical correction, which can include an osteo correction, in two planes (e.g., two of a sagittal plane, a transverse plane, and a coronal/frontal plane) of an anatomical structure such as a foot, hand, or body of a patient.

"Triplane correction" refers to a medical correction, which can include an osteo correction, in three planes (e.g., all three planes of a sagittal plane, a transverse plane, and a coronal/frontal plane) of an anatomical structure such as a foot, hand, or body of a patient.

"Probe" refers to a medical instrument used to explore, identify, locate, or register to, wounds, organs, and/or anatomical structures including a joint or an articular surface. In certain embodiments, a probe can be thin and/or pointed. In one embodiment, a probe is connected, integrated with, and/or coupled to another structure or instrument. In such an embodiment, the probe may serve to facilitate proper positioning of the another structure or instrument. For example, the probe may be used to identify and/or locate a particular anatomical structure and the positioning of the probe may then cause the connected structure or instrument to also be positioned in a desired location relative to one or more anatomical structures.

As used herein, "manufacturing tool" or "fabrication tool" refers to a manufacturing or fabrication process, tool, system, or apparatus which creates an object, device, apparatus, feature, or component using one or more source materials. A manufacturing tool or fabrication tool can use a variety of manufacturing processes, including but not limited to additive manufacturing, subtractive manufacturing, forging, casting, and the like. The manufacturing tool can use a variety of materials including polymers, thermoplastics, metals, biocompatible materials, biodegradable materials, ceramics, biochemicals, and the like. A manufacturing tool may be operated manually by an operator, automatically using a computer numerical controller (CNC), or a combination of these techniques.

"Friction fit" refers to a type of joint or connection that is created between two components by means of friction. A joint or connection that is formed using a friction fit may or may not include the use of additional fasteners such as screws, bolts, or adhesives. In a friction fit, the components are designed or configured to fit tightly together, creating enough friction between the surfaces to hold them securely in place, at least temporarily. The friction force is generated by the compressive force that is experienced between the components, and can be strong enough to prevent the components from separating under normal conditions. (© ChatGPT March 23 Version, Modified, accessed chat.openai.com/chat May 2, 2023).

As used herein, "osteotomy procedure" or "surgical osteotomy" or "osteotomy" refers to a surgical operation in which one or more bones are cut to shorten or lengthen them or to change their alignment. The procedure can include removing one or more portions of bone and/or adding one or more portions of bone or bone substitutes. (Search "osteotomy" on Wikipedia.com Feb. 3, 22, 2021. CC-BY-SA 3.0 Modified. Accessed Feb. 15, 2022.) As used herein, "patient-specific osteotomy procedure" refers to an osteotomy procedure that has been adjusted, tailored, modified, or configured to specifically address the anatomy, physiology, condition, abnormalities, needs, or desires of a particular patient. In certain aspects, one patient-specific osteotomy procedure may be useable in connection with only one patient. In other aspects, one patient-specific osteotomy procedure may be useable with a number of patients having a particular class of characteristics. In certain aspects, a patient-specific osteotomy procedure may refer to a non-patient-specific osteotomy procedure that includes one or more patient-specific implants and/or instrumentation. In another aspects, a patient-specific osteotomy procedure may refer to a patient-specific osteotomy procedure that includes one or more patient-specific implants, patient-specific surgical steps, and/or patient-specific instrumentation.

"Wedge osteotomy" refers to an osteotomy procedure in which one or more wedges are used as part of the procedure. Generally, wedge osteotomies can be of one of two types, open wedge and closing wedge. The type of osteotomy refers to how the procedure changes the relation between two parts of a bone involved in the osteotomy. In an open wedge osteotomy a wedge of bone or graft or other material is inserted in between two parts of a bone. Consequently, a wedge shape is "opened" in the bone. In a close wedge osteotomy or closing wedge osteotomy a wedge of bone is removed from a bone. Consequently, a wedge shape formed in the bone is "closed."

"Metatarsal" is a bone of a foot of a human or animal. In a human, a foot typically includes five metatarsals which are identified by number starting from the most medial metatarsal, which is referred to as a first metatarsal and moving laterally the next metatarsal is the second metatarsal, and the naming continues in like manner for the third, fourth, and fifth metatarsal. The metatarsal bone includes three parts a base which is a part that is at a proximal end of the metatarsal, a head which is a part that is at a distal end of the metatarsal, and a shaft or neck connects the base to the head.

"Epiphyses" refers to the rounded end of a long bone, at long bone's joint with adjacent bone(s). Between the epiphysis and diaphysis (the long midsection of the long bone) lies the metaphysis, including the epiphyseal plate (growth plate). At the joint, the epiphysis is covered with articular cartilage; below that covering is a zone similar to the epiphyseal plate, known as subchondral bone. (Search 'epiphysis' on Wikipedia.com 17 Jun. 2022. Modified. Accessed Aug. 1, 2022.) "Metaphysis" refers to the neck portion of a long bone between the epiphysis and the diaphysis. The metaphysis contains the growth plate, the part of the bone that grows during childhood, and as the metaphysis grows the metaphysis ossifies near the diaphysis and the epiphyses. (Search 'metaphysis' on Wikipedia.com 17 Jun. 2022. Modified. Accessed Aug. 1, 2022.) "Diaphysis" refers to the main or midsection (shaft) of a long bone. The diaphysis is made up of cortical bone and usually contains bone marrow and adipose tissue (fat). The diaphysis is a middle tubular part composed of compact bone which surrounds a central marrow cavity which contains red or yellow marrow. In diaphysis, primary ossification occurs. (Search 'diaphysis' on Wikipedia.com 17 Jun. 2022. Modified. Accessed Aug. 1, 2022.)

"Metaphyseal Diaphyseal Junction" or "MDJ" refers to an area of a long bone between the Metaphysis and the Diaphysis. This area can also include or be referred to as the epiphyseal plate (growth) plate. For certain surgical procedures, performing an osteotomy at or near the metaphyseal diaphyseal junction may be advantageous and desirable to promote rapid fusion of two cut faces formed in the osteotomy and bone growth to close the osteotomy, and/or may mitigate the risk of a nonunion of the osteotomy.

As used herein, a "base" refers to a main or central structure, component, or part of a structure. A base is often a structure, component, or part upon which, or from which other structures extend into, out of, away from, are coupled to, or connect to. A base may have a variety of geometric shapes and configurations. A base may be rigid or pliable. A base may be solid or hollow. A base can have any number of sides. In one embodiment, a base may include a housing, frame, or framework for a larger system, component, structure, or device. In certain embodiments, a base can be a part at the bottom or underneath a structure designed to extend vertically when the structure is in a desired configuration or position. Certain bones such as a metatarsal bone can include a base as one structural component of the bone.

As used herein, "anatomic data" refers to data identified, used, collected, gathered, and/or generated in connection with an anatomy of a human or animal. Examples of anatomic data may include location data for structures, both independent, and those connected to other structures within a coordinate system. Anatomic data may also include data that labels or identifies one or more anatomical structures. Anatomic data can include volumetric data, material composition data, and/or the like. Anatomic data can be generated based on medical imaging data or measurements using a variety of instruments including monitors and/or sensors. Anatomic data can be gathered, measured, or collected from anatomical models and/or can be used to generate, manipulate, or modify anatomical models.

A bone model or anatomic model of a patient's body or body part(s) may be generated by computing devices that analyze medical imaging images. Structures of a patient's body can be determined using a process called segmentation.

"Positioner" or "positioning guide" refers to any structure, apparatus, surface, device, system, feature, or aspect configured to position, move, translate, manipulate, or arrange one object in relation to another. In certain embodiments, a positioner can be used for one step in surgical procedure to position, arrange, orient, and/or reduce one bone or bone fragment relative to another. In such embodiments, the positioner may be referred to as a bone positioner. In certain embodiments, the term positioner or positioning guide may be preceded by an adjective that identifies the structure, implement, component, or instrument that may be used with, positioned by, and/or guided by with the positioner. For example, a "pin positioner" may be configured to accept a pin or wire such as a K-wire and serve to position or place the pin relative to another structure such as a bone.

"Rotation guide" or "rotator" refers to any structure, apparatus, surface, device, system, feature, or aspect configured, designed, engineered, or fabricated to rotate or aid a user in the rotation of one structure relative to another structure. In certain embodiments, a rotation guide or rotator may be used to help a surgeon rotate one or more bones, parts of bones, bone fragment, an implant, or other anatomical structure, either alone or in relation to another one or more bones, parts of bones, bone fragments, implants, or other anatomical structures.

"Trajectory" refers to a path a body travels or a path configured for a body to travel through space. (Search "trajectory" on wordhippo.com. WordHippo, 2023. Web. Modified. Accessed 13 Jun. 2023.)

"Trajectory guide" or "trajectory indicator" or "targeting guide" refers to any structure, apparatus, surface, device, system, feature, or aspect configured to indicate, identify, guide, place, position, or otherwise assist in marking or deploying a fastener or other structure along a desired trajectory for one or more subsequent steps in a procedure.

"Trajectory port" refers to any structure, apparatus, surface, device, system, feature, or aspect configured to indicate, identify, guide, place, position, or otherwise assist in marking or deploying a fastener, an anchor, a tunnel, an opening, or other structure along a desired trajectory for one or more subsequent steps in a procedure. In certain embodiments, a trajectory port includes a body or base (aka a port body) and an opening or port. The base/body supports the opening and the opening extends through the base/body from one side to the opposite side and has a predetermined angle of incidence with a hard tissue or a soft tissue of a patient.

"Tendon trajectory guide" refers to a trajectory guide configured to indicate, identify, guide, place, position, or otherwise assist in deploying a tendon or other soft tissue along a desired trajectory for one or more subsequent steps in a procedure.

"Tendon transfer system" refers to a system for facilitating a surgical procedure that locates or relocates a tendon anchor point on one bone to a new or different location on the same or on a different bone.

"Tendon transfer anchor guide" refers to any structure and/or instrument that can serve to guide the formation, deployment, or establishing of an anchor or a structure or component of an anchor such as a hole, an opening, a tunnel, or the like. In certain embodiments, a tendon transfer anchor guide is a guide that facilitates formation of a bone tunnel for deployment of an anchor for a tendon that is anchored as part of a surgical procedure.

"Recommended location" refers to a location for deployment of a tendon or other soft tissue on, in, or within a body part of a patient.

As used herein, an "inserter" refers to an apparatus, instrument, structure, device, component, system, or assembly that is structured, organized, configured, designed, arranged, or engineered to insert or deploy one or more components, parts, or devices. In certain embodiments, an inserter can be used to insert implants and/or prosthesis into tissue, organs, or parts of a patient. In certain embodiments, an inserter can also be used to extract, retract, reposition, or remove an implant and/or prosthesis.

"Point" refers to a mechanical device, apparatus, member, component, system, assembly, or structure having a larger diameter on one end than the diameter on the opposite end. In certain embodiments, a point has a proximal end connected or coupled to a base, shaft, and/or body and a distal end that is free. A point may have a variety of cross-sectional shapes including round, circular, square, oval, rectangular, and the like. In certain embodiments, a point may progressively taper from a larger diameter on one end to a small sharp end on an opposite end. Alternatively, a free end of a point may have a flat or angled end instead of a sharp tip.

"Appendage" refers to a projecting part of a structure or living organism, with a distinct appearance and/or function. (Search "appendage" on wordhippo.com. WordHippo, 2023. Web. Modified. Accessed 28 Aug. 2023.) Examples of appendages include fingers, toes, arms, legs, tails, and the like. Examples of an appendage can include a structure of an object or instrument that emulate or have a similar function to similar structures on a person or animal.

"Order" or "an order" refers to a set of instructions for performance of a particular task and/or providing of a particular item. Examples of an order, include, but are not limited to, a set of doctor's orders, a prescription, a patient-specific implant fabrication request, a request for production of a particular product, system, instrument, or the like.

"Soft tissue transfer surgical procedure" or "Soft tissue rearrangement procedure" refers to any surgical procedure that includes a goal or outcome that positions, repositions, or relocates a soft tissue, such as a tendon or ligament or graft, to a location on, in, about, or through one or more bones of a patient. Examples of tendon transfer surgical procedures, include, but are not limited to, Achilles Tendon Transfer, Flexor hallucis longus (FHL) tendon transfer, tibialis posterior tendon transfer, posterior tibia tendon transfer, tibialis anterior tendon transfer, Jones tenosuspension, Extensor digitorum longus (EDL) transfer, Tibialis anterior tendon (TAT) transfer, Flexor digitorum longus (FDL) transfer, Extensor hallucis longus (EHL) transfer, lateral ankle ligament reconstruction including ligament anchoring for Anterior talofibular ligament ATFL, calcaneofibular ligament (CFL), and plantar calcaneonavicular ligament. A soft tissue transfer surgical procedure can also be referred to as a tendon transfer or tendon transfer procedure, a ligament transfer or ligament transfer procedure, or the like.

"Metatarsal base resection guide" refers to a resection guide designed, engineered, fabricated, or intended for use with, one, in, or about a base part, section, surface, portion, or aspect of a metatarsal for one or more steps of a medical procedure. The metatarsal base resection guide may be used to form an osteotomy, to resect a wedge for a closing wedge procedure, resect a bone wedge that preserves a cortical layer of bone opposite the resected bone wedge, form an osteotomy that uniplanar wedge, a biplanar wedge, or a triplane wedge. Various embodiments of a metatarsal base resection guide may be used on a medial surface, a dorsal surface, a lateral surface, or a plantar surface of a single metatarsal. Alternatively, or in addition, various embodiments of a metatarsal base resection guide can be used on two or more metatarsals.

"Reduction guide" or "reducer" refers to any structure, apparatus, surface, device, system, feature, or aspect configured, designed, engineered, or fabricated to reduce or aide a user in the reduction of one bone or bone fragment or implant in relation to another bone or bone fragment or implant.

"Fastener guide" or "reducer" refers to any structure, apparatus, surface, device, system, feature, or aspect configured, designed, engineered, or fabricated to guide or direct a fastener into a bone as part of deploying the fastener. Examples of a fastener guide include an opening in a structure that is sized and/or oriented for deployment of a fastener such as a bone screw, a reference pin for aligning a fastener for deployment at a desired orientation and/or trajectory, and the like.

As used herein, a "guard" refers to an apparatus, instrument, structure, member, device, component, system, or assembly structured, organized, configured, designed, arranged, or engineered to prevent, limit, impede, stop, or restrict motion, action, or movement and/or operation of the another object, member, structure, component, part, apparatus, system, or assembly beyond a certain parameter such as a boundary. Said another way, a "guard" refers to an apparatus, instrument, structure, member, device, component, system, or assembly structured, organized, configured, designed, arranged, or engineered to retain, maintain, hold, keep, or restrict motion, action, or movement and/or operation of the another object, member, structure, component, part, apparatus, system, or assembly within or at one or more parameters such as a boundary.

As used herein, "artificial intelligence" refers to intelligence demonstrated by machines, unlike the natural intelligence displayed by humans and animals, which involves consciousness and emotionality. The distinction between artificial intelligence and natural intelligence categories is often revealed by the acronym chosen. 'Strong' AI is usually labelled as artificial general intelligence (AGI) while attempts to emulate 'natural' intelligence have been called artificial biological intelligence (ABI). Leading AI textbooks define the field as the study of "intelligent agents": any device that perceives its environment and takes actions that maximize its chance of achieving its goals. The term "artificial intelligence" can also be used to describe machines that mimic "cognitive" functions that humans associate with the human mind, such as "learning" and "problem solving". (Search "artificial intelligence" on Wikipedia.com Jun. 25, 2021. CC-BY-SA 3.0 Modified. Accessed Jun. 25, 2021.)

As used herein, "segmentation" or "image segmentation" refers to the process of partitioning an image into different meaningful segments. These segments may correspond to different tissue classes, organs, pathologies, bones, or other biologically relevant structures. Medical image segmentation accommodates imaging ambiguities such as by low contrast, noise, and other imaging ambiguities.

Certain computer vision techniques can be used or adapted for image segmentation. For example, the techniques and or algorithms for segmentation may include, but are not limited to: Atlas-Based Segmentation: For many applications, a clinical expert can manually label several images; segmenting unseen images is a matter of extrapolating from these manually labeled training images. Methods of this style are typically referred to as atlas-based segmentation methods. Parametric atlas methods typically combine these training images into a single atlas image, while non-parametric atlas methods typically use all of the training images separately. Atlas-based methods usually require the use of image registration in order to align the atlas image or images to a new, unseen image.

Image registration is a process of correctly aligning images; Shape-Based Segmentation: Many methods parametrize a template shape for a given structure, often relying on control points along the boundary. The entire shape is then deformed to match a new image. Two of the most common shape-based techniques are Active Shape Models and Active Appearance Models; Image-Based Segmentation: Some methods initiate a template and refine its shape according to the image data while minimizing integral error measures, like the Active contour model and its variations; Interactive Segmentation: Interactive methods are useful when clinicians can provide some information, such as a seed region or rough outline of the region to segment. An algorithm can then iteratively refine such a segmentation, with or without guidance from the clinician. Manual segmentation, using tools such as a paint brush to explicitly define the tissue class of each pixel, remains the gold standard for many imaging applications. Recently, principles from feedback control theory have been incorporated into segmentation, which give the user much greater flexibility and allow for the automatic correction of errors; Subjective surface Segmentation: This method is based on the idea of evolution of segmentation function which is governed by an advection-diffusion model. To segment an object, a segmentation seed is needed (that is the starting point that determines the approximate position of the object in the image). Consequently, an initial segmentation function is constructed. With the subjective surface method, the position of the seed is the main factor determining the form of this segmentation function; and Hybrid segmentation which is based on combination of methods. (Search "medical image computing" on Wikipedia.com Jun. 24, 2021. CC-BY-SA 3.0 Modified. Accessed Jun. 24, 2021.)

As used herein, "medical imaging" refers to a technique and process of imaging the interior of a body for clinical analysis and medical intervention, as well as visual representation of the function of some organs or tissues (physiology). Medical imaging seeks to reveal internal structures hidden by the skin and bones, as well as to diagnose and treat disease. Medical imaging may be used to establish a database of normal anatomy and physiology to make possible identification of abnormalities. Medical imaging in its widest sense, is part of biological imaging and incorporates radiology, which uses the imaging technologies of X-ray radiography, magnetic resonance imaging, ultrasound, endoscopy, elastography, tactile imaging, thermography, medical photography, nuclear medicine functional imaging techniques as positron emission tomography (PET) and single-photon emission computed tomography (SPECT). Another form of X-ray radiography includes computerized tomography (CT) scans in which a computer controls the position of the X-ray sources and detectors. Magnetic Resonance Imaging (MRI) is another medical imaging technology. Measurement and recording techniques that are not primarily designed to produce images, such as electroencephalography (EEG), magnetoencephalography (MEG), electrocardiography (ECG), and others, represent other technologies that produce data susceptible to representation as a parameter graph vs. time or maps that contain data about the measurement locations. In certain embodiments bone imaging includes devices that scan and gather bone density anatomic data. These technologies may be considered forms of medical imaging in certain disciplines. (Search "medical imaging" on Wikipedia.com Jun. 16, 2021. CC-BY-SA 3.0 Modified. Accessed Jun. 23, 2021.) Data, including images, text, and other data associated with medical imaging is referred to as patient imaging data. As used herein, "patient imaging data" refers to data identified, used, collected, gathered, and/or generated in connection with medical imaging and/or medical imaging data. Patient imaging data can be shared between users, systems, patients, and professionals using a common data format referred to as Digital Imaging and Communications in Medicine (DICOM) data. DICOM data is a standard format for storing, viewing, retrieving, and sharing medical images.

As used herein, "medical image computing" or "medical image processing" refers to systems, software, hardware, components, and/or apparatus that involve and combine the fields of computer science, information engineering, electrical engineering, physics, mathematics and medicine. Medical image computing develops computational and mathematical methods for working with medical images and their use for biomedical research and clinical care. One goal for medical image computing is to extract clinically relevant information or knowledge from medical images. While closely related to the field of medical imaging, medical image computing focuses on the computational analysis of the images, not their acquisition. The methods can be grouped into several broad categories: image segmentation, image registration, image-based physiological modeling, and others. (Search "medical image computing" on Wikipedia.com Jun. 24, 2021. CC-BY-SA 3.0 Modified. Accessed Jun. 24, 2021.) Medical image computing may include one or more processors or controllers on one or more computing devices. Such processors or controllers may be referred to herein as medical image processors. Medical imaging and medical image computing together can provide systems and methods to image, quantify and fuse both structural and functional information about a patient in vivo. These two technologies include the transformation of computational models to represent specific subjects/patients, thus paving the way for personalized computational models. Individualization of generic computational models through imaging can be realized in three complementary directions: definition of the subject-specific computational domain (anatomy) and related subdomains (tissue types); definition of boundary and initial conditions from (dynamic and/or functional) imaging; and characterization of structural and functional tissue properties. Medical imaging and medical image computing enable the translation of models to the clinical setting with both diagnostic and therapeutic applications. (Id.) In certain embodiments, medical image computing can be used to generate a bone model, a patient-specific model, and/or a patent specific instrument from medical imaging and/or medical imaging data.

As used herein, "model" refers to an informative representation of an object, person or system. Representational models can be broadly divided into the concrete (e.g. physical form) and the abstract (e.g. behavioral patterns, especially as expressed in mathematical form). In abstract form, certain models may be based on data used in a computer system or software program to represent the model. Such models can be referred to as computer models. Computer models can be used to display the model, modify the model, print the model (either on a 2D medium or using a 3D printer or additive manufacturing technology). Computer models can also be used in environments with models of other objects, people, or systems. Computer models can also be used to generate simulations, display in virtual environment systems, display in augmented reality systems, or the like. Computer models can be used in Computer Aided Design (CAD) and/or Computer Aided Manufacturing (CAM) systems. Certain models may be identified with an adjective that identifies the object, person, or system the model represents. For example, a "bone" model is a model of a bone, and a "heart" model is a model of a heart. (Search "model" on Wikipedia.com Jun. 13, 2021. CC-BY-SA 3.0 Modified. Accessed Jun. 23, 2021.) As used herein, "additive manufacturing" refers to a manufacturing process in which materials are joined together in a process that repeatedly builds one layer on top of another to generate a three-dimensional structure or object. Additive manufacturing may also be referred to using different terms including: additive processes, additive fabrication, additive techniques, additive layer manufacturing, layer manufacturing, freeform fabrication, ASTM F2792 (American Society for Testing and Materials), and 3D printing. Additive manufacturing can build the three-dimensional structure or object using computer-controlled equipment that applies successive layers of the material(s) based on a three-dimensional model that may be defined using Computer Aided Design (CAD) software. Additive manufacturing can use a variety of materials including polymers, thermoplastics, metals, ceramics, biochemicals, and the like. Additive manufacturing may provide unique benefits, as an implant together with the pores and/or lattices can be directly manufactured (without the need to generate molds, tool paths, perform any milling, and/or other manufacturing steps).

"Repository" refers to any data source or dataset that includes data or content. In one embodiment, a repository resides on a computing device. In another embodiment, a repository resides on a remote computing or remote storage device. A repository may comprise a file, a folder, a directory, a set of files, a set of folders, a set of directories, a database, an application, a software application, content of a text, content of an email, content of a calendar entry, and the like. A repository, in one embodiment, comprises unstructured data. A repository, in one embodiment, comprises structured data such as a table, an array, a queue, a look up table, a hash table, a heap, a stack, or the like. A repository may store data in any format including binary, text, encrypted, unencrypted, a proprietary format, or the like.

"Reference" refers to any apparatus, structure, device, system, component, marking, and/or indicator organized, configured, designed, engineered, and/or arranged to serve as a source of information or a point of comparison used to support or establish knowledge, truth, or quality. (© ChatGPT January 9 Version, Modified, accessed chat.openai.com/chat Jan. 28, 2023). In certain embodiments, a reference can serve as a starting point or initial position for one or more steps in a surgical procedure. A reference may be a type of fiducial. In certain embodiments, "reference" can be combined with an adjective describing the reference. For example, a "model reference" is a reference within a model such as a computer model. A model reference refers to any feature, aspect, and/or component within a model. Examples of a model reference include, but are not limited to, a point, a plane, a line, a plurality of points, a surface, an anatomical structure, a shape, or the like. An "anatomical reference" is a reference within, on, near, or otherwise associated with an anatomical structure such as a bone. A reference (e.g., model, actual, virtual, and/or real) may also be referred to as a reference feature.

"Reference feature" refers to a feature configured for use as a point, plane, axis, or line of reference (aka a reference). A reference or reference feature can be used to position, measure, orient, fixation, couple, engage, and/or align one object or structure with another object or structure. In certain embodiments, a reference or reference feature can serve as a baseline, a ground truth, a waypoint, a control point, a landmark, and/or the like. A reference feature can facilitate moving from one coordinate system or frame of reference in a virtual environment to a position, location, frame of reference, environment, or orientation on, or in, an actual object, structure, device, apparatus, anatomical structure, or the like. Advantageously, a reference feature can coordinate objects, models, or structures in a digital or virtual model or representation with corresponding objects or structures (e.g., anatomical structures) of actual physical objects or structures. Said another way, a reference feature can serve to map from a virtual or modeled object to an actual or physical object. As used herein, "feature" refers to a distinctive attribute or aspect of something. (Search "feature" on google.com. Oxford Languages, 2021. Web. 20 Apr. 2021.) A feature may include one or more apparatuses, structures, objects, systems, sub-systems, devices, or the like. A feature may include a modifier that identifies a particular function or operation and/or a particular structure relating to the feature. Examples of such modifiers applied to a feature, include, but are not limited to, "attachment feature," "alignment feature," "securing feature," "placement feature," "protruding feature," "engagement feature," "disengagement feature," "resection feature", "guide feature", "alignment feature," and the like.

As used herein, a "marking" or "marker" refers to a symbol, letter, lettering, word, phrase, icon, design, color, diagram, indicator, figure, structure, device, apparatus, surface, component, system, or combination of these designed, intended, structured, organized, configured, programmed, arranged, or engineered to communication information and/or a message to a user receiving, viewing, or encountering the marking. The marking or "marker" can include one or more of a tactile signal, a visual signal or indication, an audible signal, and the like. In one embodiment, a marking may comprise a number or set letters, symbols, or words positioned on a surface, structure, color, color scheme, or device to convey a desired message or set of information.

"Place" refers to a position or location for a component, structure, device, object, or person. In certain embodiments, place refers to a position, orientation, or location relative to one or more other objects or structures. In other embodiments, a place can refer to a geographic location.

"Set" refers to a collection of objects. A set can have zero or more objects in the collection. Generally, a set includes one or more objects in the collection.

As used herein, a "sleeve" refers to structure that is narrow and longer longitudinally than the structure is wide. In certain embodiments, a sleeve serves to surround, enclose, wrap, and/or contain something else. In certain embodiments, a sleeve may surround, enclose, wrap, and/or contain a passage or void. (Search "sleeve" on wordhippo.com. WordHippo, 2021. Web. Accessed 15 Nov. 2021. Modified.) In certain embodiments, the term sleeve may be preceded by an adjective that identifies the structure, implement, component or instrument that may be used with, inserted into or associated with the sleeve. For example, a "pin sleeve" may be configured to accept a pin or wire such as a K-wire, a "drive sleeve" may be configured to accept a drill or drill bit, a "fixation member sleeve" may be configured to accept a fastener or fixation member.

As used herein, a "fixation" or "fixation device" refers to an apparatus, instrument, structure, device, component, member, system, assembly, step, process, or module structured, organized, configured, designed, arranged, or engineered to connect two structures either permanently or temporarily. The two structures may be one or the other or both of manmade and/or biological tissues, hard tissues such as bones, teeth or the like, soft tissues such as ligament, cartilage, tendon, or the like. In certain embodiments, fixation is used as an adjective to describe a device or component or step in securing two structures such that the structures remain connected to each other in a desired position and/or orientation. Fixation devices can also serve to maintain a desired level of tension, compression, or redistribute load and stresses experienced by the two structures and can serve to reduce relative motion of one part relative to others. Examples of fixation devices are many and include both those for external fixation as well as those for internal fixation and include, but are not limited to pins, wires, Kirschner wires (K-wires), screws, anchors, bone anchors, plates, bone plates, intramedullary nails or rods or pins, implants, interbody cages, fusion cages, and the like.

"Fusion" refers to a natural process of bone growth and generation in which two separate bones and/or bone fragments grow together as new bone grows when the two separate bones and/or bone fragments contact each other. Often, fusion is facilitated by compression of the two separate bones and/or bone fragments towards each other.

As used herein, "image registration" refers to a method, process, module, component, apparatus, and/or system that seeks to achieve precision in the alignment of two images. As used here, "image" may refer to either or both an image of a structure or object and another image or a model (e.g., a computer based model or a physical model, in either two dimensions or three dimensions). In the simplest case of image registration, two images are aligned. One image may serve as the target image and the other as a source image; the source image is transformed, positioned, realigned, and/or modified to match the target image. An optimization procedure may be applied that updates the transformation of the source image based on a similarity value that evaluates the current quality of the alignment. An iterative procedure of optimization may be repeated until a (local) optimum is found. An example is the registration of CT and PET images to combine structural and metabolic information. Image registration can be used in a variety of medical applications: Studying temporal changes; Longitudinal studies may acquire images over several months or years to study long-term processes, such as disease progression. Time series correspond to images acquired within the same session (seconds or minutes). Time series images can be used to study cognitive processes, heart deformations and respiration; Combining complementary information from different imaging modalities. One example may be the fusion of anatomical and functional information.

Since the size and shape of structures vary across modalities, evaluating the alignment quality can be more challenging. Thus, similarity measures such as mutual information may be used; Characterizing a population of subjects. In contrast to intra-subject registration, a one-to-one mapping may not exist between subjects, depending on the structural variability of the organ of interest. Inter-subject registration may be used for atlas construction in computational anatomy. Here, the objective may be to statistically model the anatomy of organs across subjects; Computer-assisted surgery: in computer-assisted surgery pre-operative images such as CT or MRI may be registered to intra-operative images or tracking systems to facilitate image guidance or navigation. There may be several considerations made when performing image registration: The transformation model. Common choices are rigid, affine, and deformable transformation models. B-spline and thin plate spline models are commonly used for parameterized transformation fields. Non-parametric or dense deformation fields carry a displacement vector at every grid location; this may use additional regularization constraints. A specific class of deformation fields are diffeomorphisms, which are invertible transformations with a smooth inverse; The similarity metric. A distance or similarity function is used to quantify the registration quality. This similarity can be calculated either on the original images or on features extracted from the images. Common similarity measures are sum of squared distances (SSD), correlation coefficient, and mutual information. The choice of similarity measure depends on whether the images are from the same modality; the acquisition noise can also play a role in this decision. For example, SSD may be the optimal similarity measure for images of the same modality with Gaussian noise. However, the image statistics in ultrasound may be significantly different from Gaussian noise, leading to the introduction of ultrasound specific similarity measures.

Multi-modal registration may use a more sophisticated similarity measure; alternatively, a different image representation can be used, such as structural representations or registering adjacent anatomy; The optimization procedure. Either continuous or discrete optimization is performed. For continuous optimization, gradient-based optimization techniques are applied to improve the convergence speed. (Search “medical image computing” on Wikipedia.com Jun. 24, 2021. CC-BY-SA 3.0 Modified. Accessed Jun. 25, 2021.)

“Register” or “Registration” refers to an act of aligning, mating, contacting, engaging, or coupling one or more parts and/or surfaces of one object in relation to one or more parts and/or surfaces of another object. Registering and/or registration can include two parts or surfaces of different object abutting each other and/or coming into close proximity to each other. Often, the one or more parts and/or surfaces of one object include protrusions and/or depressions that are the inverse or mirror configuration of protrusions and/or depressions of one or more parts and/or surfaces of the other object.

“Registration key” refers to a structure, surface, feature, module, component, apparatus, and/or system that facilitates, enables, guides, promotes, precision in the alignment of two objects by way of registration. In one aspect a registration key can include a surface and one or more recesses and/or features of that surface that are configured to fit within corresponding recesses, projections, and/or other features of another structure such as another surface. In one aspect a registration key can include a surface and one or more projections and/or features of, extending from, or connected to that surface that are configured to fit within corresponding recesses, projections, and/or other features of another structure such as another surface. In certain aspects, the features of the registration key may be configured to fit within, or in contact, or in close contact with those of the another structure. In one embodiment, when the two structures align the registration key has served its purpose.

“Shelf” refers to a narrow horizontal surface or structure projecting from a side, surface, structure, wall, cliff, or other surface of a structure. (Search “shelf” on wordhippo.com. WordHippo, 2023. Web. Accessed 16 Aug. 2023. Modified.)

“Section” refers to a separate part, portion, or area of a structure, object, device, apparatus, or container. (Search “section” on wordhippo.com. WordHippo, 2023. Web. Accessed 16 Aug. 2023. Modified.)

“Leg” refers to a part or portion of another structure. Often, a leg can be a narrow, elongated structure resembling a leg of a human.

As used herein, a “resection” refers to a method, procedure, or step that removes tissue from another anatomical structure or body. A resection can include an osteotomy that cuts through a bone or other tissue because the osteotomy still removes at least a minimal amount of tissue. A resection is typically performed by a surgeon on a part of a body of a patient. A resection is a type of osteotomy. (Search “surgery” on Wikipedia.com May 26, 2021. CC-BY-SA 3.0 Modified. Accessed May 26, 2021.) Resection may be used as a noun or a verb. In the verb form, the term is “resect” and refers to an act of performing, or doing, a resection. Past tense of the verb resect is resected.

“Anatomical structure” refers to any part or portion of a part of a body of a person, animal, or other patient. Examples of anatomical structures, include but are not limited to, a bone, bones, soft tissue, a joint, joints, a tissue surface, a protrusion, a recess, an opening, skin, hard tissue, teeth, mouth, eyes, hair, nails, fingers, toes, legs, arms, torso, vertebrae, ligaments, tendons, organs, or the like.

“Anatomical reference” refers to any reference(s) that is, or is on, or is in, or is otherwise associated, with an anatomical structure. Examples of anatomical structures, include but are not limited to, a bone, bones, soft tissue, a joint, joints, skin, hard tissue, teeth, mouth, eyes, hair, nails, fingers, toes, legs, arms, torso, vertebrae, ligaments, tendons, organs, a hole, a post, a plurality of holes, a plurality of posts, a fastener, a suture, a clamp, an instrument, an implant, or the like.

As used herein, a “condition” refers to a state of something with regard to its appearance, quality, or working order. In certain aspects, a condition may refer to a patient’s state of health or physical fitness or the state of health or physical fitness of an organ or anatomical part of a patient. In certain embodiments, a condition may refer to an illness, pain, discomfort, defect, disease, or deformity of a patient or of an organ or anatomical part of a patient. (Search “condition” on wordhippo.com. WordHippo, 2021. Web. Accessed 8 Dec. 2021. Modified.)

“Bone condition” refers to any of a variety of conditions of bones of a patient. Generally, a bone condition refers to an orientation, position, and/or alignment of one or more bones of the patient relative to other anatomical structures of the body of the patient. Bone conditions may be caused by or result from deformities, misalignment, malrotation, fractures, joint failure, and/or the like. A bone condition includes, but is not limited to, any angular deformities of one or more bone segments in either the lower or upper extremities (for example, tibial deformities, calcaneal deformities, femoral deformities, and radial deformities). Alternatively, or in addition, “bone condition” can refer to the structural makeup and configuration of one or more bones of a patient. Thus bone condition may refer to a state or condition of regions, a thickness of a cortex, bone density, a thickness and/or porosity of internal regions (e.g. whether it is calcaneus or solid) of the bone or parts of the bone such as a head, a base, a shaft, a protuberance, a process, a lamina, a foramen, and the like of a bone, along the metaphyseal region, epiphysis region, and/or a diaphyseal region. “Malrotation” refers to a condition in which a part, typically a part of a patient’s body has rotated from a normal position to an unnormal or uncommon position.

As used herein, a “guide” refers to a part, component, member, or structure designed, adapted, configured, or engineered to guide or direct one or more other parts, components, or structures. A guide may be part of, integrated with, connected to, attachable to, or coupled to, another structure, device, or instrument. In one embodiment, a guide may include a modifier that identifies a particular function, location, orientation, operation, type, and/or a particular structure of the guide. Examples of such modifiers applied to a guide, include, but are not limited to, “pin guide” that guides or directs one or more pins, a “cutting guide” that guides or directs the making or one or more cuts, a placement, deployment, or insertion guide that guides or directs the placement, positioning, orientation, deployment, installation, or insertion of a fastener and/or implant, a “cross fixation guide” that guides deployment of a fastener or fixation member, an “alignment guide” that guides the alignment of two or more objects or structures, a “navigation guide” that guides a user in navigating a course or process or procedure such as a surgical procedure, a “resection guide” that serves to guide resection of soft or hard tissue, such as in an osteotomy, a “reduction guide” can serve to guide reduction of one or more bone segments or fragments, an "placement guide" that serves to identify how an object can be placed in relation to another object or structure, and the like. Furthermore, guides may include modifiers applied due to the procedure or location within a patient for which the guide is to be used. For example, where a guide is used at a joint, the guide may be referred to herein as an "arthrodesis guide."

Those of skill in the art will appreciate that a resection feature may take a variety of forms and may include a single feature or one or more features that together form the resection feature. In certain embodiments, the resection feature may take the form of one or more slots or cut channels. Alternatively, or in addition, a resection feature may be referenced using other names including, but not limited to, channel, cut channels, and the like.

"Cross section" or "cross-section" refers to the non-empty intersection of a body in three-dimensional space with a plane, or the analog in higher-dimensional spaces. (Search "cross section" on Wikipedia.com Mar. 7, 2022. Modified. Accessed Sep. 21, 2022.)

As used herein, "intersection" refers to a point, plane, line, or area where two or more other points, lines, planes, or areas each occupy the same space.

"Turn" refers to a bend or curve or change in trajectory and/or direction of a road, path, river, slot, channel, or the like. (Search "turn" on wordhippo.com. WordHippo, 2023. Web. Accessed 16 Aug. 2023. Modified.)

"Cut channel" refers to a channel, slot, hole, or opening, configured to facilitate making a cut. In certain embodiments, a cut channel is one example of a resection feature, resection member, and/or resection guide. "Rotation slot" refers to a channel, slot, hole, or opening, configured to facilitate rotating one structure in relation to another structure.

As used herein, "slot" refers to a narrow opening or groove. (search "slot" on Merriam-Webster.com. Merriam-Webster, 2021. Web. 4 Aug. 2021. Modified.)

"Vertex" refers to a point at which lines, structures, trajectories, or pathways intersect. (Search "vertex" on wordhippo.com. WordHippo, 2023. Web. Modified. Accessed 13 Jun. 2023.)

"Hole" refers to a gap, an opening, an aperture, a port, a portal, a space or recess in a structure, a void in a structure, or the like. In certain embodiments, a hole can refer to a structure configured specifically for receiving something and/or for allowing access. In certain embodiments, a hole can pass through a structure. In other embodiments, an opening can exist within a structure but not pass through the structure. A hole can be two-dimensional or three-dimensional and can have a variety of geometric shapes and/or cross-sectional shapes, including, but not limited to a rectangle, a square, or other polygon, as well as a circle, an ellipse, an ovoid, or other circular or semi-circular shape. As used herein, the term "hole" can include one or more modifiers that define specific types of "holes" based on the purpose, function, operation, position, or location of the "hole." As one example, a "fastener hole" refers to an "hole" adapted, configured, designed, or engineered to accept or accommodate a "fastener."

As used herein, an "opening" refers to a gap, a hole, an aperture, a port, a portal, a slit, a space or recess in a structure, a void in a structure, or the like. In certain embodiments, an opening can refer to a structure configured specifically for receiving something and/or for allowing access. In certain embodiments, an opening can pass through a structure. In such embodiments, the opening can be referred to as a window. In other embodiments, an opening can exist within a structure but not pass through the structure. In other embodiments, an opening can initiate on a surface or at an edge or at a side of a structure and extend into the structure for a distance, but not pass through or extend to another side or edge of the structure. In other embodiments, an opening can initiate on a surface or at an edge or at a side of a structure and extend into the structure until the opening extends through or extends to another side or edge of the structure. An opening can be two-dimensional or three-dimensional and can have a variety of geometric shapes and/or cross-sectional shapes, including, but not limited to a rectangle, a square, or other polygon, as well as a circle, an ellipse, an ovoid, or other circular or semi-circular shape. As used herein, the term "opening" can include one or more modifiers that define specific types of "openings" based on the purpose, function, operation, position, or location of the "opening." As one example, a "fastener opening" refers to an "opening" adapted, configured, designed, or engineered to accept or accommodate a "fastener."

As used herein, an "interface," "user interface," or "engagement interface" refers to an area, a boundary, or a place at which two separate and/or independent structures, members, apparatus, assemblies, components, and/or systems join, connect, are coupled, or meet and act on, or communicate, mechanically and/or electronically, with each other. In certain embodiments, "interface" may refer to a surface forming a common boundary of two bodies, spaces, structures, members, apparatus, assemblies, components, or phases. (search "interface" on Merriam-Webster.com. Merriam-Webster, 2021. Web. 15 Nov. 2021. Modified.) In certain embodiments, the term interface may be used with an adjective that identifies a type or function for the interface. For example, an engagement or coupling interface may refer to one or more structures that interact, connect, or couple to mechanically join or connect two separate structures, each connected to a side of the interface. In another example, a user interface may refer to one or more mechanical, electrical, or electromechanical structures that interact with or enable a user to provide user input, instructions, input signals, data, or data values and receive output, output data, or feedback.

"Resection interface" refers to an interface between a resected portion of tissue and another object, structure, or thing. Often a resection interface is an interface or boundary between one resected portion of an anatomical structure and another resected portion of another anatomical structure. The two anatomical structures can be portions, parts, or fragments of one anatomical structure or two different anatomical structures. A resection interface can be embodied in a variety of shapes and/or configurations, including a point, a line, a plane, a contour, a boundary, or the like. In one embodiment, a resection interface is an interface between two or more cut planes or two or more cut surfaces or two or more cut faces.

"Cortical bone" refers to a type of bone tissue. Cortical bone is a type of bone tissue typically found between an external surface of a bone and an interior area of the bone. Cortical bone is more dense and typically stronger structurally than other types of bone tissue. "Cortical surface" refers to a surface of cortical bone.

"Cortex" refers to an area of bone that extends from an external surface of the bone towards a center part of the bone. The cortex is typically comprised of cortical bone.

"Transosseous placement feature" refers to a placement feature that extends through one or more bones and that enables, or facilitates, placement of another device, apparatus, or instrument.

"Patient specific feature" refers to a feature, function, structure, device, guide, tool, instrument, apparatus, member, component, system, assembly, module, or subsystem that is adjusted, tailored, modified, organized, configured, designed, arranged, engineered, and/or fabricated to specifically address the anatomy, physiology, condition, abnormalities, needs, or desires of a particular patient or surgeon serving the particular patient. In one aspect, a patient specific feature is unique to a single patient and may include features unique to the patient such as a number of cut channels, a number of bone attachment features, a number of bone engagement surfaces, a number of resection features, a depth of one or more cutting channels, an angle for one or more resection channels, a surface contour, component position, component orientation, and/or other features. "Medial resection guide" refers to a resection guide designed, engineered, fabricated, or intended for use with, one, in, or about a medial part, section, surface, portion, or aspect of an anatomical structure such as a bone, digit, limb, or other anatomical structure for one or more steps of a resection procedure. "Lateral resection guide" refers to a resection guide designed, engineered, fabricated, or intended for use with, one, in, or about a lateral part, section, surface, portion, or aspect of an anatomical structure such as a bone, digit, limb, or other anatomical structure for one or more steps of a resection procedure.

"Prescription" or "Prescribed" refers to a written order, as by a physician or nurse practitioner, for the administration of a medicine, preparation of an implant, preparation of an instrument, or other intervention. Prescription can also refer to the prescribed medicine or intervention. (Search "prescription" on wordhippo.com. WordHippo, 2023. Web. Accessed 3 May 2023. Modified.)

As used herein, "end" refers to a part or structure of an area or span that lies at the boundary or edge. An end can also refer to a point that marks the extent of something and/or a point where something ceases to exist. An end can also refer to an extreme or last part lengthwise of a structure or surface. (search "end" on Merriam-Webster.com. Merriam-Webster, 2021. Web. 4 Aug. 2021. Modified.)

As used herein, "edge" refers to a structure, boundary, or line where an object, surface, or area begins or ends. An edge can also refer to a boundary or perimeter between two structures, objects, or surfaces. An edge can also refer to a narrow part adjacent to a border. (search "edge" on Merriam-Webster.com. Merriam-Webster, 2021. Web. 3 Aug. 2021. Modified.) In certain embodiments, an edge can be a one dimensional or a two dimensional structure that joins two adjacent structures or surfaces. Furthermore, an edge may be at a perimeter of an object or within a perimeter or boundary of an object.

"Bone fragment" refers to a part of a bone that is normally part of another bone of a patient. A bone fragment may be separate from another bone of a patient due to a deformity or trauma. In one aspect, the bone the bone fragment is normally connected or joined with is referred to as a parent bone.

"Joint" or "Articulation" refers to the connection made between bones in a human or animal body which link the skeletal system to form a functional whole. Joints may be biomechanically classified as a simple joint, a compound joint, or a complex joint. Joints may be classified anatomically into groups such as joints of hand, elbow joints, wrist joints, axillary joints, sternoclavicular joints, vertebral articulations, temporomandibular joints, sacroiliac joints, hip joints, knee joints, ankle joints, articulations of foot, and the like. (Search "joint" on Wikipedia.com Dec. 19, 2021. CC-BY-SA 3.0 Modified. Accessed Jan. 20, 2022.)

"Tarso-metatarsal joint" or "TMT joint" refers to a joint of a patient between a metatarsal bone and one or more cuneiform/tarsal/cuboid bones. The TMT joint may also be referred to as a "Lis Franc" or "Lisfranc" joint after a French surgeon Lisfranc.

"Cut surface" refers to a surface of an object that is created or formed by the removal of one or more parts of the object that includes the original surface. Cut surfaces can be created using a variety of methods, tools, or apparatuses and may be formed using a variety of removal actions, including, but not limited to, fenestrating, drilling, abrading, cutting, sawing, chiseling, digging, scrapping, and the like. Tools and/or methods used for forming a cut surface can include manual, mechanical, motorized, hydraulic, automated, robotic, and the like. In certain embodiments, the cut surface(s) are planar.

"Orientation" refers to a direction, angle, position, condition, state, or configuration of a first object, component, part, apparatus, system, or assembly relative to another object, component, part, apparatus, system, assembly, reference point, reference axis, or reference plane.

"Longitudinal axis" or "Long axis" refers to an axis of a structure, device, object, apparatus, or part thereof that extends from one end of a longest dimension to an opposite end. Typically, a longitudinal axis passes through a center of the structure, device, object, apparatus, or part thereof along the longitudinal axis. The center point used for the longitudinal axis may be a geometric center point and/or a mass center point.

"Mechanical axis" refers to an axis of a long bone such as a femur or tibia. The mechanical axis of a long bone is a straight line connecting the joint center points of the proximal and distal joint regions, whether in the frontal or sagittal plane. A mechanical axis can be useful in defining how the mechanical (weight, gait, flexion, extension, etc.) forces impact the morphology of the bone structure. A mechanical axis and anatomical axis can both help in the surgical planning in relation to deformed bones. (Search "axes of the long bones" on appropedia.com; Amit Dinanath Maurya, OpenSurgiSim (2021-2023). "Axes of the long bones-Mechanical and Anatomical". SELF. Modified. Accessed Jun. 28, 2023.)

As used herein, a "drive", "drive feature", or "drive recess" refers to an apparatus, instrument, structure, member, device, component, system, or assembly structured, organized, configured, designed, arranged, or engineered to receive a torque and transfer that torque to a structure connected or coupled to the drive. At a minimum, a drive is a set of shaped cavities and/or protrusions on a structure that allows torque to be applied to the structure. Often, a drive includes a mating tool, known as a driver. For example, cavities and/or protrusions on a head of a screw are one kind of drive and an example of a corresponding mating tool is a screwdriver, that is used to turn the screw, the drive. Examples of a drive include but are not limited to screw drives such as slotted drives, cruciform drives, square drives, multiple square drives, internal polygon, internal hex drives, penta lobular sockets, hex lobular sockets, combination drives, external drives, tamper-resistant drives, and the like. (Search 'list of screw drives' on Wikipedia.com Mar. 12, 2021. Modified. Accessed Mar. 19, 2021.)

"Thread" or "threads" refers to a helical structure used to convert between rotational and linear movement or force. A thread is a ridge wrapped around a cylinder or cone in the form of a helix, with the ridge wrapped around the cylinder being called a straight thread and the ridge wrapped around the cone called a tapered thread. Straight threads or tapered threads are examples of external threads, also referred to as male threads. Threads that a correspond to male threads are referred to as female threads and are formed within the inside wall of a matching hole, passage, or opening of a nut or substrate or other structure. A thread used with a fastener may be referred to as a screw thread and can be an important feature of a simple machine and also as a threaded fastener. The mechanical advantage of a threaded fastener depends on its lead, which is the linear distance the threaded fastener travels in one revolution. (Search 'screw thread' on Wikipedia.com Jul. 17, 2022. Modified. Accessed Aug. 1, 2022.)

"Cutting tool" refers to any tool that can be used to cut or resect another object. In particular, a cutting tool can refer to a manual or power tool for cutting or resecting tissue of a patient. Examples of cutting tools include, but are not limited to, a burr, an oscillating saw, a reciprocating saw, a grater saw, a drill, a mill, a side-cutting burr, or the like.

As used herein, a "shaft" refers to a long narrow structure, device, component, member, system, or assembly that is structured, organized, configured, designed, arranged, or engineered to support and/or connect a structure, device, component, member, system, connected to each end of the shaft. Typically, a shaft is configured to provide rigid support and integrity in view of a variety of forces including tensile force, compression force, torsion force, shear force, and the like. In addition, a shaft can be configured to provide rigid structural support and integrity in view of a loads including axial loads, torsional loads, transverse loads, and the like. A shaft may be oriented and function in a variety of orientations including vertical, horizontal, or any orientation between these and in two or three dimensions. A shaft may be made from a variety of materials including, but not limited to, metal, plastic, ceramic, wood, fiberglass, acrylic, carbon, biocompatible materials, biodegradable materials or the like. A shaft may be formed of any biocompatible materials, including but not limited to biocompatible metals such as Titanium, Titanium alloys, stainless steel, carbon fiber, combinations of carbon fiber and a metallic alloy, stainless steel alloys, cobalt-chromium steel alloys, nickel-titanium alloys, shape memory alloys such as Nitinol, biocompatible ceramics, and biocompatible polymers such as Polyether ether ketone (PEEK) or a polylactide polymer (e.g. PLLA) and/or others, or any combination of these materials.

"Head" refers to a device, apparatus, member, component, system, assembly, module, subsystem, circuit, or structure, organized, configured, designed, arranged, or engineered to have a prominent role in a particular feature, function, operation, process, method, and/or procedure for a device, apparatus, member, component, system, assembly, module, subsystem, circuit, or structure the includes, is coupled to, or interfaces with the head. In certain embodiments, the head may sit at the top or in another prominent position when interfacing with and/or coupled to a device, apparatus, member, component, system, assembly, module, subsystem, circuit, or structure.

As used herein, an "interface," "user interface," or "engagement interface" refers to an area, a boundary, or a place at which two separate and/or independent structures, members, apparatus, assemblies, components, and/or systems join, connect, are coupled, or meet and act on, or communicate, mechanically and/or electronically, with each other. In certain embodiments, "interface" may refer to a surface forming a common boundary of two bodies, spaces, structures, members, apparatus, assemblies, components, or phases. (search "interface" on Merriam-Webster.com. Merriam-Webster, 2021. Web. 15 Nov. 2021. Modified.) In certain embodiments, the term interface may be used with an adjective that identifies a type or function for the interface. For example, an engagement or coupling interface may refer to one or more structures that interact, connect, or couple to mechanically join or connect two separate structures, each connected to a side of the interface. In another example, a user interface may refer to one or more mechanical, electrical, or electromechanical structures that interact with or enable a user to provide user input, instructions, input signals, data, or data values and receive output, output data, or feedback.

"Cut surface" or "cut face" refers to a surface of an object that is created or formed by the removal of one or more parts of the object that includes the original surface. Cut surfaces or cut faces can be created using a variety of methods, tools, or apparatuses and may be formed using a variety of removal actions, including, but not limited to, fenestrating, drilling, abrading, cutting, sawing, chiseling, digging, scrapping, and the like. Tools and/or methods used for forming a cut surface or cut face can include manual, mechanical, motorized, hydraulic, automated, robotic, and the like.

The present disclosure discloses surgical systems and methods by which a bone condition, that can include a deformity, may be corrected or otherwise addressed. Known methods of addressing bone conditions are often limited to a finite range of discretely sized instruments. A patient with an unusual condition, or anatomy that falls between instrument sizes, may not be readily treated with such systems.

Furthermore, patient-specific instruments may be used for various other procedures on the foot, or on other bones of the musculoskeletal system. For example, patient-specific instruments and/or other instruments may be used for various procedures including resection and translation of a head of a long bone, determining where to perform an osteotomy on one or more joints or part of one or more bones, determining ligament or tendon attachment or anchoring points, determining where to form bone tunnels or position anchors, tendon or graft deployment, and the like.

FIG. 1A is a flowchart diagram depicting a method 100 for correcting a bone condition, according to one embodiment. The method 100 may be used for any of a wide variety of bone conditions, including but not limited to deformities, fractures, joint failure, and/or the like. Further, the method 100 may provide correction with a wide variety of treatments, including but not limited to arthroplasty, arthrodesis, fracture repair, and/or the like.

As shown, the method 100 may begin with a step 102 in which a CT scan (or another three-dimensional image, also referred to as medical imaging) of the patient's anatomy is obtained. The step 102 may include capturing a scan of only the particular bone(s) to be treated, or may include capture of additional anatomic information, such as the surrounding tissues. Additionally or alternatively, the step 102 may include receiving a previously captured image, for example, at a design and/or fabrication facility. Performance of the step 102 may result in possession of a three-dimensional model of the patient's anatomy, or three-dimensional surface points that can be used to construct such a three-dimensional model.

After the step 102 has been carried out, the method 100 may proceed to a step 104 in which a CAD model of the patient's anatomy (including one or more bones) is generated. The CAD model may be one example of a bone model. The CAD model may be of any known format, including but not limited to SolidWorks, Catia, AutoCAD, or DXF. In some embodiments, customized software may be used to generate the CAD model from the CT scan. The CAD model may only include the bone(s) to be treated and/or may include surrounding tissues. In alternative embodiments, the step 104 may be omitted, as the CT scan may capture data that can directly be used in future steps without the need for conversion.

In one embodiment, the CAD model generated and/or patient-specific instrumentation, implants, and/or plan for conducting an operative procedure, may be enhanced by the use of advanced computer analysis system, machine learning, and/or automated/artificial intelligence. For example, these technologies may be used to revise a set of steps for a procedure such that a more desirable outcome is achieved.

In a step 106, the CAD model and/or CT scan data may be used to model patient-specific instrumentation that can be used to correct the condition, as it exists in the patient's anatomy. In some embodiments, any known CAD program may be used to view and/or manipulate the CAD model and/or CT scan, and generate one or more instruments that are matched specifically to the size and/or shape of the patient's bone(s). In some embodiments, such instrumentation may include a targeting guide, trajectory guide, drill guide, cutting guide, tendon trajectory guide, capital fragment positioning guide, or similar guide that can be attached to one or more bones, with one or more features that facilitate work on the one or more bones pursuant to a procedure such as arthroplasty or arthrodesis. In some embodiments, performance of the step 106 may include modelling an instrument with a bone engagement surface that is shaped to match the contour of a surface of the bone, such that the bone engagement surface can lie directly on the corresponding contour.

In a step 108, the model(s) may be used to manufacture patient-specific instrumentation and/or implants. This may be done via any known manufacturing method, including casting, forging, milling, additive manufacturing, and/or the like. Additive manufacturing may provide unique benefits, as the model may be directly used to manufacture the instrumentation and/or implants (without the need to generate molds, tool paths, and/or the like beforehand). Such instrumentation may optionally include a targeting guide, trajectory guide, drill guide, cutting guide, positioner, positioning guide, tendon trajectory guide, or the like.

In addition to, or in the alternative to the step 108, the model(s) may be used to select from available sizes of implants and/or instruments or instruments having various attributes and advise the surgeon accordingly. For example, where a range of guides are available for a given procedure, analysis of the CAD data may facilitate pre-operative selection of the optimal guide and/or optimal placement of the guide on the bone. Similarly, if a range of implants and/or instruments may be used for a given procedure, analysis of the CAD data may facilitate pre-operative selection of the optimal implant(s). More particularly, properly-sized spacers, screws, bone plates, and/or other hardware may be pre-operatively selected.

Thus, the result of the step 108 may provision, to the surgeon, of one or more of the following: (1) one or more patient-specific instruments; (2) one or more patient-specific implants; (3) an instrument, selected from one or more available instrument sizes and/or configurations; (4) an implant, selected from one or more available implant sizes and/or configurations; (5) instructions for which instrument(s) to select from available instrument sizes and/or configurations; (6) instructions for which implant(s) to select from available implant sizes and/or configurations; (7) instructions for proper positioning or anchorage of one or more instruments to be used in the procedure; and (8) instructions for proper positioning or anchorage of one or more implants to be used in the procedure. These items may be provided to the surgeon directly, or to a medical device company or representative, for subsequent delivery to the surgeon.

In a step 110, the manufactured instrumentation may be used in surgery to facilitate treatment of the condition. In some embodiments, this may include placing the modelled bone engagement surface against the corresponding contour of the bone used to obtain its shape, and then using the resection feature(s) to guide resection of one or more bones. Then the bone(s) may be further treated, for example, by attaching one or more joint replacement implants (in the case of joint arthroplasty), or by attaching bone segments together (in the case of arthrodesis or fracture repair). Prior to completion of the step 110, the instrumentation may be removed from the patient, and the surgical wound may be closed.

As mentioned previously, the method 100 may be used to correct a wide variety of bone conditions. One example of the method 100 will be shown and described in connection with FIG. 1B, for correction of a bunion deformity of the foot.

In certain embodiments, one or more of a method, apparatus, and/or system of the disclosed solution can be used for training a surgeon to perform a patient-specific procedure or technique. In one embodiment, the CAD model generated and/or patient-specific instrumentation, implants, and/or plan for conducting an operative procedure can be used to train a surgeon to perform a patient-specific procedure or technique.

In one example embodiment, a surgeon may submit a CT scan of a patient's foot to an apparatus or system that implements the disclosed solution. Next, a manual or automated process may be used to generate a CAD model and for making the measurements and correction desired for the patient. In the automated process, an advanced computer analysis system, machine learning and automated/artificial intelligence may be used to generate a CAD model and/or one or more patient-specific instruments and/or operation plans. For example, a patient-specific instrument may be fabricated that is registered to the patient's anatomy using a computer-aided machine (CAM) tool. In addition, a CAM tool may be used to fabricate a 3D structure representative of the patient's anatomy, referred to herein as a patient-specific synthetic cadaver. (e.g. one or more bones of a patient's foot). Next, the patient-specific instrument and the patient-specific synthetic cadaver can be provided to a surgeon who can then rehearse an operation procedure in part or in full before going into an operating room with the patient.

In certain embodiments, the patient-specific instrument or instrument can be used to preposition and/or facilitate pre-drilling holes for a plate system for fixation purposes. Such plate systems may be optimally placed, per a CT scan, after a correction procedure for optimal fixation outcome. In another embodiment, the CAD model and/or automated process such as advanced computer analysis, machine learning and automated/artificial intelligence may be used to measure a depth of the a through a patient-specific resection guide for use with robotics apparatus and/or systems which would control the depth of each cut within the guide to protect vital structures below or adjacent to a bone being cut. In another embodiment, the CAD model and/or automated process such as advanced computer analysis, machine learning and automated/artificial intelligence may be used to define desired fastener (e.g. bone screw) length and/or trajectories through a patient-specific instrument and/or implant. The details for such lengths, trajectories, and components can be detailed in a report provided to the surgeon preparing to perform a procedure.

Figure 1B:
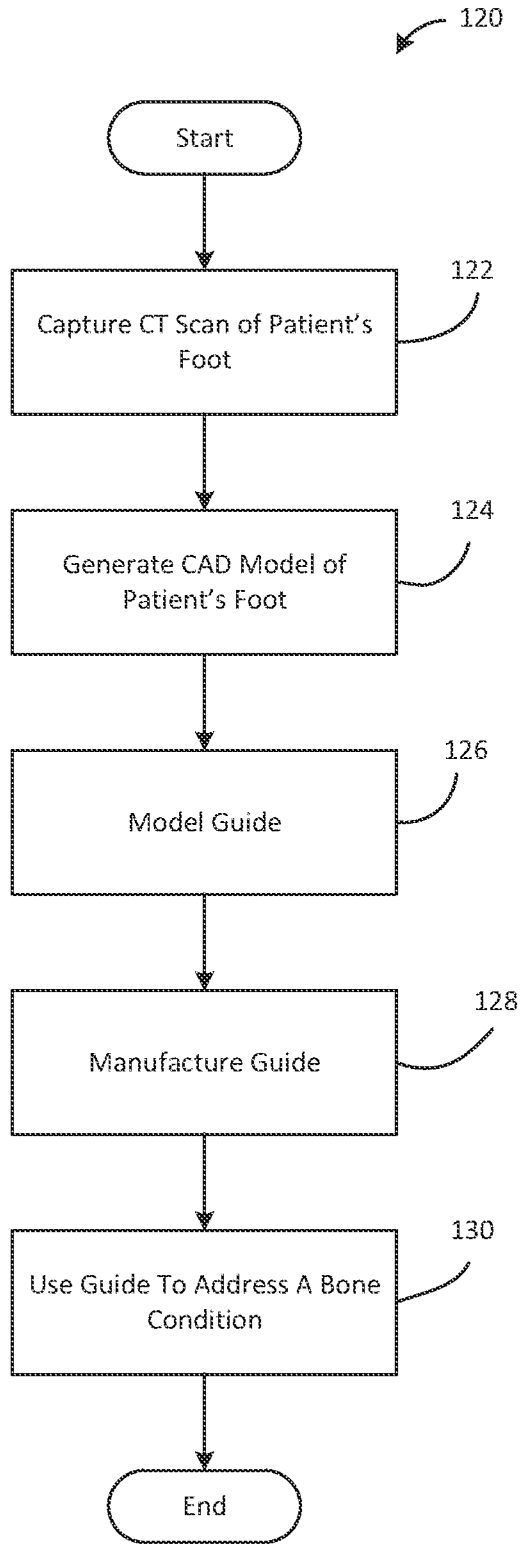
FIG. 1B is a flowchart diagram depicting a method for remediating a condition, according to one embodiment.

FIG. 1B is a flowchart diagram depicting a method 120 for correcting or remediating a bone condition, according to one embodiment. The method 120 may be used to prepare for an orthopedic procedure which corrects or remediates a bone, muscle, deformity, and/or tendon condition of a patient.

As shown, the method 120 may begin with a step 122 in which a CT scan (or another three-dimensional image) of the patient's foot is obtained. The step 122 may include capturing a scan of select bones of a patient or may include capturing additional anatomic information, such as the entire foot. Additionally or alternatively, the step 122 may include receipt of previously captured image data. Capture of the entire foot in the step 122 may facilitate proper alignment of the first metatarsal with the rest of the foot (for example, with the second metatarsal). Performance of the step 122 may result in generation of a three-dimensional model of the patient's foot, or three-dimensional surface points that can be used to construct such a three-dimensional model.

After the step 122 has been carried out, the method 120 may proceed to a step 124 in which a CAD model of the relevant portion of the patient's anatomy is generated. The CAD model may optionally include the bones of the entire foot, like the CT scan obtained in the step 122. In alternative embodiments, the step 124 may be omitted in favor of direct utilization of the CT scan data, as described in connection with the step 104.

In a step 126, the CAD model and/or CT scan data may be used to model patient-specific instrumentation that can be used to correct or remediate a bone condition. Such instrumentation may include a guide. In one example, the guide can seat or abut or contact a surface of a bone and including an opening that guides a trajectory for a fastener for a procedure. In some embodiments, performance of the step 126 may include modelling the guide with a bone engagement surface that is shaped to match contours of the surfaces of the bone, such that the bone engagement surface can lie directly on the corresponding contours of the bone.

In a step 128, the model(s) may be used to manufacture patient-specific instrumentation and/or instruments. This may include manufacturing an instrument with the bone engagement surface and/or other features as described above. As in the step 108, the step 128 may additionally or alternatively involve provision of one or more instruments and/or implants from among a plurality of predetermined configurations or sizes. Further, the step 128 may additionally, or alternatively, involve provision of instructions for placement and/or anchorage of one or more instruments and/or instruments to carry out the procedure.

In a step 130, the manufactured instrument may be used in surgery to facilitate treatment of the condition. In certain embodiments, a bone engagement surface of the instrument may be placed against the corresponding contours of the bone. The instrument may include an opening and/or trajectory guide to guide insertion of a trajectory guide such as a temporary fastener such as a K-wire. The instrument may then be removed, and the remaining steps of a surgical procedure performed.

Method 100 and method 120 are merely exemplary. Those of skill in the art will recognize that various steps of the method 100 and the method 120 may be reordered, omitted, and/or supplemented with additional steps not specifically shown or described herein.

As mentioned previously, the method 120 is one species of the method 100; the present disclosure encompasses many different procedures, performed with respect to many different bones and/or joints of the body. Exemplary steps and instrumentation for the method 120 will further be shown and described in connection with the present disclosure. Those of skill in the art will recognize that the method 120 may be used in connection with different instruments; likewise, the instruments of the present disclosure may be used in connection with methods different from the method 100 and the method 120.

Figure 2A:
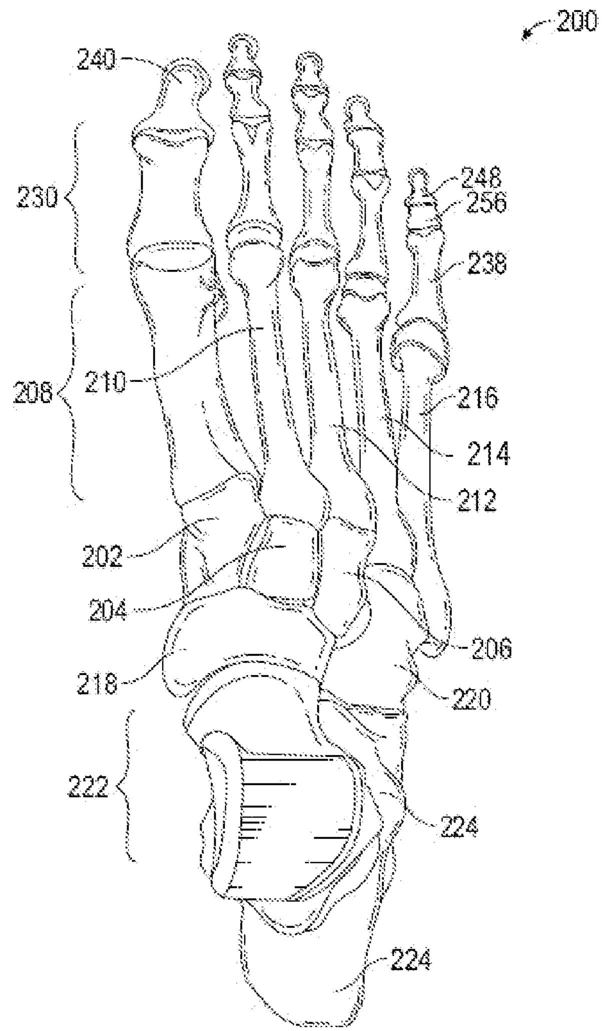
FIG. 2A is a dorsal perspective view of bones of a foot.

FIG. 2A is a perspective dorsal view of a foot 200. The foot 200 may have a medial cuneiform 202, an intermediate cuneiform 204, lateral cuneiform 206, a first metatarsal 208, a second metatarsal 210, third metatarsal 212, fourth metatarsal 214, fifth metatarsal 216, navicular 218, cuboid 220, talus 222, and calcaneus 224, among others. The medial cuneiform 202 and the intermediate cuneiform 204 may be joined together at a first metatarsocuneiform joint, and the first metatarsal 208 and the second metatarsal 210 may be joined together at a second metatarsocuneiform joint. The foot 200 includes a set of proximal phalanges numbered first through fifth (230, 232, 234, 236, 238) and a set of distal phalanges numbered first through fifth (240, 242, 244, 246, 248) and a set of middle phalanges numbered second through fifth (250, 252, 254, 256).

Figure 2B:
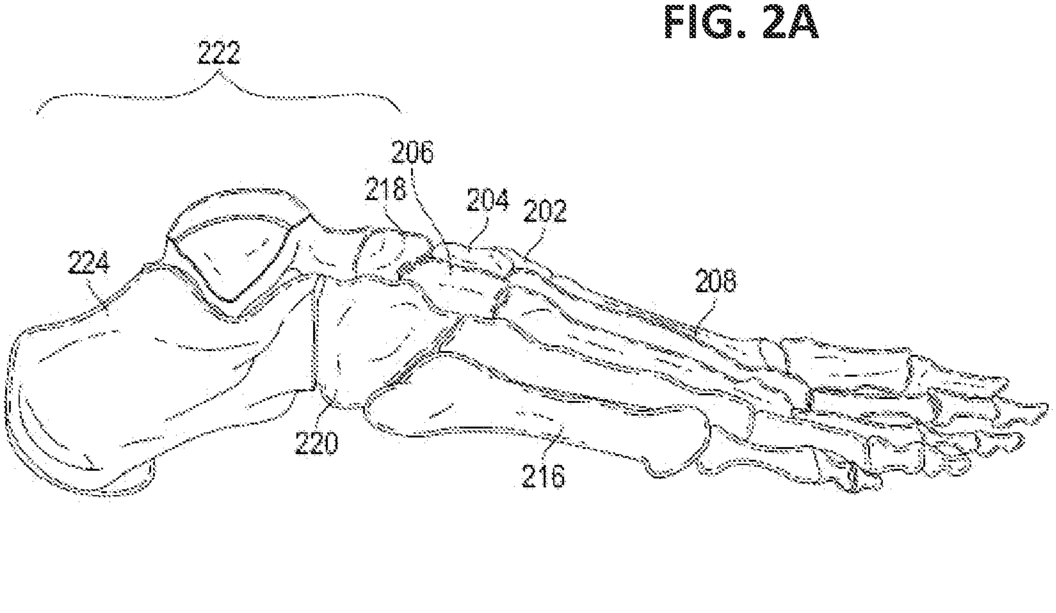
FIG. 2B is a lateral perspective view of bones of a foot.

FIG. 2B is a perspective lateral view of a foot 200, with bones of the foot labeled.

Figure 2C:
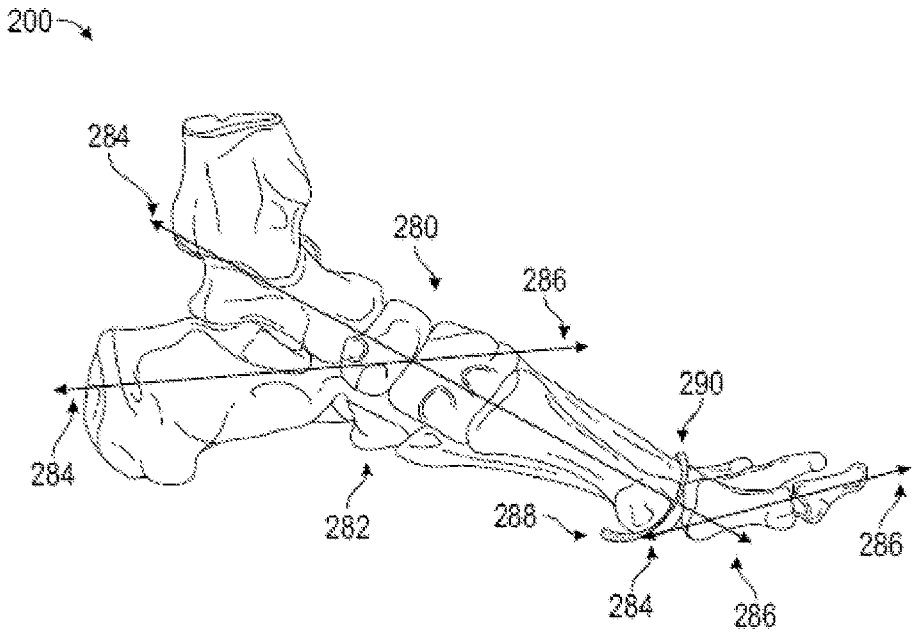
FIG. 2C is a medial perspective view of bones of a foot.
Figure 2D:
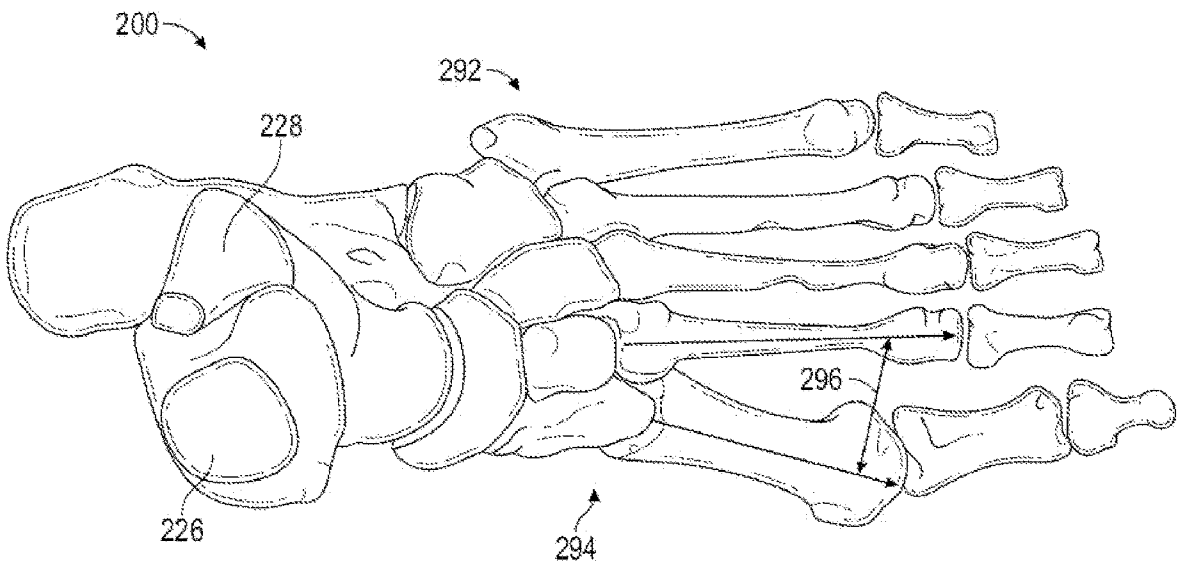
FIG. 2D is a dorsal perspective view of bones of a foot.

FIG. 2C is a perspective medial view of a foot illustrating a dorsal side 280 and a plantar side 282. The foot 200, as illustrated, may have a tibia 226 and a fibula 228, among others. Dorsal refers to the top of the foot. Plantar refers to the bottom of the foot. Proximal 284 is defined as "closer to the primary attachment point". Distal 286 is defined as "further away from the attachment point". Plantar-flex or plantarflexion 288 means movement toward the plantar side 282 of a foot or hand, toward the sole or palm. Dorsiflex or dorsiflexion 290 means movement toward the dorsal side 280 of a foot or hand, toward the top. FIG. 2D is a perspective dorsal view of the foot 200. A transverse plane is the plane that shows the top of the foot. A lateral side 292 means a side furthest away from the midline of a body, or away from a plane of bilateral symmetry of the body. A medial side 294 means a side closest to the midline of a body, or toward a plane of bilateral symmetry of the body. For a Lapidus procedure, the intermetatarsal (IM) angle 296 is the angle to be corrected to remove the hallux valgus (bunion) deformity.

Figure 2E:
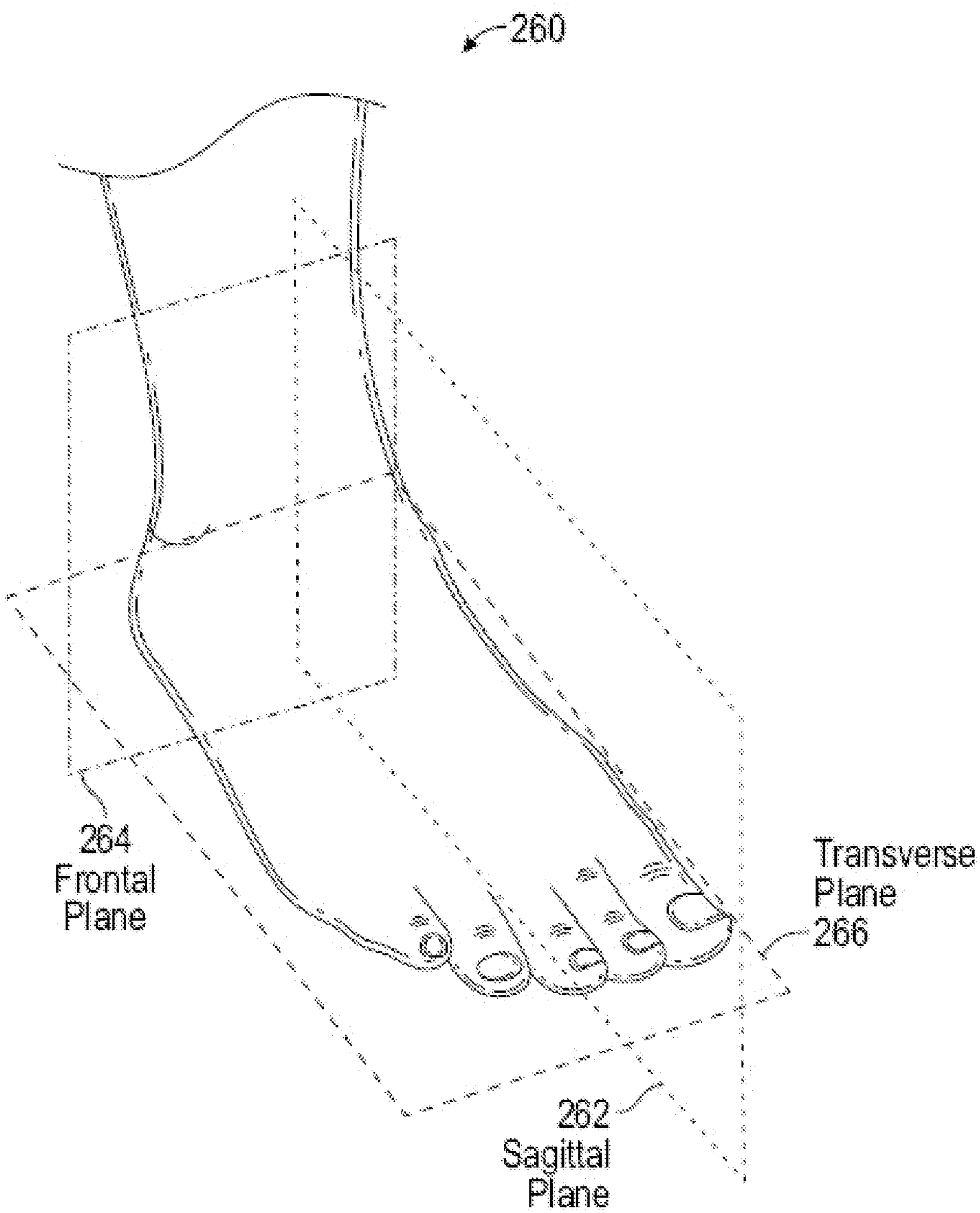
FIG. 2E is a view of a foot illustrating common planes of reference for a human foot.

FIG. 2E is a view of a foot illustrating common planes 260 of reference for a human foot. FIG. 2E illustrates a sagittal plane 262 that divides the foot into a right section and a left section half. The sagittal plane 262 is perpendicular to frontal or coronal plane 264 and the transverse plane 266. In the foot, the frontal plane 264 generally runs vertically through the ankle and the transverse plane 266 generally runs horizontally through the midfoot and toes of the foot.

Every patient and/or condition is different; accordingly, the degree of angular adjustment needed in each direction may be different for every patient. Use of a patient-specific instrument may help the surgeon obtain an optimal realignment, target, or position a bone tunnel, position one or more resections and/or fasteners and the like. Thus, providing patient-specific instruments, jigs, and/or instrumentation may provide unique benefits.

The present patient-specific instrumentation may be used to correct a wide variety of conditions. Such conditions include, but are not limited to, angular deformities of one bone in either the lower or upper extremities (for example, tibial deformities, calcaneal deformities, femoral deformities, and radial deformities). The present disclosure may also be used to treat an interface between two bones (for example, the ankle joint, metatarsal cuneiform joint, lisfranc's joint, complex Charcot deformity, wrist joint, knee joint, etc.). As one example, an angular deformity or segmental malalignment in the forefoot may be treated, such as is found at the metatarsal cuneiform level, the midfoot level such as the navicular cuneiform junction, hindfoot at the calcaneal cuboid or subtalar joint or at the ankle between the tibia and talar junction. Additionally, patient-specific instruments could be used in the proximal leg between two bone segments or in the upper extremity such as found at the wrist or metacarpal levels.

Figure 3:
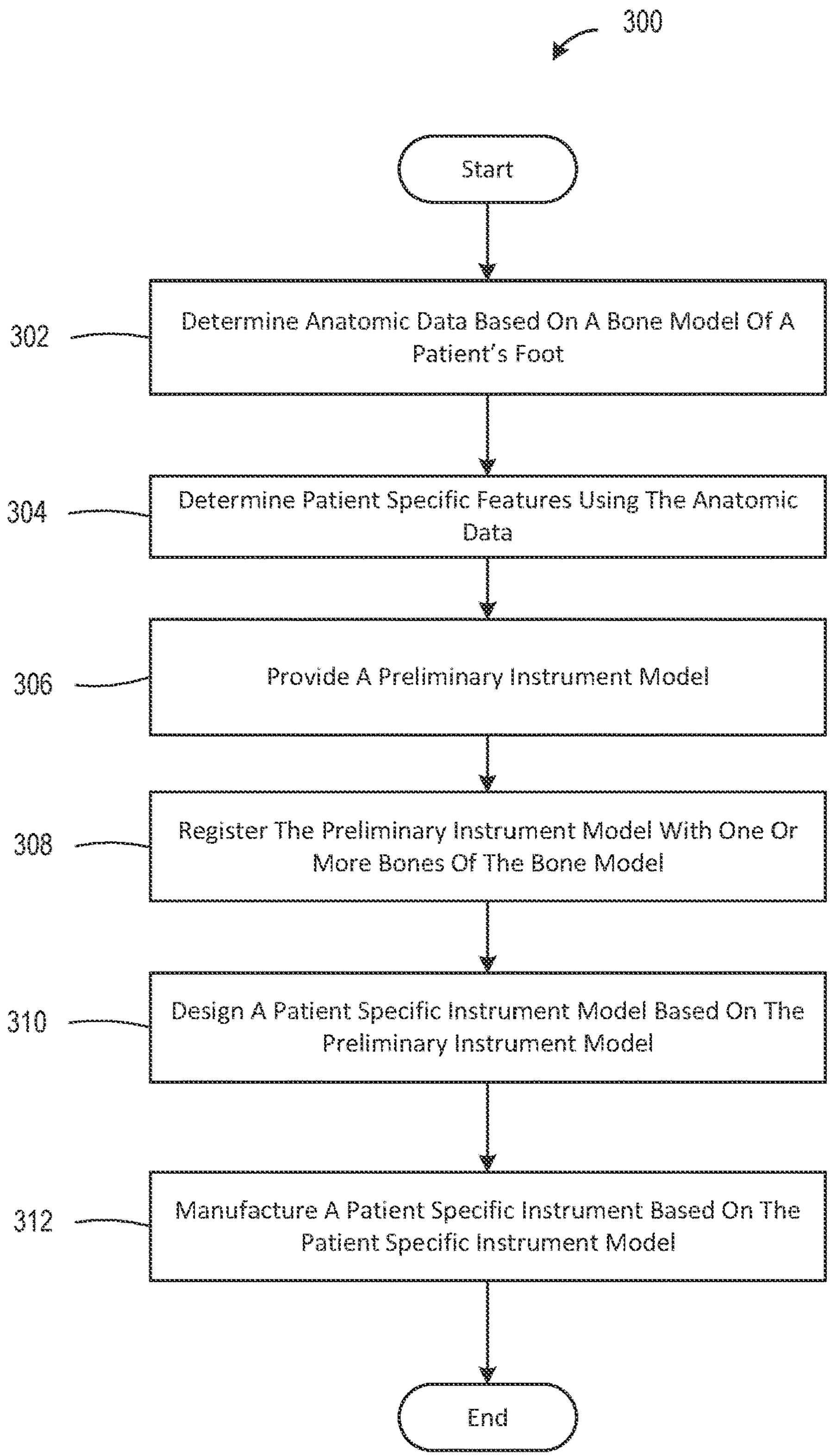
FIG. 3 is a flowchart diagram depicting a method for generating one or more patient-specific instruments, according to one embodiment.

FIG. 3 illustrates a flowchart diagram depicting a method 300 for generating one or more instruments (which may or may not be patient-specific) configured to correct or address a bone or foot condition, according to one embodiment. Prior to steps of the method 300, a bone model (also referred to as CAD model above) is generated. The bone model may be generated using medical imaging of a patient's foot and may also be referred to as an anatomic model. The medical imaging image(s) may be used by computing devices to generate patient imaging data. The patient imaging data may be used to measure and account for orientation of one or more structures of a patient's anatomy. In certain embodiments, the patient imaging data may serve, or be a part of, anatomic data for a patient.

In one embodiment, the method 300 begins after a bone model of a patient's body or body part(s) is generated. In a first step 302, the method 300 may review the bone model and data associated with the bone model to determine anatomic data of a patient's foot.

After step 302, the method 300 may determine 304 one or more angles (e.g., trajectory angle) and/or patient-specific features for a procedure using the anatomic data. "Trajectory angle" refers to a recommended angle for deployment of an instrument, graft, body part, or resection feature angle relative to a bone of a patient for a procedure. In certain embodiments, determining steps, instruments, and/or implants for a corrective procedure may employ an advanced computer analysis system, expert systems, machine learning, and/or automated/artificial intelligence.

Next, the method 300 may proceed and a preliminary instrument model is provided 306 from a repository of template models. A preliminary instrument model is a model of a preliminary instrument.

As used herein, "preliminary instrument" refers to an instrument configured, designed, and/or engineered to serve as a template, prototype, archetype, or starting point for creating, generating, or fabricating a patient-specific instrument. In one aspect, the preliminary instrument may be used, as-is, without any further changes, modifications, or adjustments and thus become a patient-specific instrument. In another aspect, the preliminary instrument may be modified, adjusted, or configured to more specifically address the goals, objectives, or needs of a patient or a surgeon and by way of the modifications become a patient-specific instrument. The patient-specific instrument can be used by a user, such as a surgeon, to guide steps in a surgical procedure, such as an osteotomy, graft harvest (e.g., autograft, allograft, or xenograft), minimally invasive surgical (MIS) procedure, and/or a tendon transfer procedure. Accordingly, a preliminary instrument model can be used to generate a patient-specific instrument. The patient-specific instrument model may be used in a surgical procedure to facilitate one or more steps of the procedure, and may be used to generate a patient-specific instrument that can be used in a surgical procedure for the patient.

In certain embodiments, the preliminary instrument model may be generated based on anatomic data and/or a bone model or a combination of these, and no model or predesigned structure, template, or prototype. Alternatively, or in addition, the preliminary instrument model may be, or may originate from, a template instrument model selected from a set of template instrument models. Each model in the set of template instrument models may be configured to fit an average patient's foot. The template instrument model may subsequently be modified or revised by an automated process or manual process to generate the preliminary instrument model used in this disclosure.

As used herein, "template instrument" refers to an instrument configured, designed, and/or engineered to serve as a template for creating, generating, or fabricating a patient-specific instrument. In one aspect, the template instrument may be used, as-is, without any further changes, modifications, or adjustments and thus become a patient-specific instrument. In another aspect, the template instrument may be modified, adjusted, or configured to more specifically address the goals, objectives, or needs of a patient or a surgeon and by way of the modifications become a patient-specific instrument. The patient-specific instrument can be used by a user, such as a surgeon, to guide making one or more resections of a structure, such as a bone for a procedure. Accordingly, a template instrument model can be used to generate a patient-specific instrument model. The patient-specific instrument model may be used in a surgical procedure to address, correct, or mitigate effects of the identified deformity and may be used to generate a patient-specific instrument that can be used in a surgical procedure for the patient.

Next, the method 300 may register 308 the preliminary instrument model with one or more bones of the bone model. This step 308 facilitates customization and modification of the preliminary instrument model to generate a patient-specific instrument model from which a patient-specific instrument can be generated. The registration step 308 may combine two models and/or patient imaging data and position both models for use in one system and/or in one model.

Next, the method 300 may design 310 a patient-specific instrument and/or procedure model based on the preliminary instrument model. The design step 310 may be completely automated or may optionally permit a user to make changes to a preliminary instrument model or partially completed patient-specific instrument model before the patient-specific instrument model is complete. A preliminary instrument model and patient-specific instrument model are two examples of an instrument model. As used herein, "instrument model" refers to a model, either physical or digital, that represents an instrument, tool, apparatus, or device. Examples, of an instrument model can include a cutting instrument model, a resection instrument model, an alignment instrument model, a reduction instrument model, a patient-specific tendon trajectory instrument model, graft harvesting instrument model, minimally invasive surgical (MIS) positioner model, or the like. In one embodiment, a patient-specific instrument and a patient-specific instrument model may be unique to a particular patient and that patient's anatomy and/or condition.

The method 300 may conclude by a step 312 in which a patient-specific instrument may be manufactured based on the patient-specific instrument model. Various manufacturing tools, devices, systems, and/or techniques can be used to manufacture the patient-specific instrument.

Figure 4:
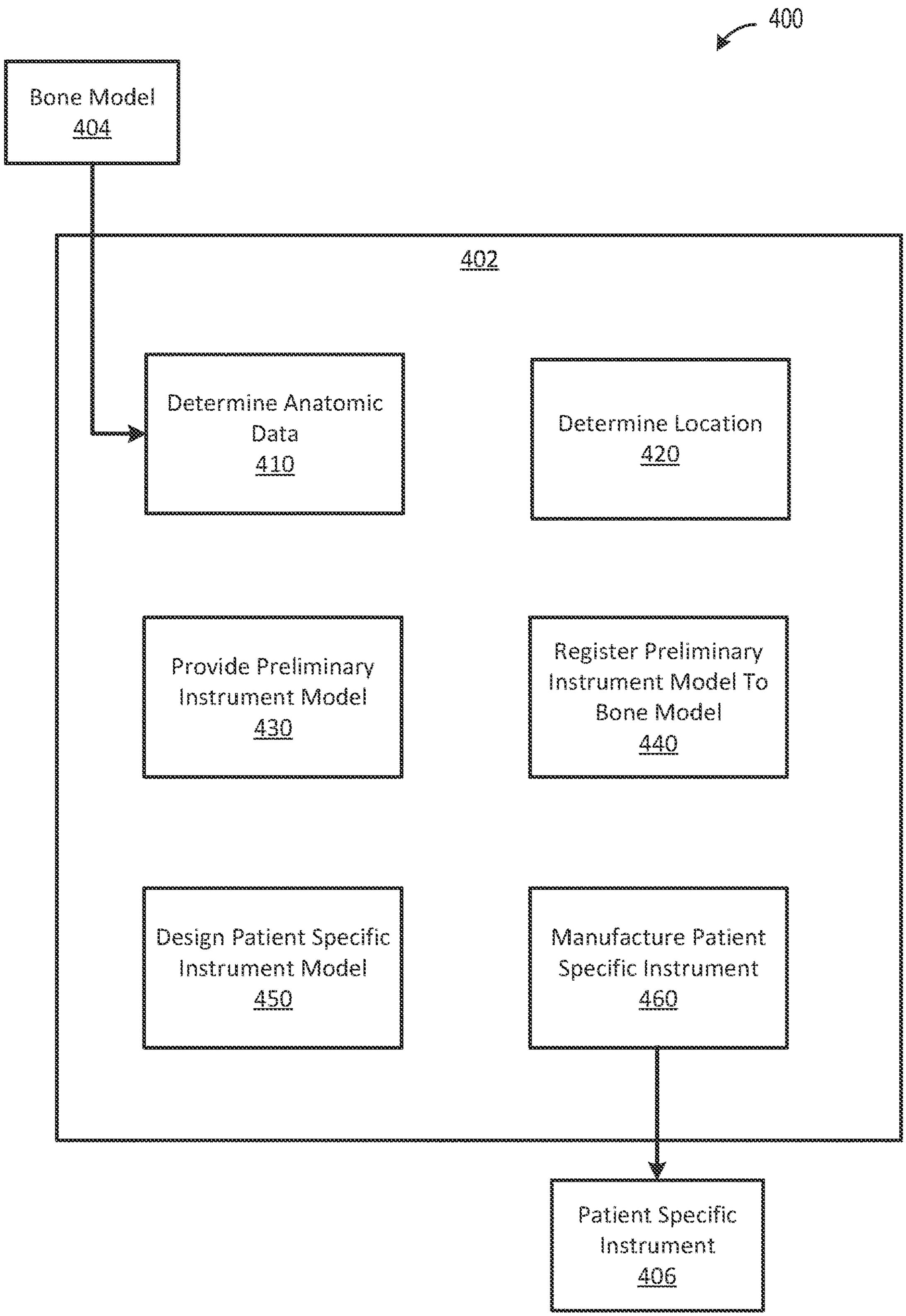
FIG. 4 illustrates an exemplary system configured to generate one or more patient-specific instruments, according to one embodiment.

FIG. 4 illustrates an exemplary system 400 configured to generate one or more patient-specific instruments configured to facilitate surgical procedures, according to one embodiment. The system 400 may include an apparatus 402 configured to accept, review, receive or reference a bone model 404 and provide a patient-specific instrument 406. In one embodiment, the apparatus 402 is a computing device. In another embodiment, the apparatus 402 may be a combination of computing devices and/or software components or a single software component such as a software application.

The apparatus 402 may include a determination module 410, a location module 420, a provision module 430, a registration module 440, a design module 450, and a manufacturing module 460. Each of which may be implemented in one or more of software, hardware, or a combination of hardware and software.

The determination module 410 determines anatomic data 412 from a bone model 404. In certain embodiments, the system 400 may not include a determination module 410 if the anatomic data is available directly from the bone model 404. In certain embodiments, the anatomic data for a bone model 404 may include data that identifies each anatomic structure within the bone model 404 and attributes about the anatomic structure. For example, the anatomic data may include measurements of the length, width, height, and density of each bone in the bone model. Furthermore, the anatomic data may include position information that identifies where each structure, such as a bone is in the bone model 404 relative to other structures, including bones. The anatomic data may be in any suitable format and may be stored separately or together with data that defines the bone model 404.

In one embodiment, the determination module 410 may use advanced computer analysis system such as image segmentation to determine the anatomic data. The determination module 410 may determine anatomic data from one or more sources of medical imaging data, images, files, or the like. Alternatively, or in addition the determination module 410 may use software and/or systems that implement one or more artificial intelligence methods (e.g., machine learning and/or neural networks) for deriving, determining, or extrapolating, anatomic data from medical imaging or the bone model. In one embodiment, the determination module 410 may perform an anatomic mapping of the bone model 404 to determine each unique aspect of the intended osteotomy procedure and/or bone resection and/or bone translation. The anatomic mapping may be used to determine coordinates to be used for an osteotomy procedure, position and manner of resections to be performed either manually or automatically or using robotic surgical assistance, a width for bone cuts, an angle for bone cuts, a predetermined depth for bone cuts, dimensions and configurations for resection instruments such as saw blades, milling bit size and/or speed, saw blade depth markers, and/or instructions for automatic or robotic resection operations.

In one embodiment, the determination module 410 may use advanced computer analysis system such as image segmentation to determine the anatomic data. The determination module 410 may determine anatomic data from one or more sources of medical imaging data, images, files, or the like. The determination module 410 may perform the image segmentation using 3D modeling systems and/or artificial intelligence (AI) segmentation tools. In certain embodiments, the determination module 410 is configured to identify and classify portions of bone based on a condition of the bone, based on the bone condition. Such classifications may include identifying bone stability, bone density, bone structure, bone deformity, bone structure, bone structure integrity, and the like. Accordingly, the determination module 410 may identify portions or sections or one or more bones based on a quality metric for the bone. Advantageously, that determination module 410 can identify high quality bone having a viable structure, integrity, and/or density versus lower quality bone having a nonviable structure, integrity, and/or density and a plurality of bone quality levels in between.

Accordingly, the determination module 410 can guide a surgeon to determine which areas of one or more bones of a patient are within a "soft tissue envelope" (bone of undesirable quality) as that bone relates to a particular deformity or pathology. Identifying the quality of one or more bones of the patient can aid a surgeon in determining what type of correction or adjustment is needed. For example, an ulceration that occurs due to a boney deformity can be mapped using the determination module 410 in a way that a correction can be performed to correct the deformity and reduce pressure to an area and address the structures that were causing the pressure ulceration/skin breakdown.

In addition, the determination module 410 and/or another component of the apparatus 402 can be used to perform anatomic mapping which may include advanced medical imaging, such as the use of CT scan, ultrasound, MRI, X-ray, and bone density scans can be combined to effectively create an anatomic map that determines the structural integrity of the underlying bone.

Identifying the structural integrity of the underlying bone can help in determining where bone resections (e.g., osteotomies) can be performed to preserve the densest bone in relation to conditions such as Charcot neuropathic, arthropathy where lesser dense bone can fail and collapse. It is well documented in the literature that failure to address and remove such lesser dense bone can ultimately lead to failure of a reconstruction and associated hardware.

The present disclosure provides, by way of at least the exemplary system 400, an anatomic map that can be part of anatomic data. The anatomic map can combine structural, deformity, and bone density information and can be utilized to determine the effective density of bone and help to determine where bone should be resected in order to remove the lesser dense bone while maintaining more viable bone to aid in the planning of the osteotomy/bone resection placement.

The location module 420 determines or identifies one or more recommended locations and/or trajectory angles for deployment of an instrument and/or soft tissue based on the anatomic data 412 and/or the bone model 404. In one embodiment, the location module 420 may compare the anatomic data 412 to a general model that is representative of most patient's anatomies and may be free from deformities or anomalies. The location module 420 can operate autonomously and/or may facilitate input and/or revisions from a user. The location module 420 may be completely automated, partially automated, or completely manual. A user may control how automated or manual the determining of the location and/or trajectory angles is.

The provision module 430 is configured to provide a preliminary instrument model 438. The provision module 430 may use a variety of methods to provide the preliminary instrument model. In one embodiment, the provision module 430 may generate a preliminary instrument model. In the same, or an alternative embodiment, the provision module 430 may select a template instrument model for a tendon (or tendon substitute) deployment procedure configured to enable locating the position and/or providing the trajectory provided by the location module 420. In one embodiment, the provision module 430 may select a template instrument model for a minimally invasive surgical (MIS) bunion correction procedure configured to enable locating the position and/or providing the trajectory for the fixation deployment. In one embodiment, the provision module 430 may select a template instrument model from a set of template instrument models (e.g., a library, set, or repository of template instrument models).

The registration module 440 registers the preliminary instrument model with one or more bones or other anatomical structures of the bone model 404. As explained above, registration is a process of combining medical imaging data, patient imaging data, and/or one or more models such that the preliminary instrument model can be used with the bone model 404.

The design module 450 designs a patient-specific instrument (or patient-specific instrument model) based on the preliminary instrument model. The design operation of the design module 450 may be completely automated, partially automated, or completely manual. A user may control how automated or manual the designing of the patient-specific instrument (or patient-specific instrument model) is.

The manufacturing module 460 may manufacture a patient-specific instrument 406 using the preliminary instrument model. The manufacturing module 460 may use a patient-specific instrument model generated from the preliminary instrument model. The manufacturing module 460 may provide the patient-specific instrument model to one or more manufacturing tools and/or fabrication tool (e.g., additive and/or subtractive). The patient-specific instrument model may be sent to the tools in any format such as an STL file or any other CAD modeling or CAM file or method for data exchange. In one embodiment, a user can adjust default parameters for the patient-specific instrument such as types and/or thicknesses of materials, dimensions, and the like before the manufacturing module 460 provides the patient-specific instrument model to a manufacturing tool.

Effective connection of the guide to one or more bones can ensure that surgical steps are performed in desired locations and/or with desired orientations and mitigate undesired surgical outcomes.

Figure 5:
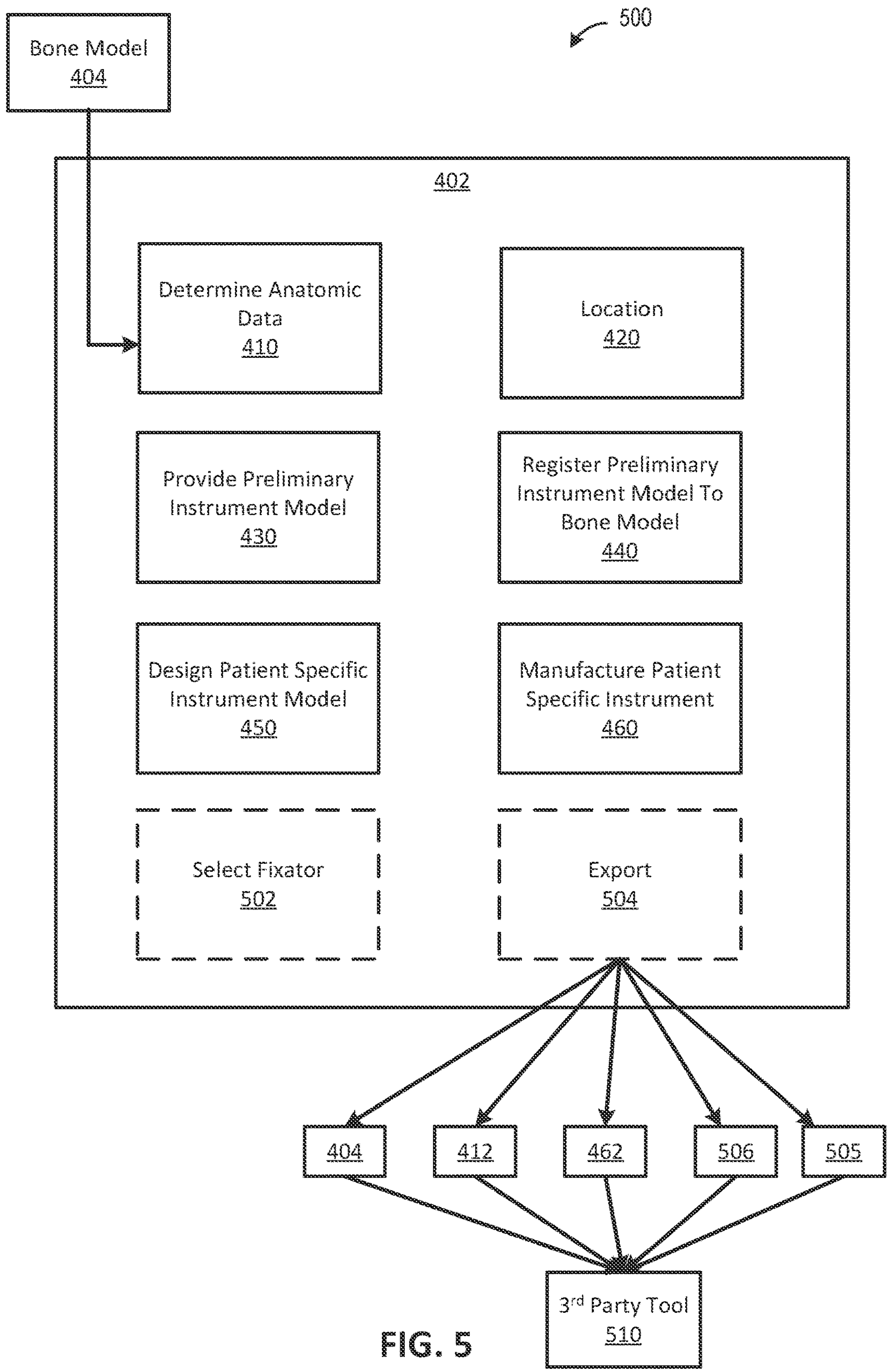
FIG. 5 illustrates an exemplary system configured to generate one or more patient-specific instruments, according to one embodiment.

FIG. 5 illustrates an exemplary system 500 configured to generate one or more patient-specific instruments configured to correct a bone condition, according to one embodiment. The system 500 may include similar components or modules to those described in relation to FIG. 4. In addition, the system 500 may include a fixator selector 502 and/or an export module 504.

The fixator selector 502 enables a user to determine which fixator(s) to use for a MIS bunion correction procedure planned for a patient. In one embodiment, the fixator selector 502 may recommend one or more fixators based on the bone model 404, the location, the trajectory, or input from a user or a history of prior MIS bunion correction procedures performed. The fixator selector 502 may select a fixator model from a set of predefined fixator models or select a physical fixator from a set of fixators. The fixators may include a plate and associated accessories such as screws, anchors, and the like.

In one embodiment, the fixator selector 502 includes an artificial intelligence or machine learning module. The artificial intelligence or machine learning module is configured to implement one or more of a variety of artificial intelligence modules that may be trained for selecting fixator(s) based on anatomic data 412 and/or other input parameters. In one embodiment, the artificial intelligence or machine learning module may be trained using a large data set of anatomic data 412 for suitable fixator(s) identified and labeled in the dataset by professionals for use to treat a particular condition. The artificial intelligence or machine learning module may implement, or use, a neural network configured according to the training such that the artificial intelligence or machine learning module is able to select or recommend suitable fixator(s).

The export module 504 is configured to enable exporting of a patient-specific instrument model 462 for a variety of purposes including, but not limited to, fabrication/manufacture of a patient-specific instrument 406 and/or fixator(s), generation of a preoperative plan, generation of a physical bone model matching the bone model 404, and the like. In one embodiment, the export module 504 is configured to export the bone model 404, anatomic data 412, a patient-specific instrument model 462, a preoperative plan 506, a fixator model 508, or the like. In this manner the custom instrumentation and/or procedural steps for a procedure (e.g., a graft harvesting procedure, minimally invasive surgical (MIS) procedure, or the like) can be used in other tools. The preoperative plan 506 may include a set of step by step instructions or recommendations for a surgeon or other staff in performing a procedure (e.g., a graft harvesting procedure, minimally invasive surgical (MIS) procedure, or the like). The preoperative plan 506 may include images and text instructions and may include identification of instrumentation to be used for different steps of the procedure (e.g., a graft harvesting procedure, minimally invasive surgical (MIS) procedure, or the like). The instrumentation may include the patient-specific instrument 406 and/or one or more fixators/fasteners. In one embodiment, the export module 504 may provide a fixator model which can be used to fabricate a fixator for the procedure.

The exports (404, 412, 462, 506, and 508) may be inputs for a variety of 3rd party tools 510 including a manufacturing tool, a simulation tool, a virtual reality tool, an augmented reality tool, an operative procedure simulation tool, a robotic assistance tool, and the like. A surgeon can then use these tools when performing a procedure or for rehearsals and preparation for the procedure. For example, a physical model of the bones, patient-specific instrument 406, and/or fixators can be fabricated, and these can be used for a rehearsal operative procedure. Alternatively, a surgeon can use the bone model 404, preliminary instrument model 438, and/or a fixator model to perform a simulated procedure using an operative procedure simulation tool.

Referring now to FIGS. 3-5, certain methods, systems, and/or apparatuses are disclosed herein for preparing for, planning, outlining, and/or instrumenting, one or more surgical procedures. Alternatively, or in addition, the methods, systems, and/or apparatuses a disclosed herein can be used for preoperative development and design of systems, instrumentation, and/or implants and/or for preoperative rehearsal and/or instruction of a surgeon before the surgical procedure. For example, a surgeon can use the method 300, bone model(s) 404, patient instrument(s) 406, system 400, and/or apparatus 402 to perform a mock surgical procedure virtually before an actual surgical procedure.

These techniques and/or technologies can greatly advance the medical field and provide valuable instruction and experience to a surgeon prior to an actual surgical procedure. Furthermore, these techniques and/or technologies are made effective owing to the accuracy and precision of the models because of the fidelity of the medical imaging of the patient anatomy. This virtual modeling of patient anatomy has become very accurate and helpful, particularly for hard tissue such as bones and the surfaces of these bones.

Unfortunately, the fidelity and accuracy of these models is not as advanced with respect to the modeling of soft tissue of a patient such as sinews, skin, tendons, ligaments, muscles, fat, and the like. Thus, rehearsal of a surgical procedure, particularly one that includes translating and/or reorienting one or more bone fragments may have limited benefits. In such cases, because the surgeon cannot predict or know beforehand how much movement and reorientation the soft tissue of a patient will permit, the surgeon may need to revise or adapt a surgical procedure intraoperatively to achieve optimal outcomes. The system, apparatus, and methods of the present disclosure enable a surgeon to make intraoperative adjustments to surgical plan based on what the surgeon learns during the surgery.

The present disclosure leverages the use of models, such as computer models, and particularly models of a specific patient to provide and/or generate instrumentation, implants, and/or surgical plans that advanced patient care. Advantageously, these models are unique and customized for a particular patient. Thus, the models reflect the actual anatomical features and aspects of the patient.

However, the utility and helpfulness of the models, methods, systems, and/or apparatuses of FIGS. 3-5, may be dependent on how effectively a surgeon can navigate within, on, or in relation to one or more anatomical references or anatomical features of a patient such that the steps of the surgical procedure can be performed on a patient in the same manner as those modeled using models of the anatomy of the patient. This process of navigation is referred to as a mapping or translation between the virtual or model environment to a physical or real-world environment that includes the patient anatomy and the operating field.

Advantageously, the models, methods, systems, and/or apparatuses of the present disclosure facilitate mapping or translating between a virtual or model environment and/or instrumentation to a physical or real-world environment for a surgical procedure. The present disclosure provides this feature or benefit by providing an apparatus, system, and method, that enables a surgeon to identify, create, form, and/or use reference features for a surgical procedure. The reference feature provides a reference and/or starting point on, in, or associated with anatomy of a patient such that steps, stages, features, or aspects planned and configured within the model can be accurately performed on, with, or to the anatomy of the patient. In certain embodiments, one or more steps of a surgical procedure can be done in connection with or in relation to the reference feature.

The reference feature facilitates moving from one coordinate system or frame of reference in a virtual environment to a position, location, frame of reference, environment, or orientation on, or in, an actual object, structure, device, apparatus, anatomical structure, or the like. Advantageously, the reference feature can coordinate objects, models, or structures in a digital or virtual model or representation with corresponding objects or structures (e.g., anatomical structures) of actual physical objects or structures. Said another way, the reference feature can serve to map from a virtual or modeled object to an actual or physical object.

Advantageously, the embodiment of the present disclosure includes features and aspects that assist a surgeon in locating at least one reference feature, which can then be used in one or more stages of a surgical procedure. In certain embodiments, the actual instruments fabricated using the present disclosure may include one or more references (e.g., a model references). The one or more model instruments may use the one or more references to position and/or orient the one or more model instruments such that other steps of a surgical procedure can be performed in relation to those one or more model instruments and/or model references. Certain model references may key off or related to anatomical references of modeled anatomical body parts. The reference feature(s) correspond to the model references and together enable a surgeon to identify reference features on actual anatomy of a patient for a surgical procedure.

In certain embodiments, one or more fasteners deployed in an instrument such as a resection guide can serve as reference features, for an initial stage of the surgical procedure and/or for subsequent stages of the surgical procedure. In certain embodiments, a bone engagement feature can serve as a reference feature for an osteotomy system and/or surgical procedure.

Advantageously, the embodiments of the present disclosure leverage patient-specific models of patient anatomy and the use of these models to generate patient-specific instruments as well as input from users of the osteotomy (e.g., surgeons). In one embodiment, this input is provided in the form of user directions. Combining patient-specific medical imaging, patient-specific anatomical models, and user directions enable the present disclosure to provide a customized or patient-specific osteotomy that serves the patient's needs as well as aides the surgeon in performing the surgical procedure. In this manner, a surgeon can perform the surgical procedure with higher confidence and assurance that the procedure performed on the patient will coincide with the plan set forth using models in a virtual environment. Consequently, the present disclosure improves the level of patient care and positive outcomes.

Figure 6:
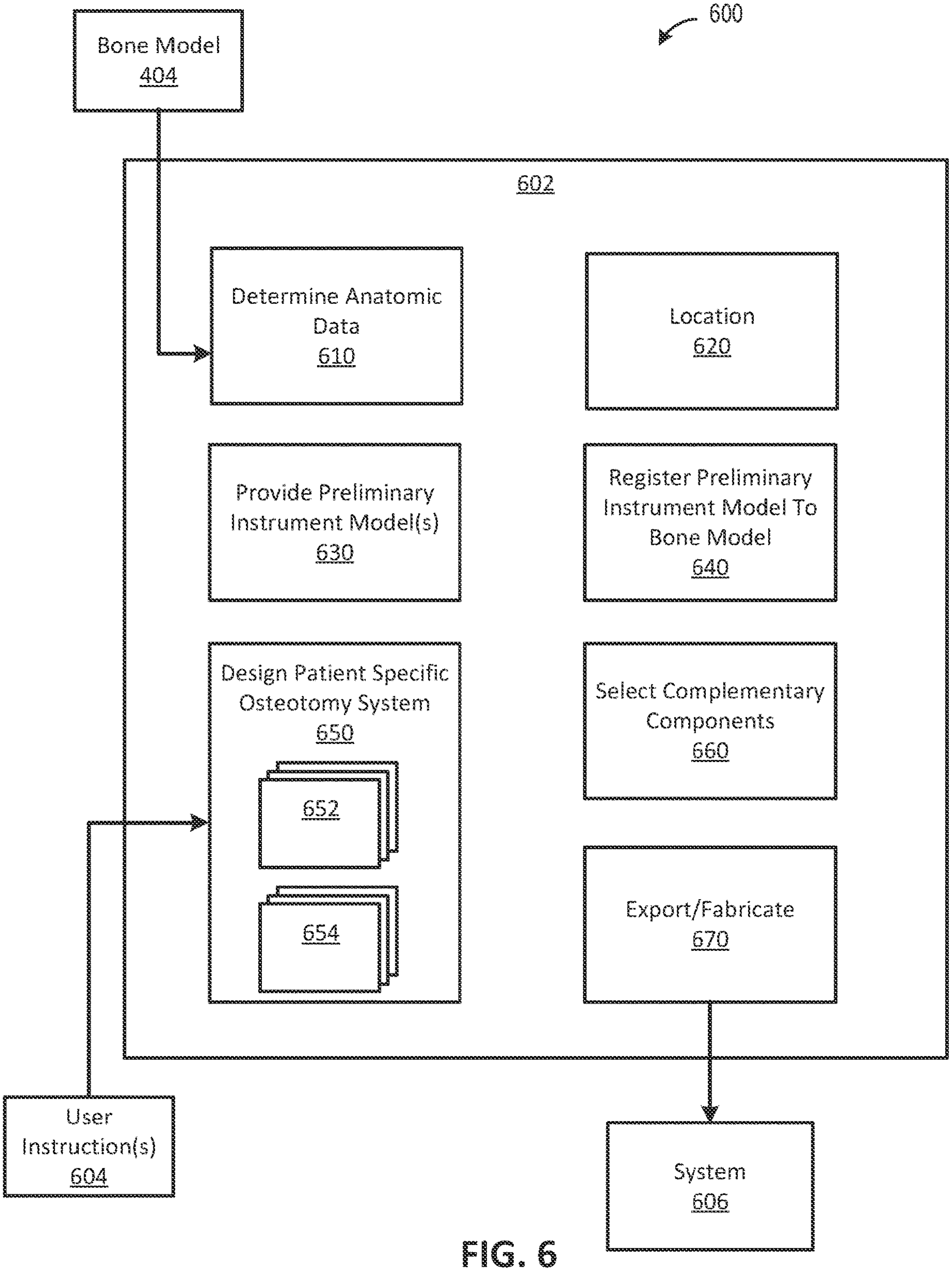
FIG. 6 illustrates an exemplary system configured to generate a patient-specific system, according to one embodiment.

FIG. 6 illustrates an exemplary system 600 configured to design, generate, develop, and/or produce an osteotomy system, according to one embodiment. In certain embodiments, the osteotomy system can be patient-specific. One advantage of the present disclosed embodiments is that an end user of an osteotomy system (e.g., instruments, preoperative plan, implants, etc.) can have as much, or as little control or input, over one or more or all of the aspects of the osteotomy system. Furthermore, this osteotomy system can be customized both to the needs and specific aspects of the patient as well as to the needs and/or preferences and/or desires of the user (e.g., surgeon).

The system 600 may include similar components or modules to those described in relation to FIG. 4. The structures, features, and functions, operations, and configurations of the system 600 may be similar or identical to components or modules of system 400, like parts identified with similar reference numerals. Accordingly, the system 600 may include an apparatus 602 configured to accept, review, receive or reference a bone model 404 and user instructions 604 and provide a patient-specific system 606. In one embodiment, the apparatus 602 is a computing device. In another embodiment, the apparatus 602 may be a combination of computing devices, systems, apparatuses, software components, single software component such as a software application, one or more third party manufacturers, or the like.

The apparatus 602 may include a determination module 610, a location module 620, a provision module 630, an optional registration module 640, a design module 650, a selection module 660, and an export/fabrication module 670. Each of which may be implemented in one or more of, software, hardware, or a combination of hardware and software. In certain embodiments, one or more parts of the system 600 may be operated by a user (e.g., a technician), a plurality of users, and may include input, involvement, and/or feedback from an end user of the osteotomy system developed. Generally, the end user of the osteotomy system will be a surgeon. Those of skill in the art will appreciate that depending on the surgical procedure being performed, one or more of the modules of the apparatus 602 may or may not be used.

The determination module 610 may operate in a similar manner to the determination module 410. The location module 620 may operate in a similar manner to the location module 420. The provision module 630 may operate in a similar manner to the provision module 430. The registration module 640 may operate in a similar manner to the registration module 440.

The design module 650 enables one or more users to design a system 606 and in particular a patient-specific system 606. A patient-specific system 606 can include a number of different instruments, components, and/or systems, including but not limited to one or more cutting tools, one or more resection guides, one or more provisional fasteners, one or more fixation systems and/or instruments, a preoperative plan, one or more kits of implants and/or trial components, one or more alignment guides, one or more positioning guides, one or more reduction guides, one or more, one or more navigation guides, one or more fixation guides, one or more, one or more compression guides, one or more rotation guides, and the like. In addition, one or more of these components can be patient-specific. For example, the patient-specific system 606 can include a patient-specific instrument, patient-specific trajectory guide, a patient-specific resection guide, a patient-specific cutting guide, a patient-specific positioning guide or positioner, another patient-specific instrument, or the like.

Alternatively, or in addition, the patient-specific system 606 can include one or more subparts or components of each of the instruments, components and/or systems of the patient-specific system 606. For example, in one embodiment, the design module 650 may enable a user and/or end user to determine and/or define a number, size, shape, position, orientation, trajectory and/or configuration for one or more bone attachment features, a number, size, shape, position, orientation, trajectory and/or configuration for one or more resection features, a number, size, shape, position, orientation, trajectory and/or configuration for one or more bone engagement features, a number, size, shape, position, orientation, trajectory and/or configuration for one or more bone engagement surfaces, a number, size, shape, position, orientation, trajectory and/or configuration for one or more fixators (either or both provisional or permanent), and the like.

Those of skill in the art will appreciate that the design module 650 offers a large variety of different options and combinations for the constituents of the patient-specific system 606 as well as a plurality of options for the components of the patient-specific system 606 and that such options may be overwhelming. Advantageously, the surgical procedure to be performed, the bone model 404, and user instructions 604 each alone and/or in combination define an initial set of members for the patient-specific system 606. For example, certain well known surgical techniques have specific names and surgeons understand and/or have experience doing these procedures and therefore know what instruments will be needed for the surgical procedure.

In addition, each surgeon is different just as each patient is different. Therefore, surgeon experience and/or preferences may factor into the members of the patient-specific system 606 a particular surgeon wants and/or the configuration of the members of the patient-specific system 606. For example, where one surgeon may prefer to use two resection guides another surgeon may want to use one resection guide and perform other osteotomies for the surgical procedure manually or free-hand.

Based on the surgical procedure to be performed, many decisions about the design and/or make up of the patient-specific system 606 can be made as recommendations and/or proposals by a technician to a surgeon. These decisions can be based in whole or in part on the surgical procedure to be performed, the bone model 404 and/or the user instructions 604.

For example, suppose a surgeon would like a patient-specific system 606 for an osteotomy procedure. One goal of the procedure may be to relieve pain of the patient and to remove a minimal amount of bone in the process of completing the procedure. In such an example, the bone model 404 may be of one or more bones of a foot and/or ankle of the patient. The surgeon may provide a request and/or a set of user instructions 604 for a patient-specific system 606 for this osteotomy procedure.

Those of skill in the art will appreciate that the user instructions 604 may be of a variety of different types, lengths, number of details and may be provided in a variety of different formats including oral, written, or the like. In one embodiment, the user instructions 604 may be a request for a patient-specific system 606 that includes a set of default instruments, preoperative plan, implants, or the like. For example, the user instructions 604 may as short and simple as "Please provide an osteotomy system for a bone of the left foot for patient <<identifying information (e.g., name, dob, etc.)>> with medial approach." The user instructions 604 may be provided in the form of a product order, a purchase order, a prescription, or the like. The user instructions 604 may be provided in written manual/analog form, include a manual signature, digital form, include an e-signature, or the like. In addition, the user instructions 604 may include security and/or authorization features that enable the receiver to confirm that the user instructions 604 are valid and are authorized by a particular surgeon or doctor. The user instructions 604 may indicate the approach to the surgical site (e.g., an ankle or foot joint or bone) the surgeon wants to take, anterior, posterior, medial, lateral, or the like.

In another embodiment, the user instructions 604 may include specific instructions for the number and/or kind or type of components in the patient-specific system 606 and/or the configuration of one or more of these components. For example, the user instructions 604 may identify a specific fixation product or fixation system the surgeon will be using for permanent fixation of the osteotom(ies). Alternatively, or in addition, the user instructions 604 may include designation of one or more complementary components and/or configurations for these components to be included in the patient-specific system 606.

In one embodiment, the user instructions 604 may designate a particular material and/or mass for fabricating one or more guides to be included in the patient-specific system 606. Some surgeons may find that patient-specific instruments, such as a patient-specific resection guide may more readily register to one or more bone surfaces if the instrument has a greater mass and/or weight. With the greater mass and a sufficient fidelity bone engagement surface, a patient-specific instrument may seem to find its own way or seek out a desired position on a bone that matches or substantially matches a position planned when the patient-specific system 606 was developed. Consequently, a surgeon may request in the user instructions 604 that the instrument be made from a metal such as titanium.

With the bone model 404 and user instructions 604 a user such as a technician may operate the design module 650 alone or together with other modules of the apparatus 602 to develop a patient-specific system 606. In certain embodiments, a single user operates the apparatus 602. Alternatively, or in addition, a plurality of users, which may include an end user, such as surgeon can operate or interact with one or more modules of the apparatus 602 as the patient-specific system 606 is designed or developed.

In one embodiment, a technician may provide a patient-specific system 606 that includes one or more complementary components and one or more resection guides, which may be patient-specific. The technician may also provide a preoperative plan. These may be provided to an end user (e.g., surgeon) either directly or by accessing the apparatus 602 remotely. The end user may review the preoperative plan and/or the components of the patient-specific system 606 (e.g., resection guides) and may approve of the patient-specific specific system 606 or may request changes. In certain embodiments, these changes may include the addition of one or more added bone engagement features, one or more resection guides, a change in a trajectory for a bone attachment feature, a change in trajectory for an osteotomy, an addition of openings in a guide to coincide with openings needed for a fixation system, as well as a plurality of other possible changes to the patient-specific system 606. The technician may then make the requested changes and present a revised patient-specific system 606 for the surgeon to review again. Next, the surgeon may approve of the revised patient-specific system 606 and/or request additional changes.

In the illustrated embodiment, the design module 650 may include a plurality of resection features 652 and/or a plurality of bone engagement features 654. A technician may select one or more resection features 652 and/or one or more bone engagement features 654 and include them in the patient-specific system 606. Alternatively, or in addition, a surgeon may designate which resection features 652 and/or bone engagement features 654 to include in the patient-specific system 606.

In certain embodiments, the surgeon and technician may collaborate and/or consult with each other regarding the design and/or configuration of the patient-specific system 606 and its components. The technician may share with the surgeon information about the technological features and/or limitations of the components of the patient-specific system 606 and use the technician's experience and know-how to make recommendations to the surgeon. The surgeon can present ideas and/or requests regarding what the surgeon would like for components of the patient-specific system 606 and the technician can determine whether those ideas/requests can be satisfied using a patient-specific system 606.

The apparatus 602 uses both the bone model 404 and user instructions 604 to provide a patient-specific system 606. Advantageously, the apparatus 602 enables a surgeon to be involved in the design and development of a patient-specific system 606 that is suited not just for the patient, but also for the needs, skills and/or preferences of the surgeon. In this manner, a patient-specific system 606 can be provided that improves patient care and accomplishing desired outcomes.

In one embodiment, the operation of the design module 650 may be completely automated, partially automated, or completely manual. A user may control how automated or manual the designing of the patient-specific system 606 is, including any patient-specific instrument models, patient-specific instruments, and/or other components of the patient-specific system 606.

The apparatus 602 may include a selection module 660 and an export/fabrication module 670. The selection module 660 facilitates the selection and/or customization of one or more complementary components for a patient-specific system 606. Complementary components are described herein, but can include certain guides or other aids to facilitate completing a surgical procedure as planned. In one embodiment, the operation of the selection module 660 may be completely automated, partially automated, or completely manual. A user may control how automated or manual the selection module 660 is.

The export/fabrication module 670 is configured to enable exporting of a patient-specific system 606 for a variety of purposes including, but not limited to, fabrication/manufacture of one or more patient-specific instruments and/or fixator(s), ordering or fabricating one or more members of the patient-specific system 606, generation of a preoperative plan, generation of a physical bone model matching the bone model 404, and the like.

In one embodiment, the export/fabrication module 670 is configured to export the bone model 404, anatomic data 412, one or more patient-specific instrument models 462, a preoperative plan 506, a fixator model 508, or the like. In this manner the custom instrumentation and/or procedural steps for a procedure can be used in other tools. The preoperative plan 506 may include a set of step-by-step instructions or recommendations for a surgeon or other staff in performing a procedure (e.g., a graft harvesting procedure, minimally invasive surgical (MIS) procedure, or the like). The preoperative plan 506 may include images and text instructions and may include identification of instrumentation to be used for different steps of the procedure (e.g., a graft harvesting procedure, minimally invasive surgical (MIS) procedure, or the like). The instrumentation may include a patient-specific instrument, bone engagement features, and/or one or more fixators/fasteners.

Figure 7:
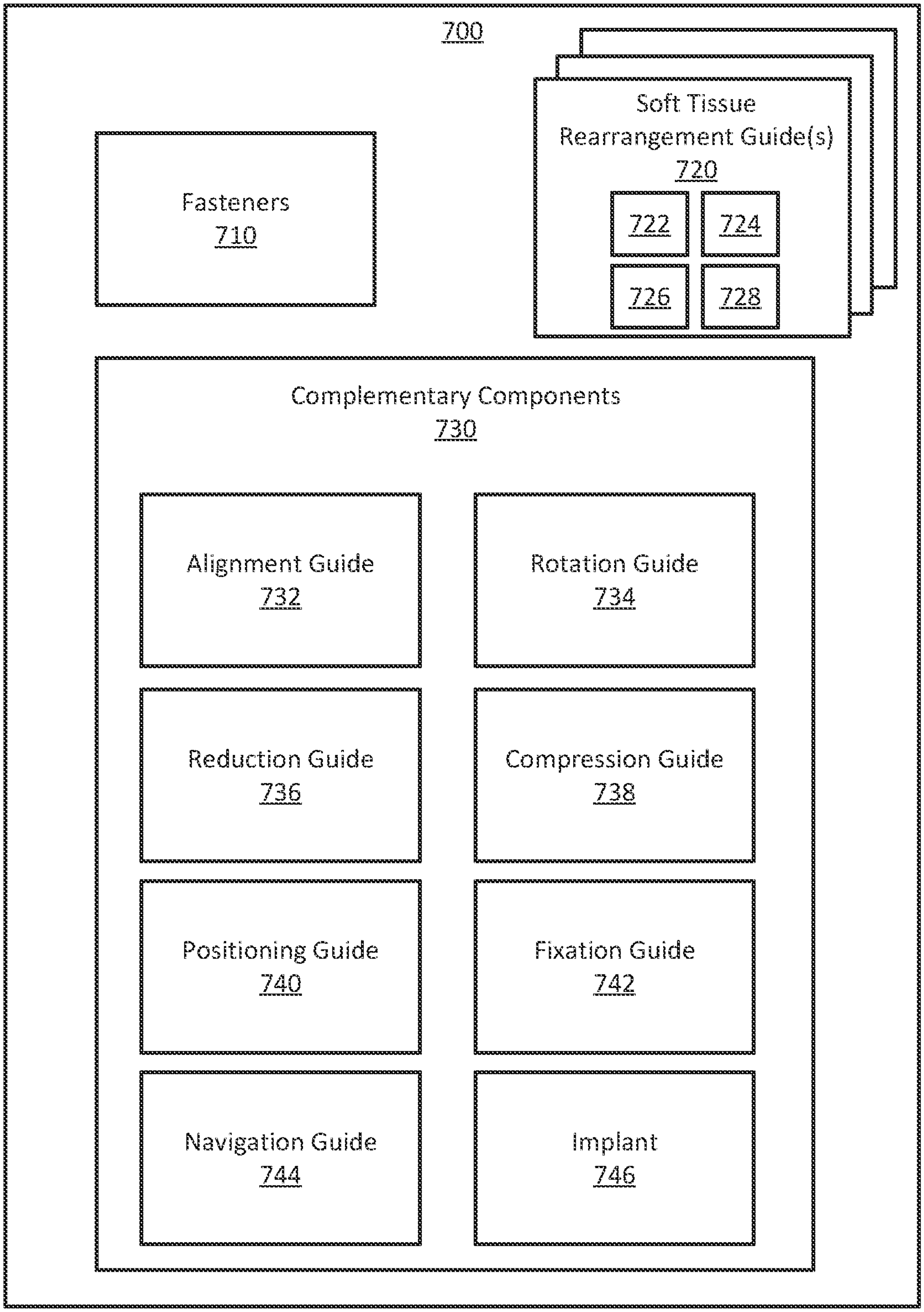
FIG. 7 illustrates an exemplary system for remediating a condition present in a patient's foot, according to one embodiment.

FIG. 7 illustrates an exemplary system 700 for remediating a condition present in a patient's foot, according to one embodiment. The system 700 can include one or more fasteners 710, one or more soft tissue rearrangement guides (STRGs) 720, and one or more complementary components 730. While a system 700 can be used for a variety of procedures, one or more features, components, and/or aspects of the system 700 may be particularly suited for one or more osteotomies on one or more bones of a structure such as a patient's foot, ankle, wrist, hand, shoulder, or the like.

In certain embodiments, the one or more fasteners 710 can include one or more permanent fasteners and/or one or more temporary fasteners. Typically, the fasteners 710 may be used during a variety of different steps of a procedure. Temporary fasteners are often used because they can securely hold bone or parts/fragments of bones while steps of the procedure are conducted. A common temporary fastener that can be used with system 700 is a K-wire, also referred to as a pin, guide pin, and/or anchor pin. Permanent fasteners 710 such as bone screws, bone staples, sutures, tethers or the like may also be used in a surgical procedure.

The one or more STRGs 720 assist a surgeon in performing different steps for a soft tissue rearrangement procedure or other procedure. The one or more STRGs 720 assist a surgeon in positioning and aligning instrumentation and/or bone tunnels for a soft tissue rearrangement procedure. Those of skill in the art will appreciate that a STRG 720 may be referred to by different names in different embodiments and/or contexts. For example, a STRG 720 may also be referred to as a tendon transfer system, a tendon trajectory guide, bone tunnel guide, a tendon transfer anchor guide, a patient-specific tendon transfer anchor guide, or the like.

In certain embodiments, a STRG 720 includes one or more trajectory ports 722, one or more landmark registration features 724 and a bone engagement feature 726. The trajectory port 722 can take a variety of forms and/or embodiments. Similarly, the landmark registration feature 724 can take a variety of forms and/or embodiments. The bone engagement feature 726 is a feature of the STRG 720 that contacts and/or engages with one or more bones of a patient. In certain embodiments, the STRG 720 can include one or more optional bone attachment features 728.

The trajectory port 722 guides placement of a temporary fastener and/or forming an opening or tunnel in the bone of a patient. The landmark registration feature 724 can serve to ensure the STRG 720 is placed in a desired location on one or more bones. The bone engagement feature 726 can also serve to ensure the STRG 720 is placed in a desired location on one or more bones. In certain embodiments, the bone attachment feature 728 can include a hole in the STRG 720 that operates together with a temporary fastener such as a K-wire or pin to secure the STRG 720 to bone.

In certain embodiments, a STRG 720 may include one or more bone engagement features 726 and/or one or more landmark registration features 724. In certain embodiments, a landmark registration feature 724 may extend from one or more sides or ends of a STRG 720 and engage with one or more landmarks of a bone or joint or anatomical structure of a patient. Registration of the landmark registration feature 724 to a landmark of a bone or joint can serve to confirm and/or ensure that a surgeon has located a desired placement and/or orientation for a STRG 720.

In certain embodiments, the bone engagement features 726 are patient-specific: designed and/or contoured to match anatomy such as a surface of: one or more bones and/or bone surfaces the STRG 720 contacts during the procedure or one or more joints proximal to the STRG 720 during the procedure. Alternatively, or in addition, the bone engagement feature 726 may not be patient-specific, and may, or may not, contact a bone surface during use of the STRG 720. In one embodiment, a skin contact surface may be used in addition to, or in place of, a bone engagement surface. Those of skill in the art appreciate that one or more sides of any of the members of the system 700 may include one or more bone engagement features 726. Consequently, one or more sides of the fasteners 710, the resection guide(s) 720, the complementary components 730, navigation guides 792, and/or the implants 794 may include one or more bone engagement features 726.

In certain embodiments, the STRGs 720 and/or aspects of the STRGs 720 may be integrated into other components and/or instruments, such as a pin guide, a trajectory guide, an alignment guide, or the like.

The complementary components 730 serve to assist a surgeon during one or more steps of a procedure. Those of skill in the art appreciate that a number of components can serve as complementary components 730. One or more of the features, functions, or aspects of the complementary components 730 can include patient-specific features. Examples of complementary components 730 include, but are not limited to, an alignment guide 740, a rotation guide 750, a reduction guide 760, a compression guide 770, a positioning guide 780, a fixation guide 790, navigation guides 792, and/or one or more implants 794. In general, the complementary components 730 serve to assist a surgeon in performing the function included in the name of the complementary component 730. Thus, an alignment guide 740 can help a surgeon align bones, parts of bones, or other parts of a patient as part of a procedure. A rotation guide 750 can help a surgeon rotate one or more bones, parts of bones, or other parts of a patient as part of a procedure. In one embodiment, a rotation guide 750 may hold one bone fragment stable while another bone fragment is rotated into a desired position.

A reduction guide 760 can help a surgeon position and/or orient one or more bones, parts of bones, or other parts of a patient as part of a procedure in order to reduce the bone, bones, bone parts, or other parts and/or in order to position and/or orient the bone, bones, bone parts, or other parts to a desired position and/or orientation. In certain embodiments, aspects and/or features of a reduction guide 760 can be integrated into one or more other components of a system 700, such as components of the complementary components 730. A compression guide 770 can help a surgeon compress one or more bones, parts of bones, or other parts of a patient together or against an implant as part of a procedure. In certain embodiments, compression guide 770 can be a separate instrument such as a compressor and/or a combined compressor/distractor. The compressor/distractor can be used to compress two or more cut faces formed by an osteotomy until fixation is deployed or distract bones or parts of bones involved in a procedure. In certain embodiments, a compression guide 770 may serve a dual purpose as both a compression guide 770 and as a positioning guide 780. The same instrument may be used to both translate and/or rotate bones or bone fragments and compress two or more cut faces formed by an osteotomy until fixation can be deployed.

A positioning guide 780 (also referred to as a positioner) can help a surgeon position one or more bones, parts of bones, or other parts of a patient as part of a procedure. For example, a positioning guide 780 may hold one bone or bone fragment stable and hold one or more other bone fragments in a desired position while permanent or temporary fixation is deployed. In certain embodiments, the positioning guide 780 may hold bone fragments in a reduced position, and thus may function as both a positioning guide 780 and/or a reduction guide 760.

In certain embodiments, the positioning guide 780 may be designed and fabricated to be patient-specific. The patient-specific aspects can include a patient-specific bone engagement surface, a predefined angle for reorienting one or more bone or bone parts within one or more planes, a predefined position for bone attachment features 724 or fasteners 710, a predefined or patient-specific offset or amount of translation that is provided, or the like. Alternatively, or in addition, the positioning guide 780 may be selected from a kit, collection, or repository of a number of positioning guides 780: each having a different configuration for one or more aspects/attributes of the positioning guide 780. For example, each member of the repository/kit may include a different positioning angle (repositioning or correction angle), the angles may differ by 2 degrees for example. In such an embodiment, each positioning guide 780 may not be patient-specific to a particular patient but may provide the desired amount of positioning to meet the goals of the surgeon. In certain embodiments, a preoperative plan generated based on the present disclosure may include a recommendation for the positioning guide 780 to be used, even if the recommended positioning guide 780 is not patient-specific to the particular patient.

A fixation guide 790 can help a surgeon in completing one or more temporary or permanent fixation steps for one or more bones, parts of bones, or other parts of a patient as part of a procedure. The fixation guide 790 may include and/or may use one or more components of a fastener or fixation system including implant hardware of the fastener or fixation system.

Those of skill in the art will appreciate that the other complementary components 730 may each have functions, purposes, and/or advantages with respect to one or more anatomical parts of the patient. Alternatively, or in addition, the other complementary components 730 may each have functions, purposes, and/or advantages with respect to one or more instruments and/or one or more anatomical parts of the patient. For example, a trajectory guide may be a type of alignment guide 740 in that the trajectory guide facilitates alignment of fixation with the desired location and/or trajectory/orientation with respect to one or more anatomical parts of the patient. Alternatively, or in addition, a trajectory guide may also be considered a type of fixation guide 790 because the trajectory guide facilitates deployment of one or more fasteners 710.

Advantageously, the system 700 can help a surgeon overcome one or more of the challenges in performing an osteotomy procedure, particularly on bones of a hand or of a foot of a patient, such as on the forefoot, midfoot, or hindfoot. One challenge during an osteotomy procedure can be maintaining control of, and/or position, and/or orientation of a bone, one or more bones, and/or bone pieces/fragments, particularly once a resection or dissection is performed. Advantageously, the fasteners 710, resection guide(s) 720, and/or complementary components 730 can be configured to assist in overcoming this challenge.

Advantageously, system 700 can help a surgeon in positioning, placing, and/or orienting a resection guide accurately. Modern techniques may include preoperative planning, simulation, or even practice using computer models, 3D printed models, virtual reality systems, augmented reality systems or the like. However, simulations and models are still different from actually positioning a resection guide on a patient's bone, joint, or body part during the procedure. System 700 can include a number of features, including patient-specific features, to assist the surgeon with the positioning. In one embodiment, the STRG 720 can include one or more landmark registration features 724.

Advantageously, the system 700 can help a surgeon in securing guides of the system 700, such as a resection guide, as well as how to readily remove the guide (e.g., resection guide) without disturbing a reduction, shifting, reorienting, or repositioning one or more bones or parts of bones while removing the guide. In certain embodiments, the system 700 is configured to permit removal of a guide while keeping temporary fasteners in place for use in subsequent steps of an osteotomy procedure. Alternatively, or in addition, system 700 may facilitate positioning of temporary fasteners during one step of a wedge osteotomy procedure for use in a subsequent step of the wedge osteotomy procedure. Removal of a guide during an osteotomy procedure can be particularly challenging where translation and/or rotation of the bones involved in the osteotomy procedure is required for the success of the osteotomy procedure. Advantageously, system 700 accommodates translation and/or rotation of the bones during the osteotomy procedure while facilitating a successful outcome for the osteotomy procedure.

Advantageously, the components of the system 700 can be specifically designed for a particular patient. Alternatively, or in addition, the components of the system 700 can be specifically designed for a class of patients. Each of the components of system 700 can be designed, adapted, engineered and/or manufactured such that each feature, attribute, or aspect of the component is specifically designed to address one or more specific indications present in a patient. Advantageously, the cuts made for the osteotomy procedure can be of a size, position, orientation, and/or angle that provides for an optimal osteotomy with minimal risk of undesirable resection. In one embodiment, the components of system 700 can be configured such that an osteotomy is performed that enables a correction in more than one plane in relation to the parts of the body of the patient. For example, cut channels or resection features 722 in a STRG 720 can be oriented and configured such that when the bones are fused/fixated the correction results from translation, rotation, and/or movement of bones or bone parts in two or more planes (e.g., sagittal and transverse) once the fragments or bones are reduced.

In certain embodiments, the exemplary system 700 may include a plurality of fasteners 710, STRGs 720, and/or complementary components 730. For example, a surgeon may plan to resect a plurality of osteotomies from the bone(s) in order to accomplish a desired correction. In one example, one or more wedge segments may be resected from a medial side of a patient's foot and another one or more wedge segments may be resected from a lateral side of the patient's foot. These wedge segments may extend part way into the foot, or through from one side of the foot to the other. Of course, multiple wedge segments may be formed on one side of the foot as well.

Additionally, a surgeon may use one or more components in an exemplary system 700 to make multiple cuts, openings, and/or bone tunnels in the bone(s). The multiple cuts may be centered over or around an apex of a deformity or positioned at other locations within the foot such that when the multiple cuts are made, any resected segments removed, bone tunnels formed, or added bone void fillers introduced, and/or bones and/or bone fragments translated and/or rotated the combined angles, surfaces, removed segments, and/or added portions cooperate to provide a desired correction. Each of the components of the exemplary system 700 can be identified, defined, and reviewed using the apparatuses, systems, and/or methods of the present disclosure.

In certain embodiments, the components of system 700 may be made as small as possible to minimize the amount of soft tissue that is opened in the patient for the procedure. Alternatively, or in addition, walls and/or sides of the components may be beveled and/or angled to avoid contact with other hard tissue or soft tissues in the operating field for the procedure.

Those of skill in the art will appreciate that for certain procedures a complementary component 730 may not be needed or a given complementary component 730 may be optional for use in the procedure. Similarly, those of skill in the art will appreciate that certain features of the fasteners 710, STRGs 720, and/or complementary components 730 can be combined into one or more of apparatus or devices or may be provided using a plurality of separate devices.

Figure 8:
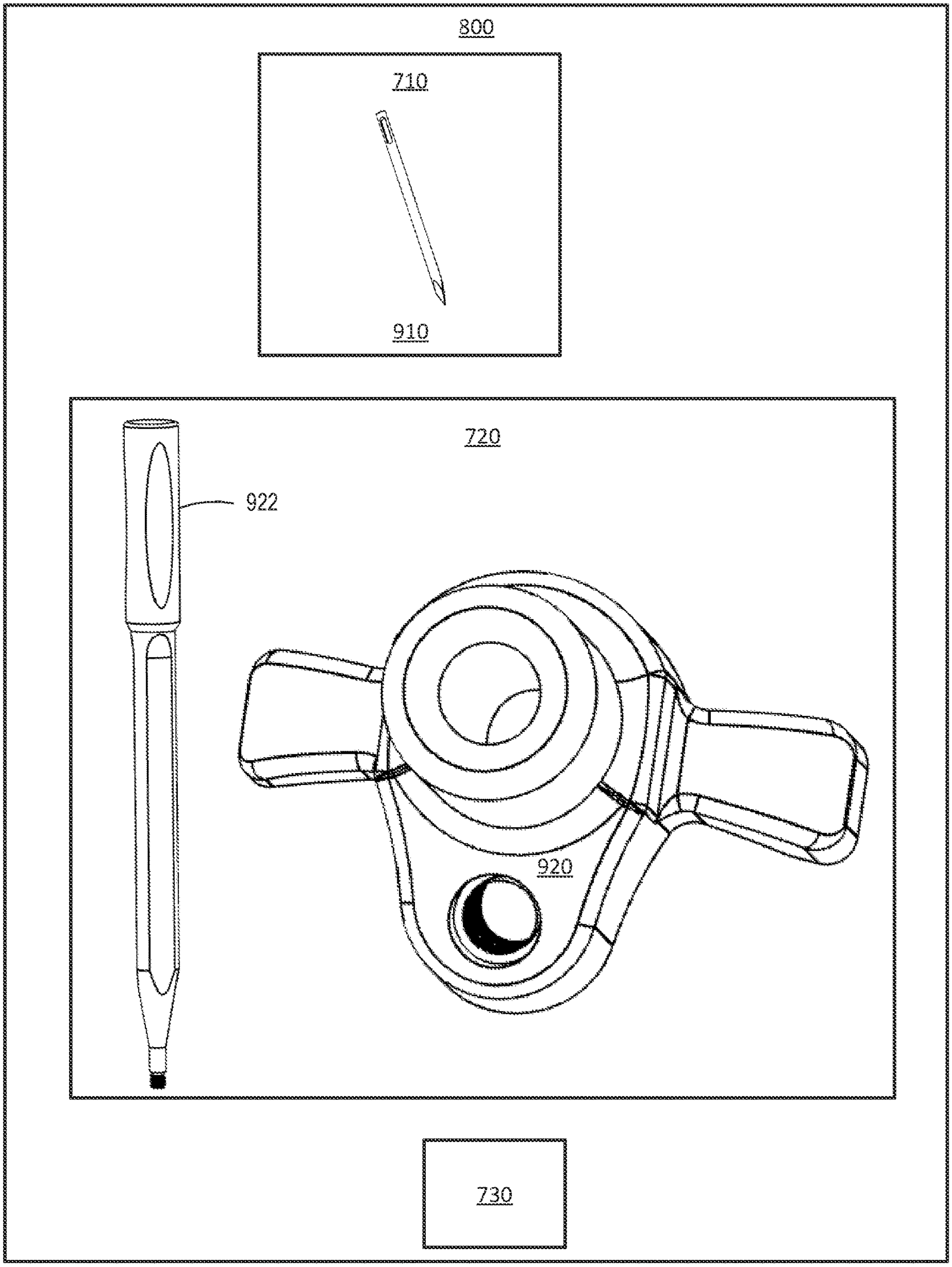
FIG. 8 illustrates an exemplary soft tissue rearrangement system, according to one embodiment.

FIG. 8 illustrates an exemplary soft tissue rearrangement system 800, according to one embodiment. The soft tissue rearrangement system 800 can include one or more fasteners

710 embodied in for the form of depicted exemplary fastener 910, one or more STRGs 720 embodied in for the form of depicted exemplary bone tunnel guide 920, and zero or one or more complementary components 730. The bone tunnel guide 920 may also include one or more trajectory ports 722, one or more optional landmark registration features 724, and/or one or more optional bone engagement features 726. (See FIG. 7) In certain embodiments, a bone engagement feature 928 can include one or more bone engagement surfaces.

While specific embodiments of complementary components 730 are not specifically shown here in relation to the system 800, those of skill in the art will appreciate that complementary components 730 can be similar in feature, design, implementation, configuration, and purpose as those described in relation to the system 700 and can be used for the soft tissue rearrangement system 800. Thus, the soft tissue rearrangement system 800 can include one or more alignment guides 732, rotation guides 734, reduction guides 736, compression guides 738, positioning guides 740, fixation guides 742, navigation guides 744, implants 746, or the like.

The bone tunnel guide 920 may be a custom patient-specific soft tissue rearrangement guide made for a particular patient and/or for a particular surgical procedure. Various aspects of the bone tunnel guide 920 may be patient-specific, including, but not limited to, an angle and/or orientation for a trajectory port 924 of the bone tunnel guide 920, a position of the trajectory port 924, a depth of the trajectory port 924, a size and/or geometric configuration of the trajectory port 924, a size of the bone tunnel guide 920, a configuration, design, and/or composition of a bone contacting structure such as a bone engagement feature 928 of the bone tunnel guide 920, a number of bone engagement features 928, a position of the bone tunnel guide 920 relative to one or more bones of a patient, a position, orientation, configuration and/or existence of an optional handle 922, and the like.

In one embodiment, the bone tunnel guide 920 includes a body 932 that includes a superior side 934, an inferior side 936, a medial side 938, a lateral side 940, a posterior side 942, and an anterior side 944. Generally, the sides of the bone tunnel guide 920 refer to the direction the sides face when the bone tunnel guide 920 is in use.

In certain embodiments, a position, configuration, and/or orientation of the trajectory port 924 can be determined and/or defined at least partially based on a bone model of at least a portion of a bone of a patient's foot. The trajectory port 924 extends through the body 932. In one embodiment, the trajectory port 924 may be positioned to guide a tool for forming a bone tunnel in a bone of a patient for a surgical procedure such as a deformity correction. The bone model may be defined and/or determined based at least in part on medical imaging of the bone of the patient.

In one embodiment, the position and/or configuration of the trajectory port 924 may be determined, defined, and/or dictated at least in part by both a bone model of a portion of a patient's foot and user instructions 604. Advantageously, the user instructions 604 may identify certain goals for the bone tunnel guide 920 such as minimal size (i.e., width, length, depth), shape, contour, position, orientation, trajectory, and the like. Since the bone tunnel guide 920 guides the formation of bone tunnel, the configuration of the bone tunnel guide 920 provided by the user instructions 604 can also define an osteotomy or bone tunnel created using the bone tunnel guide 920.

In certain embodiments, a user, or end user, may review the bone model, and a model of the bone tunnel guide 920 and based on these models determine, at least in part, where to position and/or orient a trajectory port 924 within a bone tunnel guide 920. Advantageously, determining a position and/or orientation for the trajectory port 924 in a model of an instrument can be directly reflected in a fabricated instrument based on the model. In one embodiment, the position and/or orientation for the trajectory port 924 can be based on user instructions 604. Alternatively, or in addition, other features of a trajectory port 924 can be based, at least partially, on user instructions 604. Alternatively, or in addition, in one embodiment, features of a bone tunnel guide 920 can be based on accepted practice aspects for a particular surgical procedure.

FIGS. 9A-9I illustrate views of a bone tunnel guide 920 of the system of FIG. 8, according to one embodiment. The bone tunnel guide 920 includes at least one trajectory port 924. In the illustrated embodiment, the bone tunnel guide 920 includes a bone engagement feature 928. Other embodiments may not include a bone engagement feature 928. In certain embodiments, one or more of the bone engagement features 928 may include a bone engagement surface 946. Alternatively, or in addition, the bone tunnel guide 920 may include a bone engagement surface 946. Alternatively, or in addition, the bone tunnel guide 920 may also include one or more bone attachment features 930 (not shown), and a handle coupler 950.

The trajectory port 924 extends from the body 932. In one embodiment, the trajectory port 924 includes an opening 948 that extends from a top surface of the trajectory port 924 through to the bottom surface. The trajectory port 924 serves to guide a surgeon and indicates a desired trajectory for a temporary fastener, a cutting tool, or other instrumentation a surgeon may use for deploying a tendon, tendon substitute, tendon anchor, soft tissue, a graft, or the like.

For example, in a tendon transfer, a surgeon may insert a temporary fastener such as a K-wire into the opening 948 and deploy the K-wire into bone that contacts the inferior surface (inferior side 936) of the bone tunnel guide 920. Alternatively, or in addition, a surgeon may deploy fastener 910 into the opening 948 and into bone contacting an inferior surface of the bone tunnel guide 920. In certain embodiments, the opening 948 has a circular cross-section and has a diameter sized to accept the fastener 910 or a cutting tool that a surgeon wants to use for the procedure.

Advantageously, the trajectory port 924 and/or opening 948 may extend from the body 932 at any angle needed to provide a desired trajectory angle. In one embodiment, the opening 948 extends perpendicular to the body 932. In another embodiment, the opening 948 extends at an angle between about 5 degrees and about 85 degrees relative to the body 932.

In one embodiment, the length of the opening 948 is sufficient to assist a surgeon in maintaining a trajectory along a longitudinal axis of the opening 948 through the bone tunnel guide 920 and into a bone of a patient. Alternatively, or in addition, the length of the opening 948 may extend away from the body 932 such that the trajectory port include a port body that extends away from the body 932. The port body may have a length that enables a user to grasp the port body to secure the bone tunnel guide 920 in place for formation of a bone tunnel by way of the trajectory port 924.

Figure 9A:
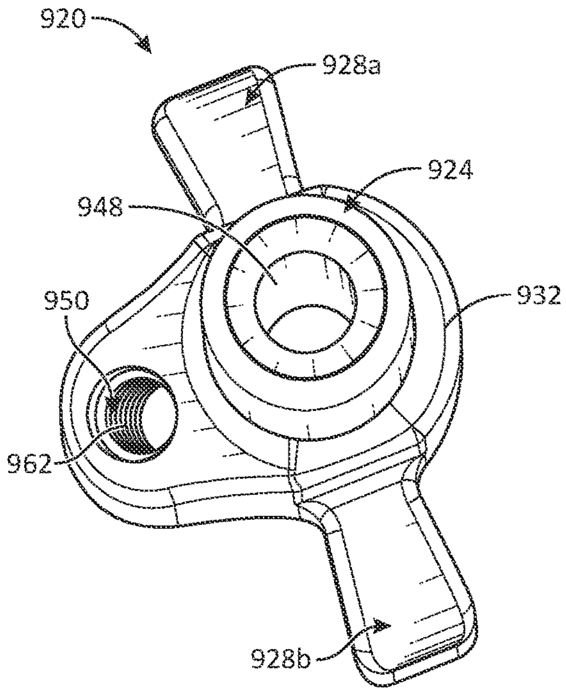
FIGS. 9A-9I illustrate views of a bone tunnel guide of the system of FIG. 8, according to one embodiment.
Figure 9B:
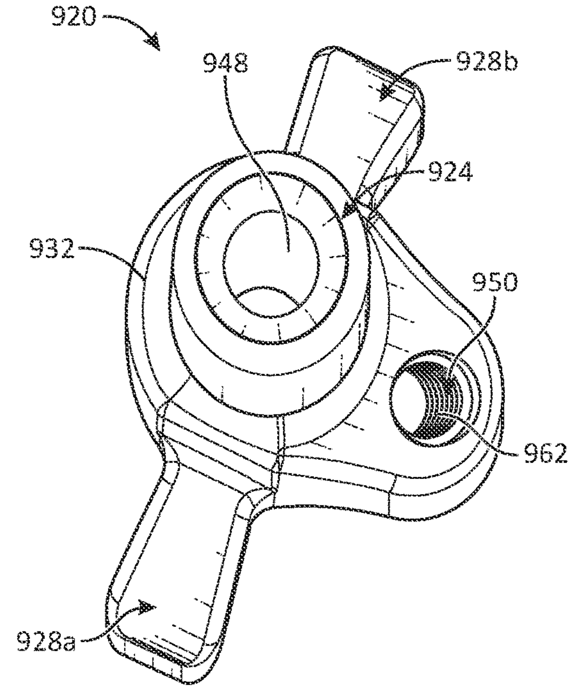
Figure 9C:
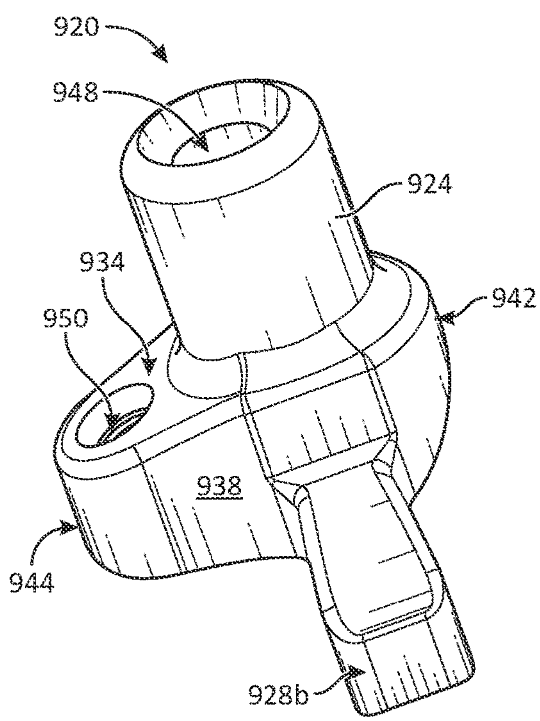
Figure 9D:
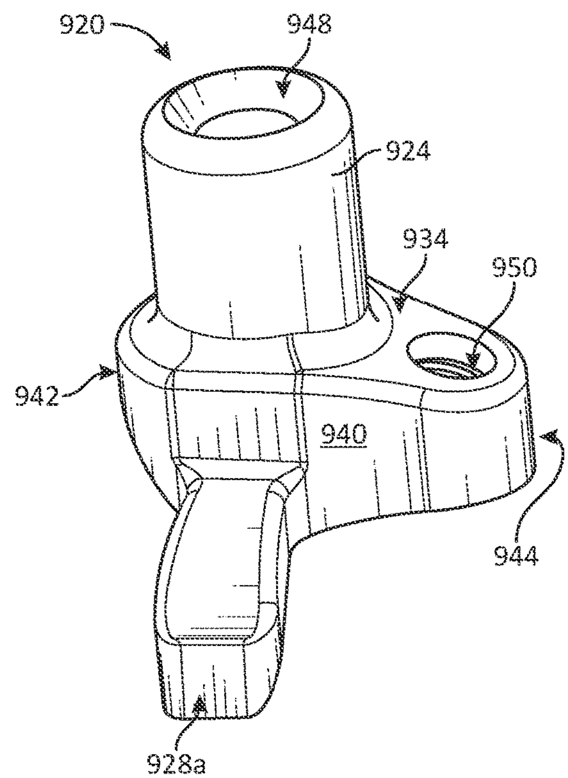
Figure 9E:
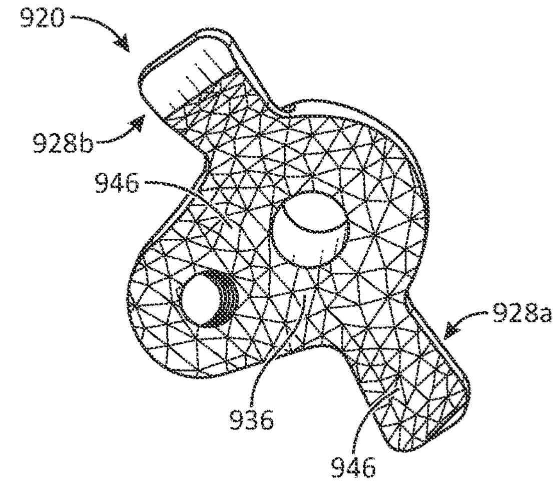
Figure 9F:
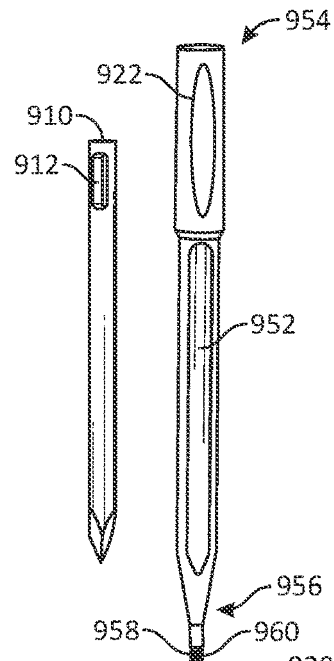
Figure 9F:
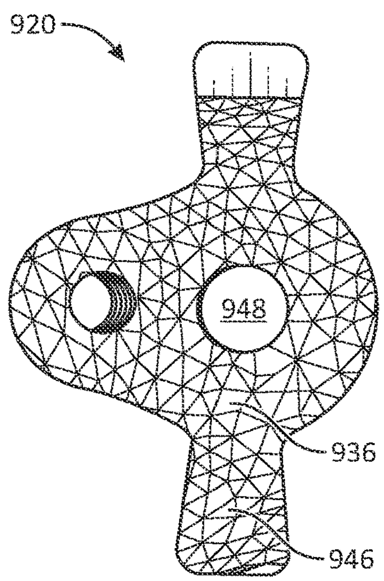
Figure 9G:
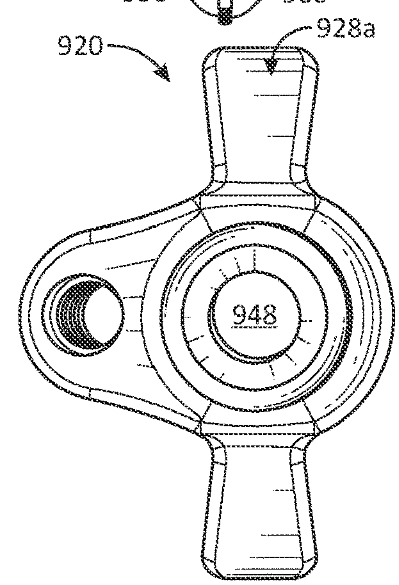
Figure 9H:
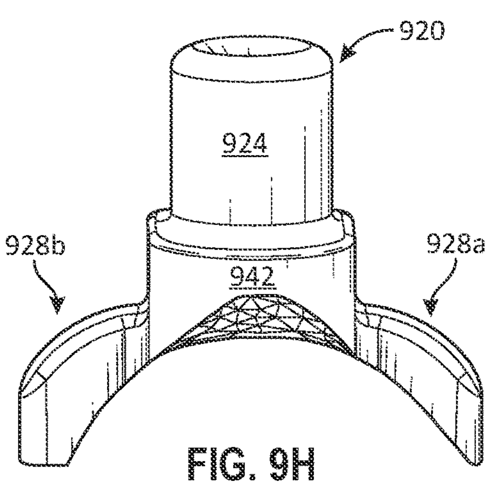
Figure 9I:
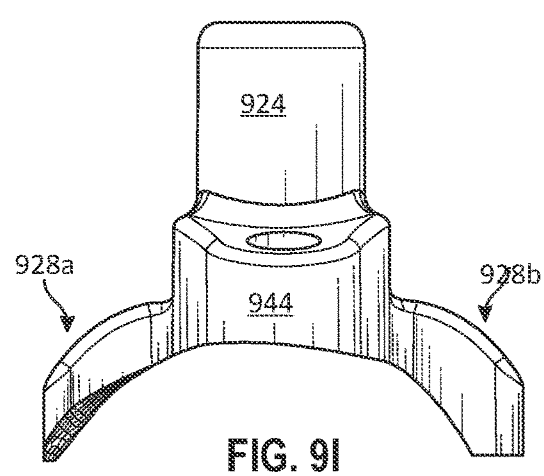

The bone tunnel guide 920 includes a superior side 934, an inferior side 936, a medial side 938, a lateral side 940, a posterior side 942, and an anterior side 944. FIG. 9A is a perspective view. FIG. 9B is a perspective view. FIG. 9C is a medial side perspective view. FIG. 9D is a lateral side perspective view. FIG. 9E is an inferior side perspective view. FIG. 9F is an inferior side view. FIG. 9G is a superior side view. FIG. 9H is a posterior side view. FIG. 9I is an anterior side view.

The bone engagement feature 928 serves to facilitate registration of the bone tunnel guide 920 to a surface of a bone and/or to one or more landmarks of the bone. The bone tunnel guide 920 can include one, two, or more bone engagement features 928. In the illustrated embodiment, the bone tunnel guide 920 includes two bone engagement features 928*a*,928*b*. A bone engagement feature 928, may be sized, shaped, positioned, and/or oriented to engage at least a portion of a bone of a patient such that the bone engagement feature 928 positions the bone tunnel guide 920 in a position that corresponds to a modeled position of a bone tunnel guide model engaging a bone model. The bone model may be a model of at least a portion of a bone of a patient. In the bone tunnel guide model, the bone engagement feature 928 are also models. The modeled bone engagement feature(s) 928 can be created when the bone tunnel guide 920 is fabricated.

Advantageously, the present disclosure includes embodiments that may include one or more aspects that are patient-specific. Since the bone tunnel guide 920 is configured, designed, and fabricated based on and for a particular patient as well as the needs, instructions, expertise, experience, and/or preferences of that patient's surgeon, a variety of aspects of the bone tunnel guide 920 can be patient-specific. Alternatively, or in addition, certain features of the soft tissue rearrangement system 800 such as the bone engagement feature 928 can include at least one patient-specific aspect that is unique to the patient.

For example, in one embodiment, a bone engagement feature 928 can include a bone engagement surface 946 on a bone-facing surface (e.g., inferior side 936) of the bone engagement feature 928. FIG. 9E and FIG. 9F illustrate examples of the bone engagement features 928 that include a bone engagement surface 946. In one embodiment, a bone engagement surface 946 is on a single bone engagement feature 928. In another embodiment, a bone engagement surface 946 may span a bone engagement feature 928 and include an inferior side 936 of the body 932 and/or an inferior side of one or more other bone engagement features 928.

Alternatively, or in addition, the bone engagement surface 946 can be configured to engage at least one landmark of the bone of the patient. For example, when in a desired position, a bone engagement feature 928 may cover a bone spur that extends from a surface of the bone. Accordingly, the bone engagement feature 928 and/or bone engagement surface 946 can be configured to include an indentation or void shaped to accept and engage with the bone spur, when the bone tunnel guide 920 is in the planned/desired position.

In one embodiment, the bone engagement surface(s) 946 is configured such that the bone engagement surface 946 forms substantially a mirror image of a bone surface. For example, the bone engagement surface 946 may correspond to a surface of a bone such that bone tunnel guide 920 provides haptic feedback to a user when the bone tunnel guide 920 translates to the position corresponding to the modeled position of the bone tunnel guide model engaging the bone model. This means a surgeon can position a bone tunnel guide 920 in an approximate position to the modeled position and then translate the bone tunnel guide 920 medially, laterally, anteriorly, posteriorly, or the like until the bone engagement surface 946 and/or the bone engagement feature(s) 928, alone or together with the bone engagement surface 946, provide that haptic feedback to a surgeon confirming that the bone tunnel guide 920 has now assumed the substantially same position on the bone as the modeled position used to design the bone tunnel guide 920.

Alternatively, a bone engagement feature 928 may be included in the bone tunnel guide 920 to specifically engage with a particular landmark at, or near, a planned position for the bone tunnel guide 920 on the bone. For example, suppose a bone spur extends from a patient's bone just posterior to a planned position for the bone tunnel guide 920. A user may request (e.g., by way of user instructions 604) that another bone engagement feature 928 be added to the design, a bone engagement feature 928 that extends posteriorly to cover/include/engage with that bone spur. In this manner, certain landmarks and/or landmark configurations can be accounted for and/or used to facilitate the accurate and precise positioning of the bone tunnel guide 920 during a planned surgical procedure. Consequently, a number of bone engagement features 928 included in the bone tunnel guide 920, as well as the size, shape, configuration, position, and/or orientation of each bone engagement feature 928 can be determined at least partially by user instructions 604. For example, a surgeon may request that one bone engagement feature 928 be made wider to provide greater registration with bone surface in that area of the bone during the surgical procedure.

Advantageously, a user may define and/or determine how many bone engagement features 928 are included in a bone tunnel guide 920. Alternatively, or in addition, a number of different bone tunnel guides 920 may be included in a soft tissue rearrangement system 800 which can be used intra-operatively as decided by a surgeon. A user may provide initial user instructions 604 for a certain number of bone engagement features 928 of a certain configuration and then later revise that user instructions 604 to modify, add, or remove bone engagement features 928.

Advantageously, because the design and configuration of the bone tunnel guide 920 is being determined before the bone tunnel guide 920 is fabricated, changes and revisions can be readily made to a model of the bone tunnel guide 920 that is later used for fabricating the bone tunnel guide 920. In one embodiment, at least one aspect of the bone tunnel guide 920 is configured based at least partially on user directions 604 provided before the bone tunnel guide 920 is fabricated. For example, a user may provide user instructions 604 that each bone engagement feature 928 include a bone engagement surface 946 that matches a contour of a bone surface of a patient when the bone tunnel guide 920 is in a desired position during a surgical procedure.

The bone tunnel guide 920 can be fabricated using additive manufacturing, subtractive manufacturing, molding, casting, or the like. The bone tunnel guide 920 can be made from a variety of materials such as, but not limited to, polymers (e.g., polyimide (nylon) polymers, Nylene®), metal (e.g., titanium, titanium alloys, stainless-steel, stainless-steel alloys, nickel-titanium alloys), ceramic, biocompatible materials, or the like. In certain embodiments, a material is selected that will reduce the cost for the bone tunnel guide 920.

In certain embodiments, a number of bone engagement features 928 (e.g., 928*a*, 928*b*, 928*c*?) of the plurality of bone engagement features 928 may be directly proportional to a number of landmark configurations near, or at, a modeled position of a bone tunnel guide model engaging a bone model of a bone, or a portion of a bone, of a patient. For example, suppose a user provides medical imaging that is used to generate a model of one or more bones of a patient and a model of a bone tunnel guide 920 that could be used.

A user may review an initial design of the bone tunnel guide 920 and a model of the bone that will receive the bone tunnel for a surgical procedure. The user may identify four distinct landmark configurations on, at, or near where a bone tunnel is planned for the surgical procedure. Accordingly, the surgeon/user may provide user instructions 604 that four bone engagement features 928 be included in a bone tunnel guide 920 for the surgical procedure. Each of the four-bone engagement features 928 may be specifically designed and/or engineered to engage with each of the four landmark configurations. In one embodiment, one of the landmark configurations may be a bony surface; another landmark configuration may be a joint; landmark configurations may be a bone distal to a joint; another landmark configurations may be a different part of a bone surface. In this example, the number of landmark configurations (four) is directly proportional to the number of bone engagement features 928 (four).

Once a technician or engineer designs a model of the bone tunnel guide 920 together with one or more models of bones of a patient, the technician may send the designed model to the user or otherwise make the design available for review by the user/surgeon. A surgeon can review the model and/or the one or more modeled bones, and/or manipulate them in an interface to visualize where the model of the bone tunnel guide 920 will register to one or more bones and thus where a resulting bone tunnel can be formed in one or more bones.

Based on this review, the surgeon may have further changes and/or adjustments to the model of the bone tunnel guide 920 based on patient anatomy, steps for a planned surgical procedure, and/or surgeon preferences. With this feedback from the surgeon, the technician may make further adjustments and/or changes to the designed model of the bone tunnel guide. This process of review and revision can be repeated multiple times until the surgeon approves the design. At this point the technician can arrange for the model of the bone tunnel guide to be fabricated to create the bone tunnel guide 920. The bone tunnel guide 920 is then provided to the user for use in a surgical procedure.

In one embodiment, the bone tunnel guide 920 includes a plurality of bone engagement features 928 that each extend away from the trajectory port 924. For example, the bone engagement features 928 can extend from one or more sides of the bone tunnel guide 920. In one embodiment, the plurality of bone engagement features 928 may extend away from the trajectory port 924 radially in different directions.

In the illustrated embodiment, the bone engagement features 928 extend from opposite sides of the bone tunnel guide 920. Those of skill in the art will appreciate that the bone engagement features 928 can have various lengths, widths, and thicknesses. Furthermore, these configurations attributes of the bone engagement feature 928 may be patient-specific. Advantageously, the bone engagement features 928 also include a bone engagement surface 946 that may extend a bone engagement surface 946 on an inferior surface (inferior side 936) of the bone tunnel guide 920.

In the illustrated embodiment, one bone engagement feature 928*a* extends from the lateral side 940 and one bone engagement feature 928 extends from the medial side 938. Advantageously, the bone engagement feature 928 can provide a surgeon with confidence and assurance in the placement and positioning of the bone tunnel guide 920 on the bone because one or more of the bone engagement features 928 can be configured to engage with one or more particular landmarks on the bone (e.g., a projection, an eminence, a bone spur, a depression, a cavity, or the like). Alternatively, or in addition, the bone engagement feature 928 can include a contoured bone engagement surface 946 that can further facilitate registration of the bone engagement feature 928 and/or bone tunnel guide 920 with the bone. In this manner, a surgeon can be assured intraoperatively that the bone tunnel guide 920 is being positioned in accordance with a preoperative plan.

In certain embodiments, the bone engagement feature 928 can be shaped like a hook, a finger, a foot, an arm, a leg, or an appendage, to engage a dorsal/medial surface of bone or dorsal/lateral surface of bone. Alternatively, or in addition, the bone tunnel guide 920 may include a bone engagement feature 928 on each side (medial and lateral), together the bone engagement features 928 can engage one or more landmarks of the bone such that the surgeon can accurately position and register the bone tunnel guide 920 to the bone.

Referring to FIGS. 9A, 9B, and 9E, in one embodiment, the bone tunnel guide 920 includes a handle 922 and the body 932 includes a handle coupler 950. In the illustrated embodiment, the handle 922 is configured to secure the bone tunnel guide 920 in place during formation of a bone tunnel by way of the trajectory port 924. Those of skill in the art will appreciate that the trajectory port 924 can be used to form a bone tunnel in a variety of ways, each of which is within the scope of the present disclosure. For example, in one embodiment, a user may deploy a fastener 910 such as K-wire or a fastener 910 that includes an eye 912. After deploying the fastener 910, a user may use a cannulated drill bit to drill out bone around the fastener 910 and thereby form a bone tunnel that is coaxial with the fastener 910. In one embodiment, the user may thread a suture through the eye 912 of the fastener 910 and use the fastener 910 to pass the suture through the newly formed bone tunnel. Alternatively, or in addition, a user may use the bone tunnel guide 920 and trajectory port 924 to guide a drill bit or burr that is passed through the trajectory port 924 and into the bone to form a bone tunnel in the bone. Advantageously, a user can hold the bone tunnel guide 920 in place using the handle 922 as steps are taken to form a bone tunnel having substantially the same trajectory and/or orientation as the trajectory port 924.

The handle 922 includes shaft 952 that includes a proximal end 954 and a distal end 956. The distal end 956 includes a coupler 958. In one embodiment, the coupler 958 includes external threads 960 configured to engage with internal threads 962 of the handle coupler 950 formed in the body 932. In one embodiment, the coupler 958 is configured to be removable such that a coupler 958 of a different size or having a different coupling can be used with the same handle 922.

In the illustrated embodiment, the handle coupler 950 is closer to the anterior side 944 of the bone tunnel guide 920 and the bone engagement features 928 extend from the medial side 938 and lateral side 940. Those of skill in the art will appreciate that the handle coupler 950 may be in another position in the bone tunnel guide 920 and that the bone engagement features 928 may extend from sides other than those in the illustrated embodiment.

Figure 10A:
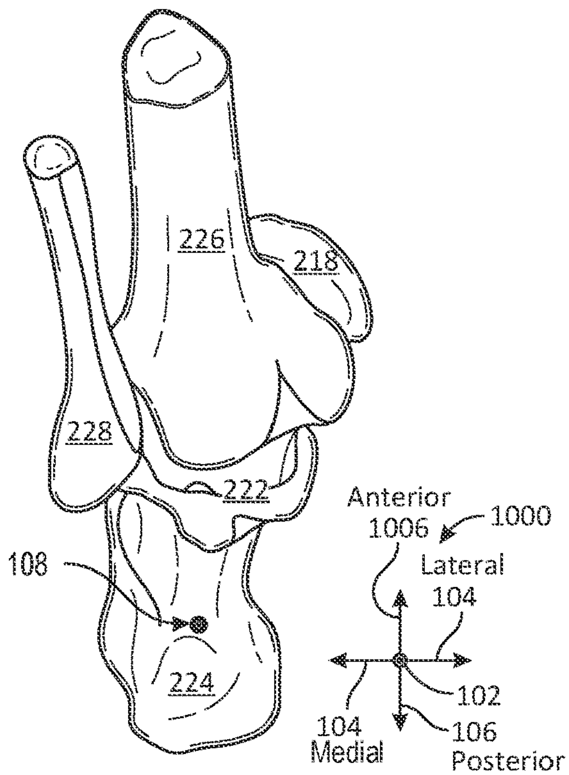
FIG. 10A illustrates a superior perspective view of a foot and ankle including the calcaneus, a tibia, fibula, talus, and navicular.

FIG. 10A illustrates a superior perspective view of a foot and ankle including the calcaneus 224, a tibia 226, fibula 228, talus 222, and navicular 218. FIG. 10A also illustrates a three-dimensional axis 1000. The three-dimensional axis 1000 includes a cephalad-caudal axis 1002, a medial-lateral axis 1004, and an anterior-posterior axis 1006.

Generally, in a soft tissue rearrangement such as a tendon deployment surgical procedure a surgeon seeks to position the tendon in an optimal location on, or in, a bone to provide improved mobility and use of an extremity. For example, in a Flexor Hallucis Longus (FHL) tendon transfer, a surgeon plans to position a relocated end of an FHL tendon on a dorsal surface of a calcaneus 224, centered along the medial-lateral axis 1004. In one embodiment, a surgeon may plan to position the FHL tendon approximately where a superior target marker 1008 is illustrated in FIG. 10A. The superior target marker 1008 indicates where a surgeon desires the attachment point to be for a deployed tendon (e.g., either a transferred tendon or attachment of another tendon or graft).

Conventionally, a surgeon may determine the attachment point represented by the superior target marker 1008 intra-operatively and may rely on various techniques including x-rays, fluoroscopy, and the like. However, determining an optimal location for superior target marker 1008 can be a challenge. Even using X-rays, such as a C-arm, offer very little help to a surgeon since the C-arm can only provide a limited view given the angle at which the X-ray can be taken of the dorsal side of the calcaneus 224.

If the location (e.g., superior target marker 1008) is too far medial or too far lateral along medial-lateral axis 1004 this can lead to complications and problems later for the patient, such as gait problems and/or subtalar arthritis, and the like. If the location (e.g., superior target marker 1008) is too far anterior or too far posterior along anterior-posterior axis 1006 this can lead to contact and/or disruption of plantar nerves, vessels, disconnecting of bone spurs on a plantar surface, and/or other neurovascular constructs on the plantar side of the calcaneus 224.

In an FHL tendon transfer, the FHL tendon (which is a smaller tendon) is being tasked to provide plantar flexion in place of a damaged or resected Achilles tendon. Consequently, positioning the attachment point for the transferred FHL can be important to get an optimal desired biomechanical pull on the calcaneus, to get the optimal lever arm for plantar flexion.

Advantageously, the tendon trajectory guide 920 facilitates locating and positioning the deployed tendon at an attachment point indicated by the superior target marker 1008 with each tendon deployment procedure. The tendon trajectory guide 920 ensures that the attachment point is centered along the medial-lateral axis 1004 between the medial and lateral sides of the calcaneus 224.

As explained above, the tendon trajectory guide 920 can be positioned, sized, configured, and oriented and/or trajectories set for the tendon trajectory guide 920 preoperatively using bone models. Additionally, a surgeon can provide a prescription for the location of the attachment point (e.g., superior target marker 1008) to account for other conditions of a particular patient such as bone spurs on the plantar surface of the calcaneus 224.

In addition, the bone engagement surface 946 of the tendon trajectory guide 920 is defined to match and correspond to the surface contour and/or landmarks on a dorsal surface of the bone, such as the calcaneus 224. This means that once the dorsal surface of the calcaneus 224 is exposed a surgeon can seat the tendon trajectory guide 920 in the same location and position and orientation as used preoperatively in models. Advantageously, the bone engagement surface 946 matches to the surface of the calcaneus 224 and/or any landmarks of the calcaneus 224 such that the surgeon can position the tendon trajectory guide 920 on the superior target marker 1008 each time and in each procedure. Such consistency can improve patient care.

Alternatively, or in addition, a surgeon may save time in the operating room because an imaging machine such as a C-arm may not be needed to check positioning and/or trajectory before the surgical procedure proceeds. Once the tendon trajectory guide 920 is registered to the dorsal surface of the calcaneus 224 the surgeon is assured that deployment of a hole, opening, bone tunnel, or fastener 910 through the trajectory port 924 will match a location/trajectory determine preoperatively. Thus, many of the challenges of determining the superior target marker 1008 are overcome using the tendon trajectory guide 920.

Figure 10B:
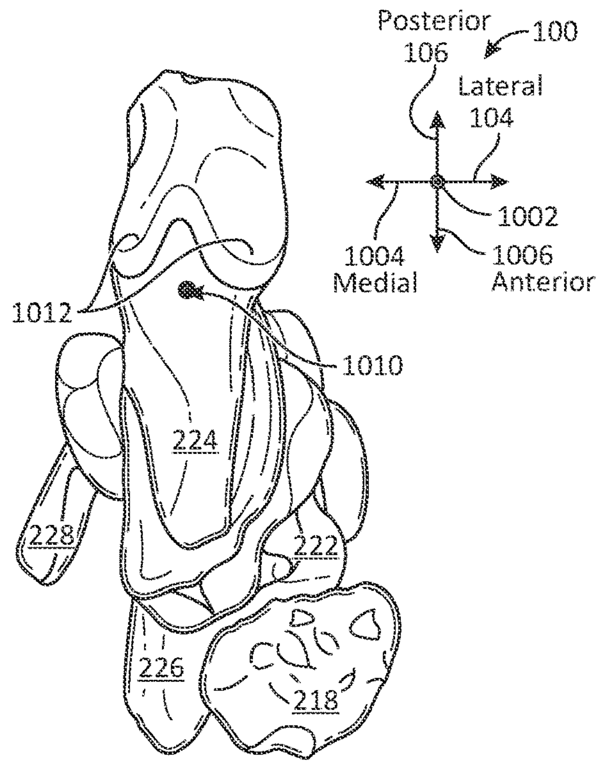
FIG. 10B illustrates an inferior perspective view of a foot and ankle including the calcaneus, a tibia, fibula, talus, and navicular.

FIG. 10B illustrates an inferior perspective view of a foot and ankle including the calcaneus 224, a tibia 226, fibula 228, talus 222, and navicular 218. FIG. 10B illustrates an exit point indicated in FIG. 10B by an inferior target marker 1010 that identifies where a trajectory set by the tendon trajectory guide 920 will cause a pin, drill bit, or cutting tool to exit cortical bone of the calcaneus 224 opposite the superior target marker 1008.

The position of the superior target marker 1008 and the trajectory set by the trajectory port 924 of the tendon trajectory guide 920 determine the location of the inferior target marker 1010. Surgeons may have a specific set of instructions and/or a prescription for the location of the inferior target marker 1010. Multiple factors can influence the location of the inferior target marker 1010 and the trajectory. In one embodiment, the surgeon wants to position the inferior target marker 1010 a millimeter, or so, anterior (along anterior-posterior axis 1006) to two posterior tuberosities 1012 on the plantar side of the calcaneus 224. These tuberosities can serve as landmarks for designing and fabricating the tendon trajectory guide 920. If the inferior target marker 1010 is too far posterior, along anterior-posterior axis 1006, the lever arm of the FHL may be impacted. If the inferior target marker 1010 is too far anterior, along anterior-posterior axis 1006, the exit point may interfere with arteries and/or nerves on the plantar side of the foot. In certain embodiments, a patient may have a bone spur near the tuberosities 1012, in such a case, a surgeon may provide instructions to position the inferior target marker 1010 anterior to the bone spur.

Figure 10C:
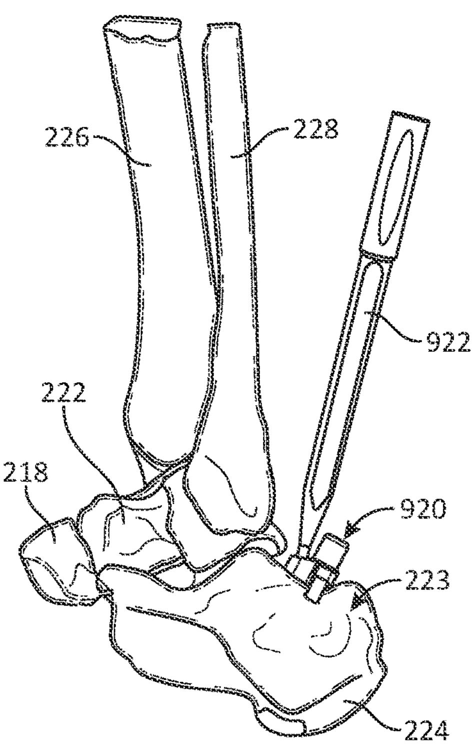
FIGS. 10C-10D illustrate different stages of performing a tendon placement/transfer procedure.
Figure 10D:
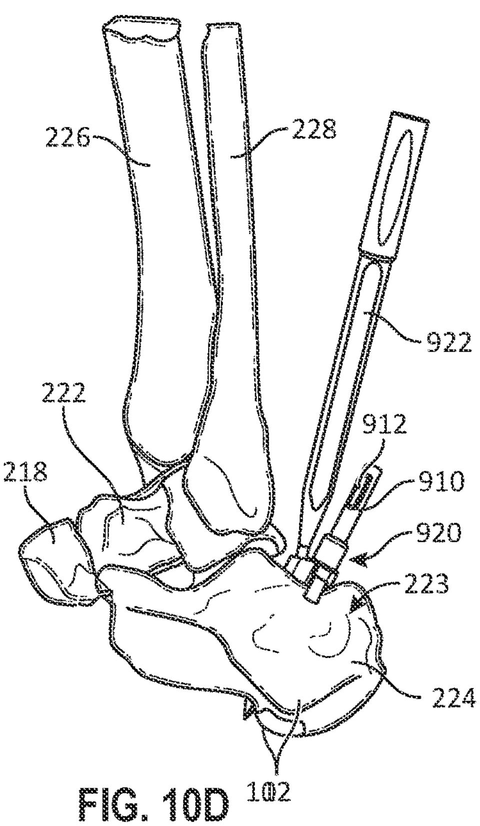

FIGS. 10C-10D illustrate different stages of performing a tendon placement procedure (e.g., an FHL tendon transfer) using the soft tissue rearrangement system 800, according to one embodiment. Typically, the initial approach for a tendon placement procedure, such as an FHL tendon transfer is on the posterior side of the foot and the calcaneus 224. FIGS. 10A and 10B illustrate where a surgeon has indicated the location for the attachment point, the superior target marker 1008 and the inferior target marker 1010 and the desired trajectory.

Referring to FIG. 10C, during an exemplary tendon placement procedure, such as an FHL tendon transfer, an initial step, using a posterior approach, may be to cut through, or to resect, the Achilles tendon proximal to the calcaneus 224. Next, facia between the Achilles tendon and the distal end of the fibula 228 and tibia 226 may be dissected and released to reveal the FHL tendon and posterior aspect of the calcaneus 224.

In certain techniques, or methods of use, a surgeon may want to resect a bursal projection 223 (or tuberosity) on the posterosuperior corner of the calcaneus 224. This can be done in a few ways.

In one embodiment, a surgeon may place the tendon trajectory guide 920 on the target location, aligning a center axis of the opening 948 with the superior target marker 1008 location on the calcaneus 224. FIG. 10C illustrates the tendon trajectory guide 920 positioned on the calcaneus 224 by way of seating the tendon trajectory guide 920 on the dorsal surface of the calcaneus 224. Advantageously, the bone engagement surface 946 engages the surface of the calcaneus 224 to register the tendon trajectory guide 920 in the desired location. In certain embodiments, the bone engagement features 928 can facilitate positioning the tendon trajectory guide 920 in the desired position. In one embodiment, the tendon trajectory guide 920 may be referred to as a pin guide.

The soft tissue rearrangement system 800 may include a handle 922 coupled to the tendon trajectory guide 920. In one embodiment, external threads of the handle 922 may engage internal threads of a handle coupler to connect the handle 922 to the tendon trajectory guide 920. The handle 922 can serve to facilitate positioning, placement, registration, and/or removal of the tendon trajectory guide 920 during one or more stages of a procedure.

Next, a surgeon may deploy a fastener 910 through the opening 948 and into the calcaneus 224. This stage is shown in FIG. 10D, the fastener 910 passes through the opening 948 into the calcaneus 224 and out the opposite side. Advantageously, the positioned tendon trajectory guide 920 and the trajectory of the trajectory port 922 ensures that the distal end of the fastener 910 exits the cortical bone at the inferior target marker 1010.

In one embodiment, the fastener 910 is an eyelet pin that includes an eye 912. The fastener 910 may be supplied with the tendon trajectory guide 920 and/or may be supplied in a conventional tendon transfer surgical system/kit/tray. With the fastener 910 deployed, the surgeon may then remove the tendon trajectory guide 920 by sliding it off of the fastener 910.

Next, in certain embodiments, a surgeon may remove the fastener 910 and then resect the bursal projection 223. After resection, the removed fastener 910 leaves a hole in the calcaneus 224 that can be used to redeploy the fastener 910 into the hole in the same location and trajectory. The fastener 910 in the same hole can then be used to guide a reamer over the fastener 910 to form a bone tunnel coaxial with the fastener 910. Alternatively, or in addition, a surgeon may use the hole formed by the fastener 910 to form a bone tunnel coaxial using other techniques.

Alternatively, or in addition, with the tendon trajectory guide 920 and fastener 910 in place, the surgeon can next remove the tendon trajectory guide 920 and leave the fastener 910 in place. Next, the surgeon may resect the bursal projection 223 all around the fastener 910. The method may then proceed with the surgeon reaming a bone tunnel around the fastener 910 such that the bone tunnel is coaxial with the fastener 910.

Next, the surgeon may follow traditional steps to attach a tendon to the attachment point and along a trajectory provided by the tendon trajectory guide 920 using a variety of conventional tendon transfer kits/systems/instruments or the like. For example, a surgeon may thread a suture that is whip stitched to an end of the FHL and pass the suture through a proximal eyelet of the fastener 910. Next, the surgeon may press the fastener 910 through the bone tunnel and out the plantar (distal) opening on the inferior surface of the calcaneus 224. In this manner, the FHL is threaded into the bone tunnel. The FHL may then be secured and/or fixated in the bone tunnel using conventional techniques and/or implants and/or fasteners.

Those of skill in the art will appreciate that the tendon trajectory guide 920 can be used for a variety of tendon attachment/positioning procedures in hindfoot, midfoot, forefoot, hand, wrist, elbow, shoulder, and/or the like. Furthermore, patient-specific guides such as the exemplary tendon trajectory guide 920 can be used for attaching a tendon or ligament to a bone in a variety of ways, a variety of surgical procedures and/or to accommodate a variety surgeon preferences or instructions. For example, with an FDL transfer, a surgeon may decide to attach the tendon medially and drill a blind hole using a guide such as the tendon trajectory guide 920. One skilled in the art can appreciate that the presented embodiments may be modified, revised, or repositioned to address a surgeon's particular angles, approach, entry locations and/or preferences.

In another example, embodiments of the tendon trajectory guide 920 can be used for ax axial tendon transfer in which a posterior tibial tendon (aka tibialis posterior tendon) is rerouted from attachment to the navicular 218 to pass between the tibia 226 and fibula 228 down the dorsal side of the midfoot and attached to the lateral cuneiform 206. In such a procedure, the tendon trajectory guide 920 can seat on the lateral cuneiform 206 to identify the attachment point and/or trajectory for a fixation system.

As another example, a tendon trajectory guide 920 can be used for a tibialis anterior tendon transfer in which the tibialis anterior tendon (TAT) is transferred from the inside medial cuneiform 202 and reattached to either the lateral cuneiform 206 or the cuboid 220. In such a procedure, the tendon trajectory guide 920 can seat on either the lateral cuneiform 206, the cuboid 220 or both to identify the attachment point and/or trajectory for a fixation system. This procedure can be used to address club foot conditions and flat foot conditions.

In another embodiment, the tendon trajectory guide 920 can be a posterior tibial tendon transfer guide used for a surgical procedure to transfer the attachment point from navicular and relocate the tendon through the leg to the intermediate or lateral cuneiform to address a dropfoot condition.

In another embodiment, the tendon trajectory guide 920 can be used for a Jones tenosuspension in which an extensor hallucis tendon is transferred from a phalanx of a hallux and transferred to the first metatarsal neck to address a mallet toe condition or cavus foot condition.

In another embodiment, the tendon trajectory guide 920 can be used to transfer an extensor digitorum longus (EDL) from toes of a patient to the midfoot and attach to the lateral cuneiform or intermediate cuneiform to address a cavus foot condition or a claw toe condition.

In another embodiment, the tendon trajectory guide 920 can be used for an extensor hallucis longus (EHL) transfer to address a ruptured tibialis anterior tendon (TAT). In this procedure, one or more tendons connected to the interphalangeal joint (IPJ) of the hallux (big toe) are transferred to the medial cuneiform to address a dropfoot condition.

In another embodiment, the tendon trajectory guide 920 can be used to transfer a tibialis anterior tendon (TAT) to the calcaneus to address a congenital calcaneal valgus condition.

In another embodiment, the tendon trajectory guide 920 can be used to relocate an Achilles tendon from an original attachment point on the calcaneus to a new attachment point on the calcaneus.

Those of skill in the art will appreciate that the apparatuses, systems, and methods of the present disclosure can be used other surgical procedure guides beyond tendon trajectory guides and/or resection guides. For example, the apparatuses, systems, and methods of the present disclosure can be used to provide targeting guides that are patient-specific and which can be used in a variety of surgical procedures. For example, the apparatuses, systems, and methods of the present disclosure can be used to provide a targeting guide for deltoid ligament reconstruction and/or for lateral collateral ankle ligament reconstruction.

In such embodiments, the targeting guide can be used to facilitate positioning of bone tunnels and/or attachment points for an allograft and/or a tendon and/or ligament anchoring system in the sustentaculum tali of the calcaneus, talus, and/or medial malleoli.

Furthermore, in such embodiments, the targeting guide can be used to facilitate positioning of bone tunnels and/or attachment points for lateral ankle ligament reconstruction for attachment points for an allograft and/or a tendon and/or ligament anchoring system for the anterior talo-fibular ligament (ATFL) and/or the calcaneofibular ligament (CFL) for the calcaneus, talus, and/or fibula.

Furthermore, in such embodiments, the targeting guide can be used to facilitate positioning of bone tunnels and/or attachment points for constructs and/or ligaments for a plantar calcaneonavicular ligament ("spring ligament") repair of the navicular and/or talus.

In yet another example, the tendon trajectory guide 920 can be used for a flexor digitorum longus (FDL) transfer in which the FDL tendon is transferred from its normal attachment point to attach to an inferior side of the navicular 218. Transfer of the FDL tendon to the navicular 218 can be used to address a flat foot condition or when the posterior tibial tendon (PTT) is not performing properly.

Figure 11A:
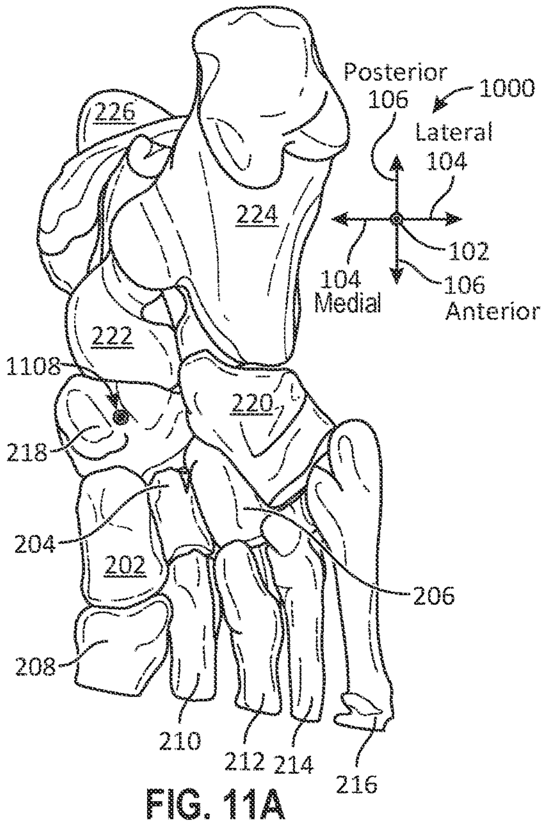
FIG. 11A illustrates an inferior perspective view of a foot and ankle.

FIG. 11A illustrates an inferior perspective view of a foot and ankle including the medial cuneiform 202, intermediate cuneiform 204, lateral cuneiform 206, first metatarsal 208, second metatarsal 210, third metatarsal 212, fourth metatarsal 214, fifth metatarsal 216, navicular 218, cuboid 220, calcaneus 224, a tibia 226, and talus 222. FIG. 11A also illustrates the three-dimensional axis 1000. The three-dimensional axis 1000 includes the cephalad-caudal axis 1002, the medial-lateral axis 1004, and the anterior-posterior axis 1006.

Generally, in a tendon deployment a surgeon seeks to position the tendon in an optimal location on, or in, a bone to provide improved mobility and use of an extremity. For example, in an FDL tendon transfer, a surgeon plans to position a resected end of an FDL tendon on a plantar/inferior surface of a navicular 218. In one embodiment, a surgeon may plan to position the FDL tendon approximately where an inferior target marker 1108 is illustrated in FIG. 11A. The inferior target marker 1108 indicates where a surgeon desires the attachment point to be for a deployed tendon (e.g., either a transferred tendon or attachment of another tendon or graft).

Conventionally, a surgeon may determine the attachment point represented by the inferior target marker 1108 intra-operatively and may rely on various techniques including x-rays, fluoroscopy, and the like. However, determining an optimal location for inferior target marker 1108 can be a challenge.

If the location (e.g., inferior target marker 1108) is too far medial or too far lateral along medial-lateral axis 1004 this can lead to complications and problems later for the patient. If the location (e.g., inferior target marker 1108) is too far anterior or too far posterior along anterior-posterior axis 1006 this can lead to complications.

Advantageously, the tendon trajectory guide 1120 facilitates locating and positioning the deployed tendon at an attachment point indicated by the inferior target marker 1108 with each tendon deployment procedure. As explained above, the tendon trajectory guide 1120 can be positioned, sized, configured, and oriented and/or trajectories set for the tendon trajectory guide 1120 preoperatively using bone models. Additionally, a surgeon can provide a prescription for the location of the attachment point (e.g., inferior target marker 1108) to account for other conditions of a particular patient.

In addition, the bone engagement surface 1126 of the tendon trajectory guide 1120 is defined to match and correspond to the surface contour and/or any landmarks on a surface of the bone, such as the navicular 218. This means that once the plantar surface of the navicular 218 is exposed a surgeon can seat the tendon trajectory guide 1120 in the same location and position and orientation as used preoperatively. Advantageously, the bone engagement surface 1126 matches to the surface of the navicular 218 and/or any landmarks of the navicular 218 such that the surgeon can position the bone engagement surface 1126 on the inferior target marker 1108 accurately each time and in each procedure. Once the bone engagement surface 1126 is registered to the plantar surface of the navicular 218 the surgeon is assured that deployment of a hole, opening, bone tunnel, or fastener 910 through the trajectory port will match the location/trajectory determine preoperatively. Thus, many of the challenges of determining the inferior target marker 1108 are overcome using the tendon trajectory guide 1120.

Figure 11B:
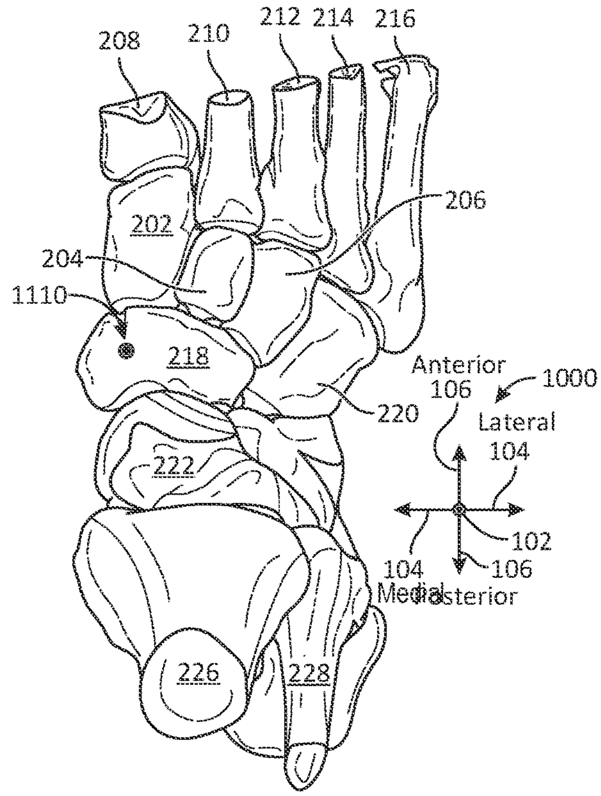
FIG. 11B illustrates a superior perspective view of a foot and ankle.

FIG. 11B illustrates a superior perspective view of a foot and ankle including the tibia 226, fibula 228, talus 222, and navicular 218. FIG. 11B illustrates an exit point indicated in FIG. 11B by a superior target marker 1110 that identifies where a trajectory set by the tendon trajectory guide 1120 (See FIG. 11C) will cause a pin, drill bit, or cutting tool to exit cortical bone of the navicular 218 opposite the inferior target marker 1108.

The position of the inferior target marker 1108 and the trajectory set by the trajectory port of the tendon trajectory guide 1120 determine the location of the superior target marker 1110. Surgeons may have a specific set of instructions and/or a prescription for the location of the superior target marker 1110. Multiple factors can influence the location of the superior target marker 1110 and the trajectory.

Figure 11C:
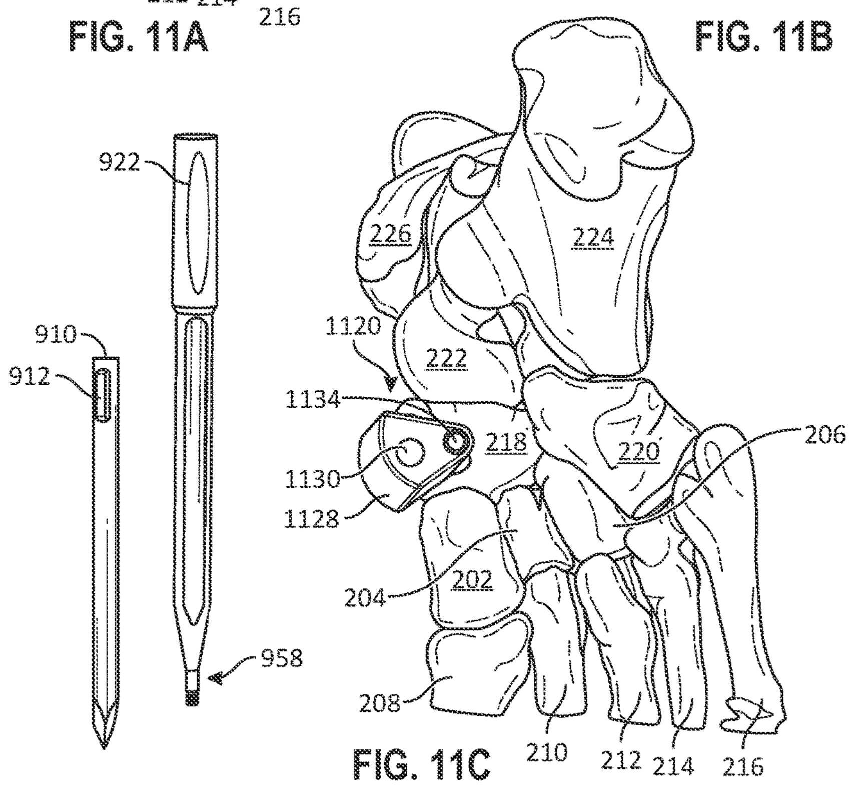
FIG. 11C illustrates a stage of performing a tendon placement procedure.

FIG. 11C illustrates a stage of performing a tendon placement procedure (e.g., an FDL tendon transfer to the navicular 218) using the tendon deployment system 1000, according to one embodiment. Typically, the initial approach for a tendon placement procedure, such as an FDL tendon transfer to the navicular 218 is on the inferior side of the foot and the navicular 218. FIGS. 11A and 11B illustrate where a surgeon has indicated the location for the attachment point, the inferior target marker 1108 and the superior target marker 1110 and the desired trajectory.

Referring to FIG. 11C, during an exemplary tendon placement procedure, such as an FDL tendon transfer to the navicular 218, an initial step, is to expose the plantar surface of the navicular 218.

Next, a surgeon may place the tendon trajectory guide 1120 on the target location, aligning a center axis of the opening 1134 with the inferior target marker 1108 location on the navicular 218. FIG. 12C illustrates the tendon trajectory guide 1120 positioned on the navicular 218 by way of seating the tendon trajectory guide 1120 on the plantar surface of the navicular 218. Advantageously, the bone engagement surface 1126 engages the surface of the navicular 218 to register the tendon trajectory guide 1120 in the desired location. In certain embodiments, the tendon trajectory guide 1120 may include landmark registration features that can facilitate positioning the tendon trajectory guide 1120 in the desired position. In one embodiment, the tendon trajectory guide 1120 may be referred to as a pin guide.

The tendon deployment system 1000 may include a handle 922 that can couple to the tendon trajectory guide 1120 by way of a coupler 958. In one embodiment, external threads of the handle 922 may engage internal threads of the coupler 958 to connect the handle 922 to the tendon trajectory guide 1120. The handle 922 can serve to facilitate positioning, placement, registration, and/or removal of the tendon trajectory guide 1120 during one or more stages of a procedure.

Next, a surgeon may deploy a fastener 910 through the opening 1134 and into the navicular 218. The fastener 910 may pass through the opening 1134 into the navicular 218 and out the opposite side. Advantageously, the positioned tendon trajectory guide 1120 ensures that the distal end of the fastener 910 exits the cortical bone at the superior target marker 1110.

In one embodiment, the fastener 910 is an eyelet pin having an eyelet 912. The fastener 910 may be supplied with the tendon trajectory guide 1120 and/or may be supplied in a conventional tendon transfer surgical system/kit/tray. With the fastener 910 deployed, the surgeon may then remove the tendon trajectory guide 1120 by sliding the tendon trajectory guide 1120 off of the fastener 910.

With the tendon trajectory guide 1120 and fastener 910 in place, the surgeon can next remove the tendon trajectory guide 1120 and leave the fastener 910 in place. The method may then proceed with the surgeon reaming a bone tunnel around the fastener 910 such that the bone tunnel is coaxial with the fastener 910. Next, the surgeon may follow traditional steps to attach a tendon (e.g., the FDL tendon) to the attachment point and along a trajectory provided by the tendon trajectory guide 1120 using a variety of conventional tendon transfer kits/systems/instruments or the like. For example, a surgeon may thread a suture that is whip stitched to an end of the FDL and pass the suture through a proximal eyelet of the fastener 910. Next, the surgeon may press the fastener 910 through the bone tunnel and out the dorsal (distal) opening on the superior surface of the navicular 218. In this manner, the FDL is threaded into the bone tunnel. The FDL may then be secured and/or fixated in the bone tunnel using conventional techniques and/or implants and/or fasteners.

A patient may present with a variety of conditions. To correct or mitigate these conditions, a tendon trajectory guide 1120 according to the present disclosure can be used to address dorsiflexion, plantar flexion, angular correction of a bone segment or any bone, flat foot, club foot, or a variety of foot, hand, or joint conditions. Those of skill in the art will appreciate that the tendon trajectory guide 1120 may also include bone engagement features, resection features, or the like depending on the needs of a surgeon for a particular surgical procedure.

For example, FIG. 11C illustrates an embodiment of a tendon trajectory guide 1120 that includes a bone engagement feature 1128. The bone engagement feature 1128 extends from a body of the tendon trajectory guide 1120 dorsally along a medial side of the navicular 218. In certain embodiments, the initial dimensions of the bone engagement feature 1128 may be set by a technician working with a model of the tendon trajectory guide 1120 and bone models of bones such as the navicular 218 of a patient. However, before the tendon trajectory guide 1120 a surgical procedure is performed using the tendon trajectory guide 1120 a surgeon reviews the design of the tendon trajectory guide 1120 and can revised or adjust the configuration of the bone engagement feature 1128. In this manner, the surgeon remains in control and makes the determination as to what the final design of the tendon trajectory guide 1120 should be. A surgeon can for example, request that the bone engagement feature 1128 extend less dorsally and/or extend more anteriorly, etc. The surgeon may have many reasons for making these adjustments. However, the benefit of the present disclosure is that the design of the tendon trajectory guide 1120 can be revised by the surgeon until the design matches the surgeon's needs and/or preferences for the surgical procedure.

In the illustrated embodiment, the bone engagement feature 1128 can also include a bone engagement surface 1126 on a surface that contacts and/or faces a surface of the navicular 218. Alternatively, or in addition, the bone engagement feature 1128 can include one or more landmark registration features 1124 that can further assist a surgeon in positioning the tendon trajectory guide 1120 during a surgical procedure.

Those of skill in the art will appreciate that the number, size, shape, and/or other configuration aspects of a bone engagement feature 1128, in certain embodiments, can be directly proportional to a landmark configuration of a bone indicated on a bone model of one or more bones of a patient. This means, in certain embodiments, for example, that where a surface and/or area of bone includes three landmarks with a particular relationship between them, the tendon trajectory guide 1120 can include three corresponding bone engagement features 1128.

FIGS. 12A-12E illustrate different views of one embodiment of a tendon trajectory guide 1120 for the navicular 218. The tendon trajectory guide 1120 includes a body 1134 having an anterior side 1136, a posterior side 1138, a medial side 1140, a lateral side 1142, a superior side 1144, and an inferior side 1146. The tendon trajectory guide 1120 includes a bone engagement surface 1126 and opening 1134. In certain embodiments, the tendon trajectory guide 1120 may include one or more landmark registration features 1124.

A landmark registration feature 1124 can be any structure of the tendon trajectory guide 1120 that engages with, is configured to engage with, contacts and/or connects to a landmark of a bone. In the illustrated embodiment, the landmark registration feature 1124 is a lip that is configured to engage with a bone process that extends from and/or shapes the bone (e.g., navicular 218). Advantageously, a surgeon can request additional landmark registration features 1124 and/or can modify one or more landmark registration feature 1124 such that they are larger or smaller, according to their own needs and/or preferences for the surgical procedure.

In certain embodiments, a landmark registration feature 1124 can be shaped like and/or function as a probe or finder and a surgeon can use the landmark registration feature 1124 to assist in positioning the tendon trajectory guide 1120. In another embodiment, a tendon trajectory guide 1120 can include a landmark registration feature 1124 separate and independent of whether or not the tendon trajectory guide 1120 includes a bone engagement feature 1128.

Figure 12A:
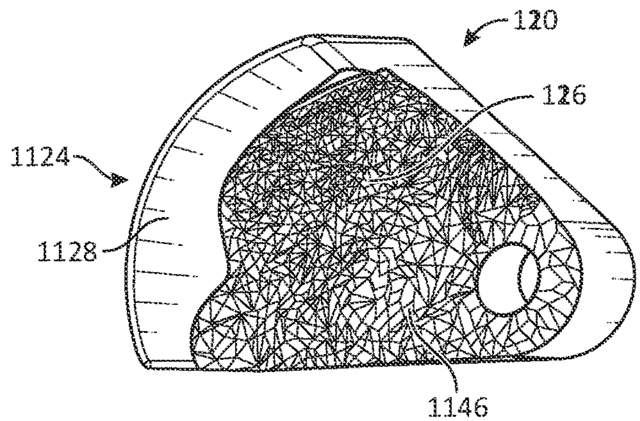
FIGS. 12A-12E illustrate different views of one embodiment of a tendon trajectory guide.
Figure 12B:
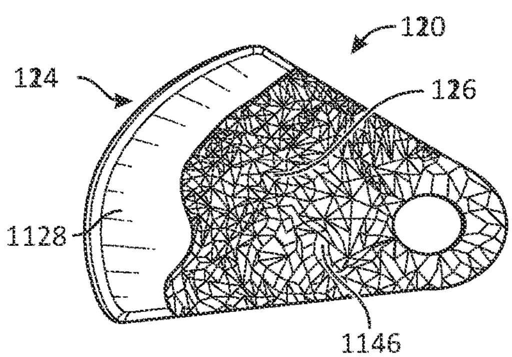
Figure 12C:
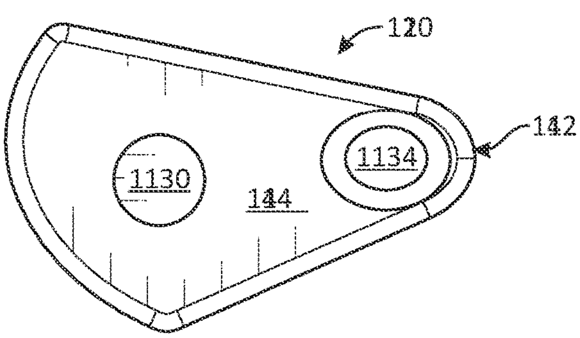
Figure 12D:
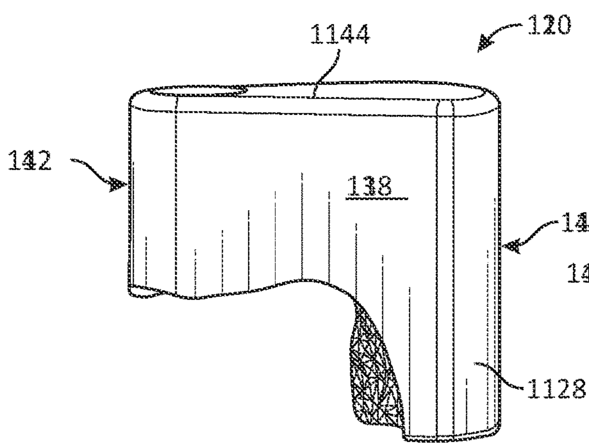
Figure 12E:
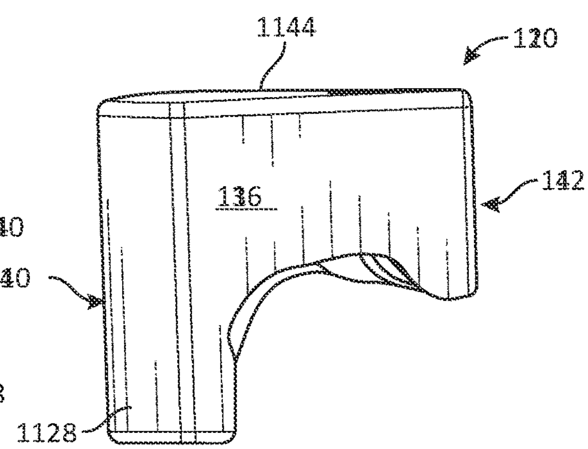

FIG. 12A is an inferior side perspective view. FIG. 12B is an inferior side view. FIG. 12C is a superior side view. FIG. 12D is a posterior side view. FIG. 12E is an anterior side view.

Referring now to FIGS. 12A and 12B, in certain embodiments, a tendon trajectory guide 1120 may include a bone engagement surface 1126 separate and independent of whether or not the tendon trajectory guide 1120 includes a bone engagement feature 1128. Alternatively, or in addition, a bone engagement surface 1126 can be include as part of, or together with, a bone engagement feature 1128.

In the illustrated embodiment, the tendon trajectory guide 1120 can include a bone engagement surface 1126 on at least part of the inferior side 1146 of the body 1134 of the tendon trajectory guide 1120. In one embodiment, the bone engagement surface 1126 can be defined at least in part based on a bone model of a bone that the inferior side 1146 will face and/or contact during use. In certain embodiments, this means that the bone engagement surface 1126 can include a mirror image of the surface of the bone of the patient in this area of the bone. Alternatively, or in addition, a tendon trajectory guide 1120 can be formed with an inferior side 1146 that lacks a bone engagement surface 1126 and instead can include a concave shape on the inferior side 1146 to accommodate a surface of a bone that the inferior side 1146 will face and/or contact during use.

Figure 13:
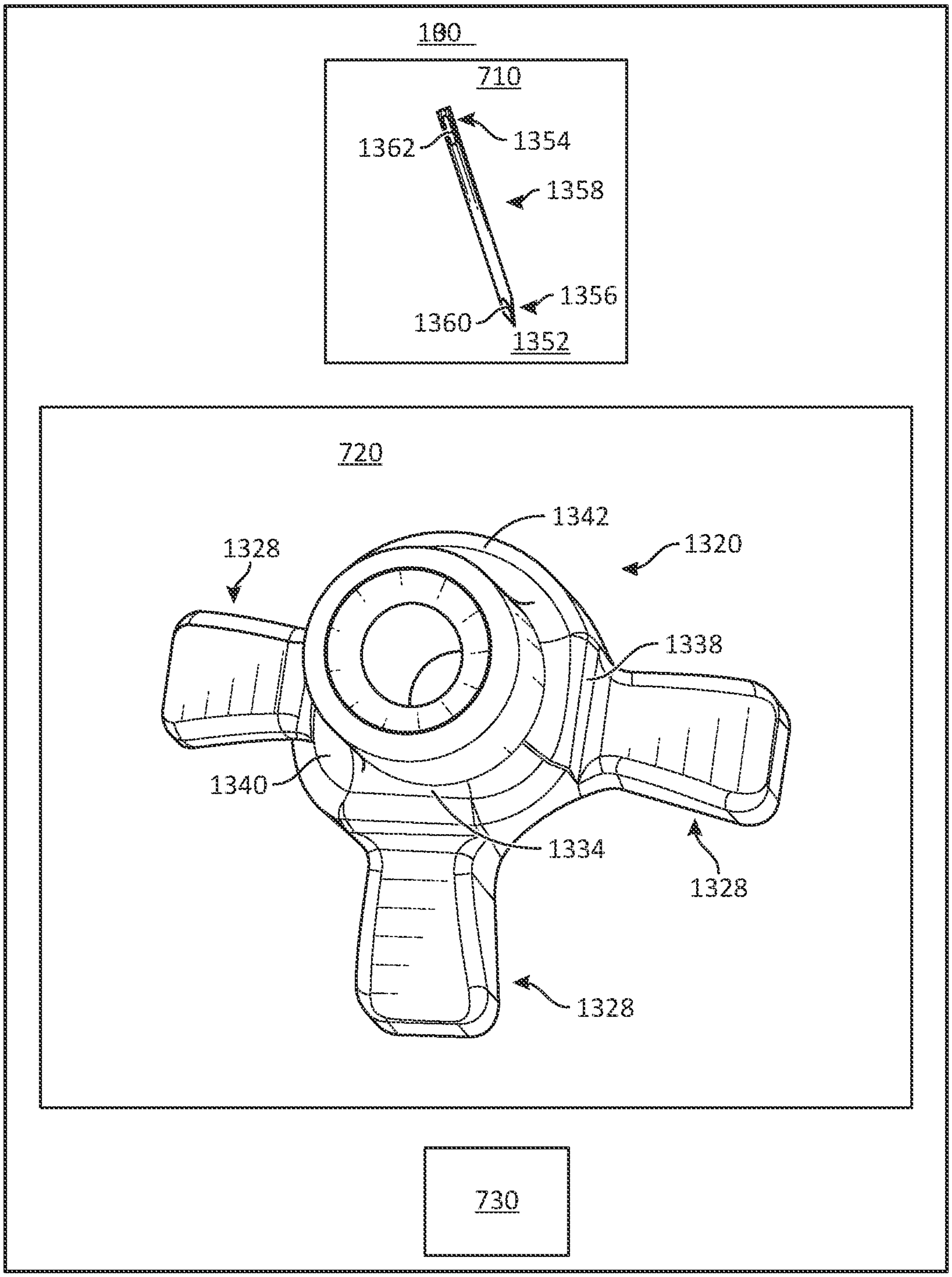
FIG. 13 illustrates an exemplary soft tissue rearrangement system, according to one embodiment.

FIG. 13 illustrates an exemplary soft tissue rearrangement system 1300, according to one embodiment. The soft tissue rearrangement system 1300 can include one or more fasteners 710 embodied in for the form of depicted exemplary fastener 710, one or more STRGs 720 embodied in for the form of depicted exemplary tendon trajectory guide 1320, and zero or one or more complementary components 730. The tendon trajectory guide 1320 may also include one or more trajectory ports 722, one or more optional landmark registration features 724, and/or one or more optional bone engagement features 726. (See FIG. 7) In certain embodiments, a bone engagement feature 1328 can include one or more bone engagement surfaces.

While specific embodiments of complementary components 730 are not specifically shown here in relation to the system 1300, those of skill in the art will appreciate that complementary components 730 can be similar in feature, design, implementation, configuration, and purpose as those described in relation to the system 700 and can be used for the soft tissue rearrangement system 1300. Thus, the soft tissue rearrangement system 1300 can include one or more alignment guides 732, rotation guides 734, reduction guides 736, compression guides 738, positioning guides 740, fixation guides 742, navigation guides 744, implants 746, or the like.

Figure 14A:
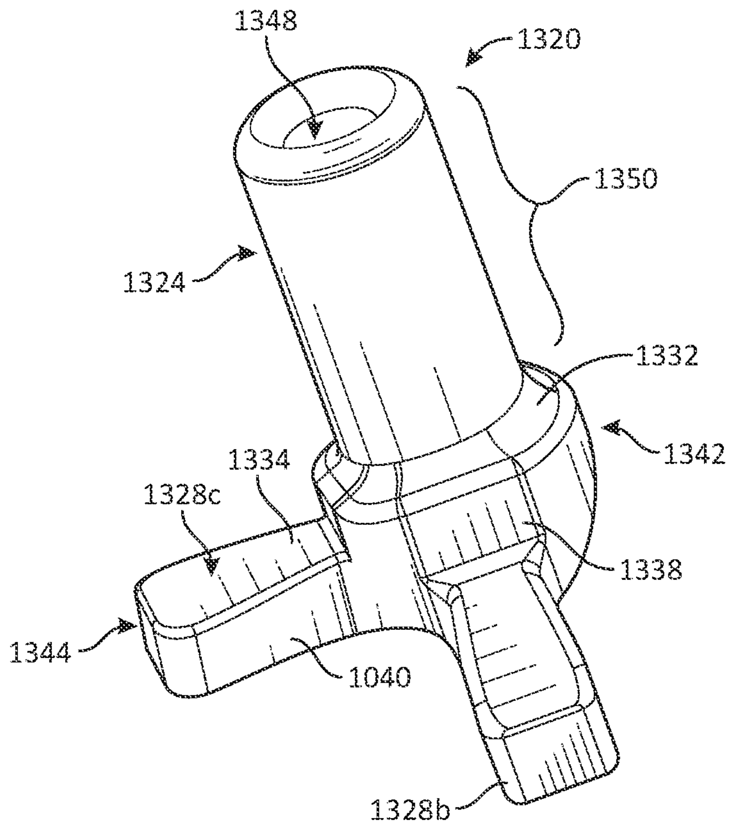
FIGS. 14A-14B illustrate views of a tendon trajectory guide of the system of FIG. 13, according to one embodiment.
Figure 14B:
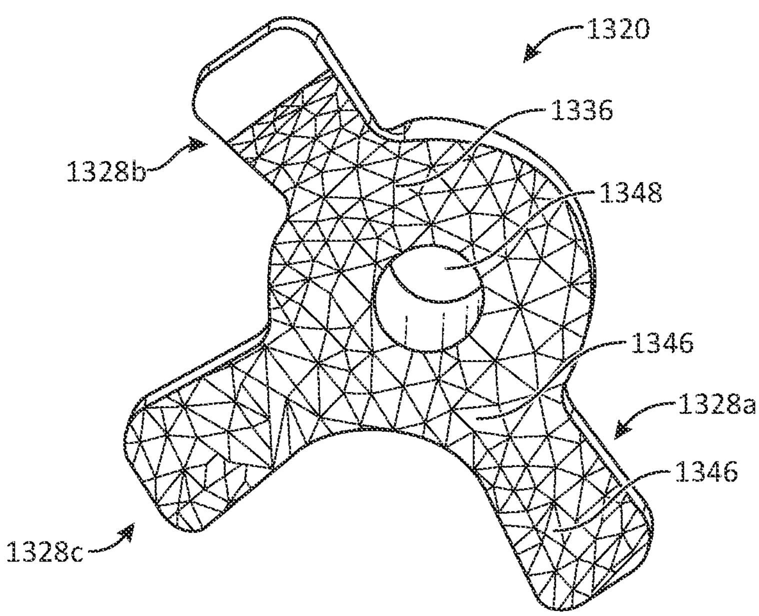

Referring to FIGS. 13, 14A, and 14B, the tendon trajectory guide 1320 may be a custom patient-specific soft tissue rearrangement guide made for a particular patient and/or for a particular surgical procedure. Various aspects of the tendon trajectory guide 1320 may be patient-specific, including, but not limited to, an angle and/or orientation for a trajectory port 1324 of the tendon trajectory guide 1320, a position of the trajectory port 1324, a depth of the trajectory port 1324, a size and/or geometric configuration of the trajectory port 1324, a size of the tendon trajectory guide 1320, a configuration, design, and/or composition of a bone contacting structure such as a bone engagement feature 1328 (e.g., 1328*a*, 1328*b*, 1328*c*) of the tendon trajectory guide 1320, a number of bone engagement features 1328, a position of the tendon trajectory guide 1320 relative to one or more bones of a patient, a position, orientation, configuration and/or existence of an optional handle, and the like.

In one embodiment, the tendon trajectory guide 1320 includes a body 1332 that includes a superior side 1334, an inferior side 1336, a medial side 1338, a lateral side 1340, a posterior side 1342, and an anterior side 1344. Generally, the sides of the tendon trajectory guide 1320 refer to the direction the sides face when the tendon trajectory guide 1320 is in use.

In certain embodiments, a position, configuration, and/or orientation of the trajectory port 1324 can be determined and/or defined at least partially based on a bone model of at least a portion of a bone of a patient's foot. The trajectory port 1324 extends through the body 1332. In one embodiment, the trajectory port 1324 may be positioned to guide a tool for forming a bone tunnel in a bone of a patient for a surgical procedure such as a deformity correction. The bone model may be defined and/or determined based at least in part on medical imaging of the bone of the patient.

In one embodiment, the position and/or configuration of the trajectory port 1324 may be determined, defined, and/or dictated at least in part by both a bone model of a portion of a patient's foot and user instructions 604. Advantageously, the user instructions 604 may identify certain goals for the tendon trajectory guide 1320 such as minimal size (i.e., width, length, depth), shape, contour, position, orientation, trajectory, and the like. Since the tendon trajectory guide 1320 guides the formation of bone tunnel, the configuration of the tendon trajectory guide 1320 provided by the user instructions 604 can also define an osteotomy or bone tunnel created using the tendon trajectory guide 1320.

In certain embodiments, a user, or end user, may review the bone model, and a model of the tendon trajectory guide 1320 and based on these models determine, at least in part, where to position and/or orient a trajectory port 1324 within a tendon trajectory guide 1320. Advantageously, determining a position and/or orientation for the trajectory port 1324 in a model of an instrument can be directly reflected in a fabricated instrument based on the model. In one embodiment, the position and/or orientation for the trajectory port 1324 can be based on user instructions 604. Alternatively, or in addition, other features of a trajectory port 1324 can be based, at least partially, on user instructions 604. Alternatively, or in addition, in one embodiment, features of a tendon trajectory guide 1320 can be based on accepted practice aspects for a particular surgical procedure.

FIGS. 14A and 14B illustrate views of a tendon trajectory guide 1320 of the system of FIG. 13, according to one embodiment. The tendon trajectory guide 1320 includes at least one trajectory port 1324.

In the illustrated embodiment, the tendon trajectory guide 1320 includes three bone engagement features 1328*a*, 1328*b*, 1328*c*. Other embodiments may not include a bone engagement feature 1328. In certain embodiments, one or more of the bone engagement features 1328 may include a bone engagement surface 1346. Alternatively, or in addition, the tendon trajectory guide 1320 may include a bone engagement surface 1346. Alternatively, or in addition, the tendon trajectory guide 1320 may also include one or more bone attachment features (not shown).

In certain embodiments, the tendon trajectory guide 1320 includes a bone engagement surface 1346 on an inferior side 1336 of the body 1332. The bone engagement surface 1346 is configured to engage a surface of a foot bone such that the bone engagement surface 1346 positions the tendon trajectory guide 1320 at a desired position on the foot bone. The desired position can be determined, predetermined, and/or prescribed by a surgeon.

The trajectory port 1324 extends through the body 1332. In one embodiment, the trajectory port 1324 includes an opening 1348 that extends from a top surface of the trajectory port 1324 through to a bottom surface of the trajectory port 1324. The trajectory port 1324 serves to guide a surgeon and indicates a desired trajectory for a temporary fastener, a cutting tool, or other instrumentation a surgeon may use for deploying a tendon, tendon substitute, tendon anchor, soft tissue, a graft, or the like. In one embodiment, the trajectory port 1324 is configured to guide a tool for forming a bone tunnel in a foot bone of a patient. The trajectory port 1324 can be defined at least partially based on a bone model of at least a portion of the foot bone. The bone model may be based on medical imaging of the foot bone of the patient.

In the illustrated embodiment, of FIGS. 14A and 14B, the trajectory port 1324 includes a port body 1350. The port body 1350 extends away from the body 1332. In certain embodiments, the port body 1350 has a length that enables a user to grasp the port body 1350 to secure the tendon trajectory guide 1320 in place for formation of a bone tunnel by way of the trajectory port 1324. In such an embodiment, the tendon trajectory guide 1320 may not include a separate handle that is connectable to a internally threaded opening in the tendon trajectory guide 1320.

Referring to FIGS. 13, 14A, and 14B, the soft tissue rearrangement system 1300 can serve to guide formation of a bone tunnel or passage for a variety of procedures. In one embodiment, the soft tissue rearrangement system 1300 may be configured specifically as a tendon transfer system for tendon deployment to remediate a bone condition present in a patient's foot. The soft tissue rearrangement system 1300 includes a fastener 710.

In one embodiment, the fastener 710 can serve as a guide for forming a bone tunnel or passage in bone and as an inserter 1352. The inserter 1352 includes a proximal end 1354, a distal end 1356, and an elongated body 1358 between the proximal end 1354 the distal end 1356. The distal end 1356 includes a point 1360 and the proximal end 1354 includes an opening 1362.

A user may position the tendon trajectory guide 1320 in a desired location on a bone for formation of bone tunnel. The bone tunnel can cooperate with an anchor to anchor soft tissue within the bone tunnel. The user may deploy the inserter 1352 to serve as a guide for a cannulated drill bit to form the bone tunnel. Once the bone tunnel is formed having two open ends, the user can use the inserter 1352 to insert a tendon, a free end of a tendon, a graft, or the like through the bone tunnel. In one example, a user may pass an end of a tendon and/or graft through the opening 1362 and may secure the tendon and/or graft to the inserter 1352. Next, a user may thread the inserter 1352 through the bone tunnel. The user may then tension the tendon and/or graft to desired tension and anchor the tendon and/or graft to the tunnel.

In the illustrated embodiment, the soft tissue rearrangement system 1300 includes a tendon trajectory guide 1320 configured to permit a user to grasp the port body 1350 to hold the tendon trajectory guide 1320 in place as the bone tunnel is formed and/or as an inserter 1352 or fastener 710 is deployed to facilitate forming the bone tunnel. This embodiment is illustrated in FIG. 13.

Those of skill in the art will appreciate that in certain embodiments, the tendon trajectory guide 1320 can include an integrated handle such as a port body 1350. Or the soft tissue rearrangement system 1300 can include a handle for the tendon trajectory guide 1320. The handle 922 of system 1000 is one example of a handle that can be used with such an embodiment. FIG. 15B illustrates another example. The handle can include a first coupler configured to removably engage a second coupler of the tendon trajectory guide 1320. For example, the first coupler can be external threads on an end of the handle and the second coupler can be internal threads in an opening in a body 1332 of the tendon trajectory guide 1320.

Figure 15A:
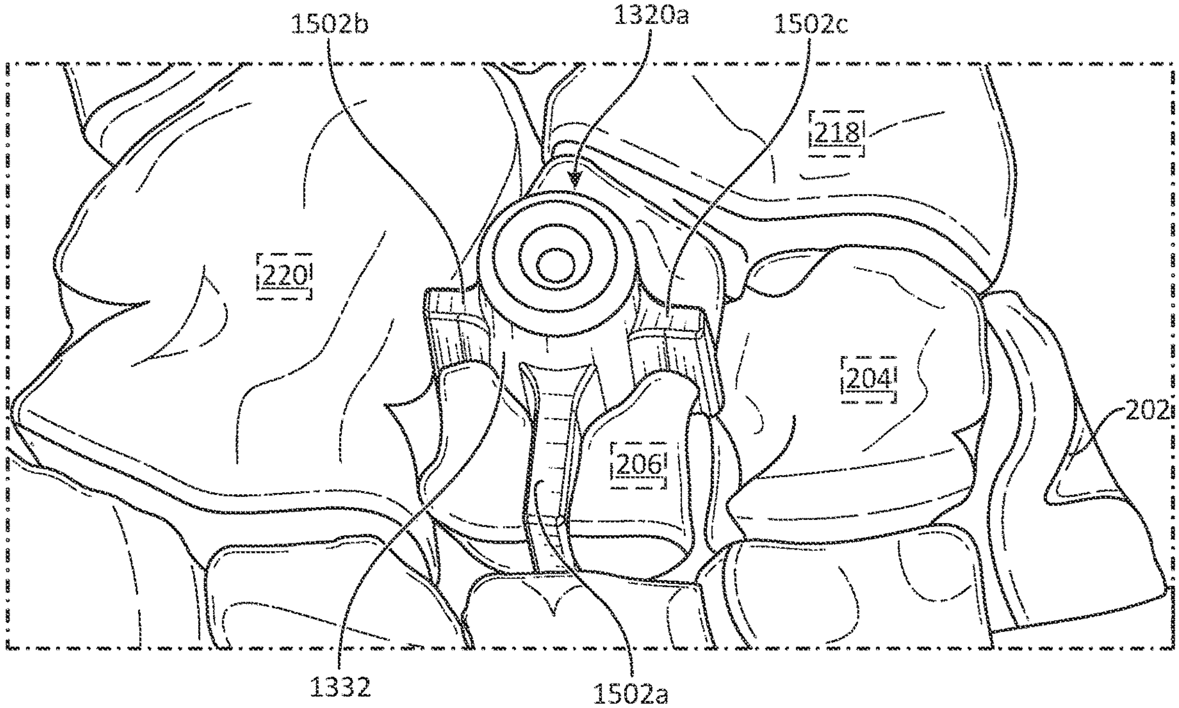
FIGS. 15A-15B illustrate dorsal perspective views of a foot including a tendon trajectory guide, according to an alternative embodiment.
Figure 15B:
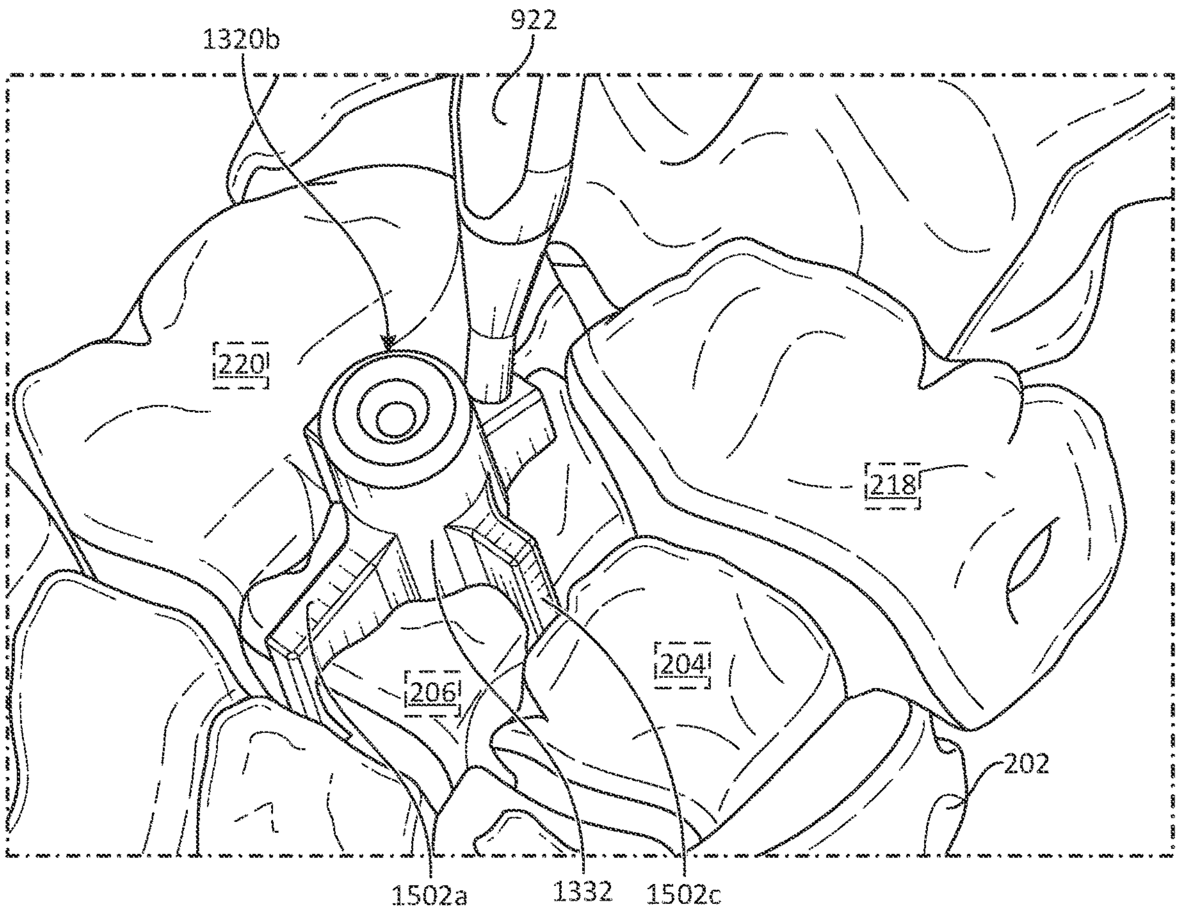
Figure 16A:
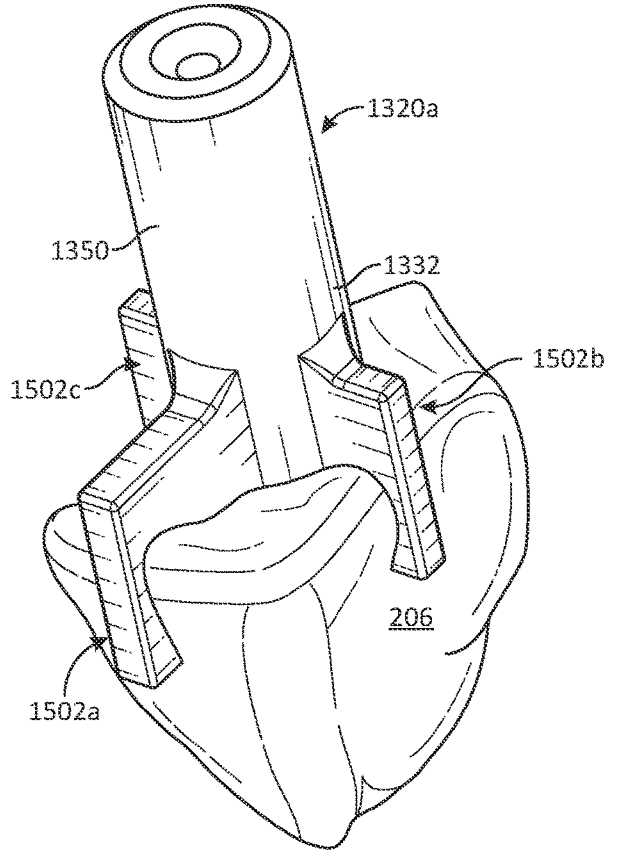
FIGS. 16A-16C illustrate views of a tendon trajectory guide of FIG. 15A, according to one embodiment.
Figure 16B:
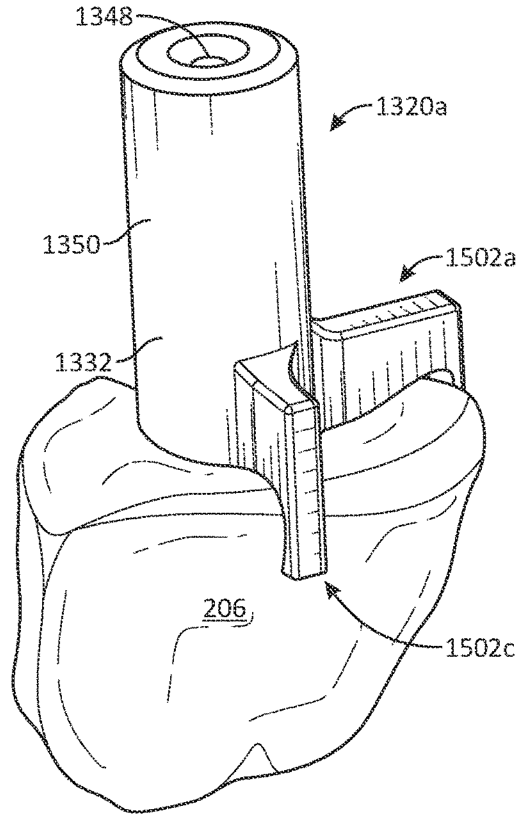
Figure 16C:
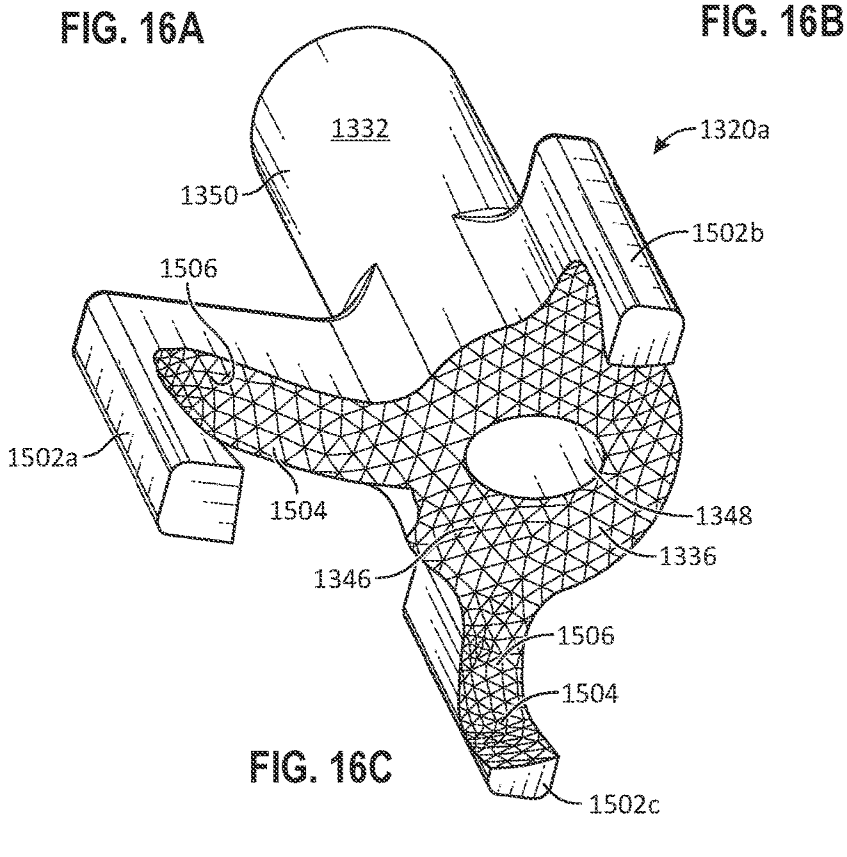

FIGS. 15A-15B illustrate dorsal perspective views of a foot including a tendon trajectory guide, according to an alternative embodiment. FIG. 15A illustrates one embodiment of a tendon trajectory guide 1320 in which the port body 1350 serves as a handle for using the tendon trajectory guide 1320. FIG. 15B illustrates an alternative embodiment in which the body 1332 of the tendon trajectory guide 1320 includes a coupler for coupling to a coupler of a separate handle 922. The embodiments of FIGS. 15A and 15B may have many structures, features, and functions, operations, and configuration similar or identical to those of the soft tissue rearrangement system 1300 described in relation to FIG. 13, like parts are identified with the same reference numerals. The embodiment of the tendon trajectory guide 1320 of FIG. 15A is illustrated in FIGS. 16A-16C.

FIGS. 15A-15B a lateral cuneiform 206 as the desired location for securing a tendon for a particular tendon transfer procedure. For example, a surgeon may desire to perform a posterior tibial tendon transfer surgical procedure. Advantageously, the tendon trajectory guide 1320 of FIGS. 15A and 15B provide examples of patient-specific tendon transfer guides suitable, and/or specifically designed, to assist a surgeon in performing this procedure.

In the illustrated embodiment, the tendon trajectory guides 1320 include a plurality of appendages 1502. The plurality of appendages 1502 may extend laterally from the body 1332. Advantageously, a surgeon can determine and/or provide instructions for how many appendages 1502 to include and/or what landmarks one or more appendages 1502 are to register to during the surgical procedure.

In one embodiment, the appendage 1502 can be an implementation of a bone engagement features 1328. Alternatively, or in addition, an appendage 1502 may include more or fewer aspects as a bone engagement feature 1328. In the embodiment of FIG. 15B, the tendon trajectory guide 1320*b* can include a structure that extends for engaging with the handle 922. This structure may be a bone engagement feature 1328, a landmark registration feature, an appendage, any combination of these, and/or neither of these.

FIGS. 16A-16C illustrate views of a tendon trajectory guide of FIG. 15A, according to one embodiment. FIG. 16A is an anterior-medial view of the lateral cuneiform 206 with a tendon trajectory guide 1320*a* positioned on its dorsal surface. It should be noted that the appendages 1502, in this embodiment, are configured to wrap around a medial, anterior, and lateral end of the lateral cuneiform 206 and extend into three of the joints of the lateral cuneiform 206. By including three appendages 1502, a surgeon can be assured that the tendon trajectory guide 1320*a* is positioned in a desired position determined preoperatively. In one embodiment, a surgeon determines the desired position. FIG. 16B is a posterior-lateral view of the lateral cuneiform 206 with the tendon trajectory guide 1320*a* positioned on its dorsal surface.

FIG. 16C illustrates an inferior side 1336 of the tendon trajectory guide 1320*a*. The bone engagement surface 1346 is illustrated. In certain embodiments, each appendage 1502 can include an appendage inferior surface 1504. In the illustrated embodiment, the appendage inferior surface 1504 includes a bone engagement surface 1506 on the appendage inferior surface 1504. In certain embodiments, the appendage inferior surface 1504 can be implementations of a landmark registration feature and/or a bone engagement feature.

In the illustrated embodiment, at least one appendage 1502 extends from the body 1332. Advantageously, the appendage 1502 can provide a surgeon with confidence and assurance in the placement and positioning of the tendon trajectory guide 1320 on the bone because the appendage 1502 can be configured to engage with a particular landmark on the bone (e.g., a side surface of the bone (dorsal, plantar, medial, lateral, a projection or a depression or cavity, one or more joints, or the like). Alternatively, or in addition, the appendage 1502 can include a contoured bone engagement surface 1506 that can further facilitate registration of the appendage 1502 and/or tendon trajectory guide 1320 with the bone. In this manner, a surgeon can be assured intraoperatively that the tendon trajectory guide 1320 is being positioned as desired.

In certain embodiments, the appendage 1502 can be shaped like a hook to engage a surface or structure of a bone. Alternatively, or in addition, the tendon trajectory guide 1320 may include an appendage 1502 on each side, together the appendage 1502 can engage one or more landmarks of the bone such that the surgeon can accurately position and register the tendon trajectory guide 1320 to the bone.

Figure 17:
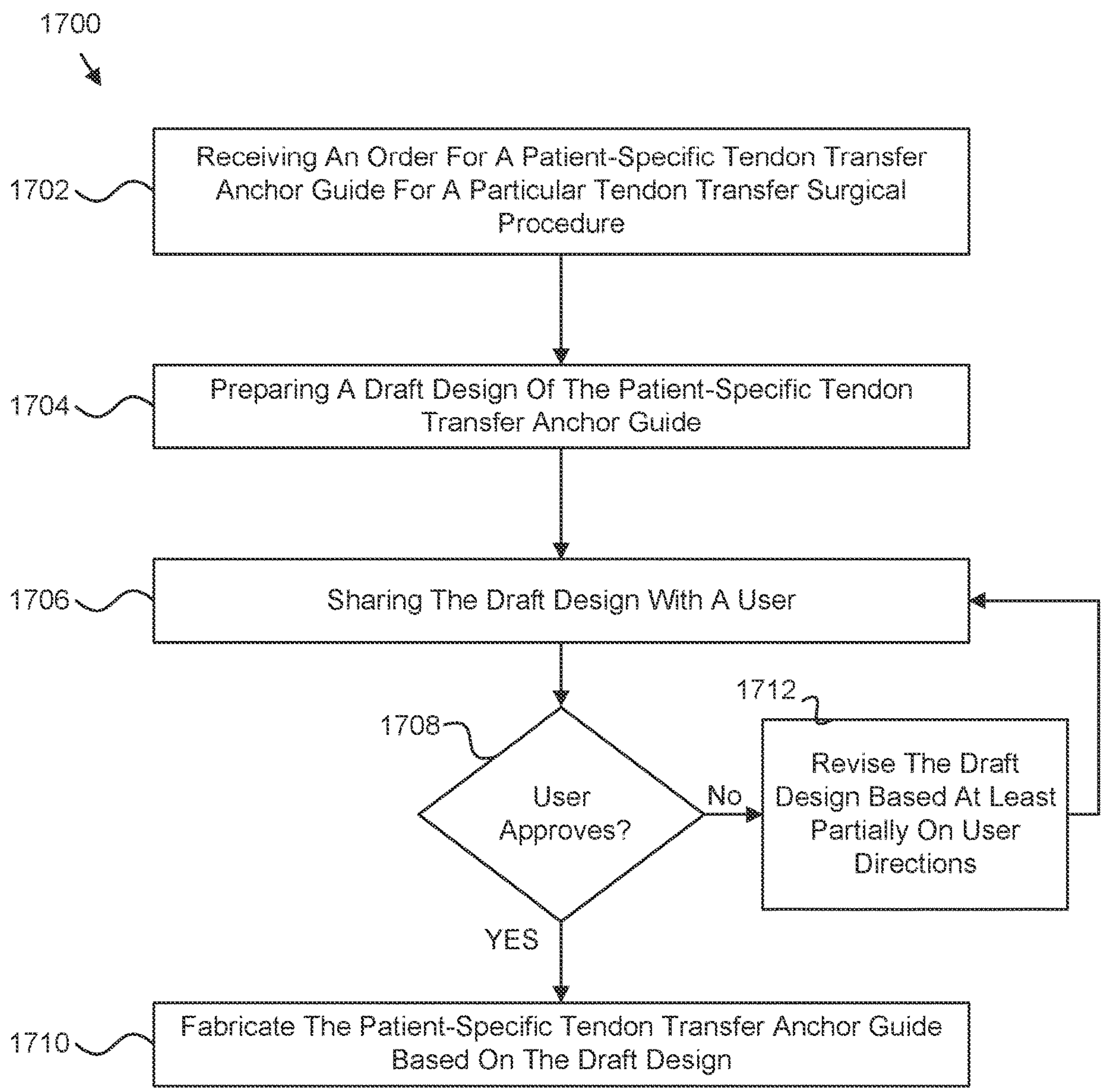
FIG. 17 is a flowchart diagram depicting a method for generating a tendon trajectory guide, according to one embodiment.

FIG. 17 is a flowchart diagram of an example process 1700 or method for generating a tendon trajectory guide, according to one embodiment. In some implementations, one or more process blocks of FIG. 17 may be performed by a patient-specific tendon transfer anchor guide.

As shown in FIG. 17, process 1700 may include receiving (block 1702) an order for a patient-specific tendon transfer anchor guide for a particular soft tissue transfer surgical procedure. The patient-specific tendon transfer anchor guide may include: a body having a superior side, an inferior side, a medial side, a lateral, a posterior side, and an anterior side; a trajectory port that extends through the body, the trajectory port configured to guide a tool for forming a bone tunnel in a foot bone of a patient; a bone engagement surface on the inferior side of the body, the bone engagement surface configured to engage a surface of the foot bone such that the bone engagement surface positions the patient-specific tendon transfer anchor guide at a position on the foot bone that satisfies a desired position for a bone tunnel in the foot bone; an appendage that extends laterally from the body, the appendage having an appendage inferior surface; and where the bone engagement surface extends across at least a portion of the inferior side of the body and at least a portion of the appendage inferior surface.

For example, patient-specific tendon transfer anchor guide may receive an order for a patient-specific tendon transfer anchor guide for a particular soft tissue transfer surgical procedure, as described above.

As also shown in FIG. 17, process 1700 may include preparing (block 1704) a draft design of the patient-specific tendon transfer anchor guide, the draft design defined based at least partially on a bone model of at least a portion of a foot bone of the patient, the bone model based on medical imaging of a patient's foot. For example, a technician may prepare a draft design of the patient-specific tendon transfer anchor guide, as described above.

As further shown in FIG. 17, process 1700 may include sharing (block 1706) the draft design with a user of the patient-specific tendon transfer anchor guide. For example, a technician may share the draft design with a user (e.g., a surgeon). In one embodiment, the technician may schedule a meeting or may send an email or file with the draft design.

Next, the process 1700 may include a determination (block 1708) in which the surgeon (e.g., a user) determines whether or not the surgeon approves of the draft design. If so, the process 1700 may continue with fabricating (block 1710) the patient-specific tendon transfer anchor guide based on the draft design after approval of the draft design by the user. If the surgeon does not approve (block 1708), the process may continue with revising (block 1712) the draft design based at least partially on user directions.

In one embodiment, a technician may revise (block 1712) the draft design. Alternatively, or in addition, a user (e.g., surgeon) may revise the draft design. Alternatively, or in addition, the surgeon may simply provide instructions on what to change and a technician may make those changes. At this point, the process 1700 returns back to block 1706 in which a technician may share (block 1706) a revised version of the draft design with the user. The cycle of sharing 1706, determination 1708, and revising 1712, may continue for multiple iterations until the surgeon is satisfied that the draft design will serve its purpose.

In one embodiment, process 1700 may include additional implementations, such as any single implementation or any combination of implementations described below and/or in connection with one or more other processes described elsewhere herein. A first implementation, alone or in combination with the first implementation, revising further may include adding a second appendage extending from the patient-specific tendon transfer anchor guide, the second appendage having an appendage inferior surface that may include at least a portion of the bone engagement surface.

Although FIG. 17 shows example blocks of process 1700, in some implementations, process 1700 may include additional blocks, fewer blocks, different blocks, or differently arranged blocks than those depicted in FIG. 17. Additionally, or alternatively, two or more of the blocks of process 1700 may be performed in parallel.

Those of skill in the art will appreciate that embodiments of the system disclosed herein can be used on humans and animals and on bones that are relatively small in comparison to other bones of the body (e.g., bones of the foot and hand). Advantageously, the embodiments of the system seek to minimize the number of fasteners or pins placed within the bones of a patient by planning a surgical procedure such that pins or fasteners placed in one stage are and/or can be reused in subsequent stages. Consequently, pins initially deployed can remain in the bone or bone fragment as instruments are deployed and/or subsequent stages of the surgical procedure are performed.

Advantageously, because the present disclosure uses a bone model of the patient's bones the sizes, dimensions, lengths and configurations of the components of the example systems can each be changed, adapted, revised, and/or customized to meet the needs and/or preferences of the patient and/or surgeon. Advantageously, using the apparatus, systems, and/or methods of the present disclosure the surgeon may have a preoperative plan that identifies which specific bone screw (length, width, diameter, thread, pitch, etc.) to use for the fasteners.

Advantageously, the present disclosure provides an apparatus, system, and/or method that can remediate a condition in a patient's foot. Those of skill in the art will appreciate that the methods, processes, apparatuses, systems, devices, and/or instruments of the present disclosure can be used to address a variety of conditions in a variety of procedures and/or parts of the body of the patient.

Conventionally, correction methods, systems, and/or instrumentation for a condition such as, for example, a bunion and/or a hallux valgus, face several challenges. One example is how to cut the bone such that the cut faces have a desired angle in relation to each other. Advantageously, the present disclosure can address many, if not all, of these challenges to assist a surgeon in performing the surgical procedure and improve the quality of patient care and outcomes.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles set forth herein.

While specific embodiments and applications of the present disclosure have been illustrated and described, it is to be understood that the scope of this disclosure is not limited to the precise configuration and components disclosed herein. Various modifications, changes, and variations which will be apparent to those skilled in the art may be made in the arrangement, operation, and details of the methods and systems of the present disclosure set forth herein without departing from it spirit and scope.

The invention claimed is:

1. A bone tunnel guide for forming a bone tunnel in bone of a patient for a soft tissue transfer procedure, the bone tunnel guide comprising:

a body having a superior side, an inferior side, a medial side, a lateral side, a posterior side, and an anterior side;

a trajectory port that extends through the body, the trajectory port configured to guide a tool for forming the bone tunnel in a bone of a patient, the bone tunnel configured to receive soft tissue during the soft tissue transfer procedure, the trajectory port defined at least partially based on a bone model of at least a portion of the bone, the bone model based on medical imaging of the bone of the patient; and a bone engagement feature that extends from the body, the bone engagement feature configured to engage at least a portion of the bone such that the bone engagement feature positions the bone tunnel guide in a position that corresponds to a modeled position of a bone tunnel guide model engaging a bone model.

2. The bone tunnel guide of claim 1, wherein at least one aspect of the bone tunnel guide is configured based at least partially on user instructions provided before the bone tunnel guide is fabricated.

3. The bone tunnel guide of claim 1, wherein the bone engagement feature comprises at least one patient-specific aspect unique to the patient.

4. The bone tunnel guide of claim 3, wherein the at least one patient-specific aspect comprises a bone engagement surface on a bone-facing surface of the bone engagement feature, the bone engagement surface configured to engage at least one landmark of the bone.

5. The bone tunnel guide of claim 4, wherein the bone engagement surface corresponds to a surface of the bone such that the bone tunnel guide provides haptic feedback to a user when the bone tunnel guide translates to the position corresponding to the modeled position of the bone tunnel guide model engaging the bone model.

6. The bone tunnel guide of claim 1, further comprising a plurality of bone engagement features, each extending away from the trajectory port.

7. The bone tunnel guide of claim 6, wherein a number of bone engagement features of the plurality of bone engagement features is directly proportional to a number of landmark configurations near, or at, the modeled position of the bone tunnel guide model engaging the bone model.

8. The bone tunnel guide of claim 6, wherein a number of bone engagement features of the plurality of bone engagement features is determined at least partially by user directions.

9. The bone tunnel guide of claim 1, further comprising:

a handle configured to secure the bone tunnel guide in place for formation of a bone tunnel by way of the trajectory port.

10. The bone tunnel guide of claim 9, wherein the handle comprises a shaft having a proximal end and a distal end, the distal end comprising a coupler comprising external threads configured to engage internal threads formed in the body.

11. The bone tunnel guide of claim 1, wherein the trajectory port comprises a port body that extends away from the body, the port body having a length that enables a user to grasp the port body to secure the bone tunnel guide in place for formation of a bone tunnel by way of the trajectory port.

12. The bone tunnel guide of claim 1, further comprising a bone engagement surface on at least part of the inferior side of the body, the bone engagement surface defined at least partially based on the bone model.

13. The bone tunnel guide of claim 1, further comprising a landmark registration feature configured to engage a landmark of the bone.

14. The bone tunnel guide of claim 1, wherein a configuration of the bone engagement feature is directly proportional to a landmark configuration of the bone indicated on the bone model.

15. The bone tunnel guide of claim 1, wherein the bone tunnel guide is fabricated from one of a polymer and metal.

16. A tendon transfer system for tendon deployment to remediate a bone condition present in a patient's foot, comprising:

a tendon trajectory guide comprising:

a body having a superior side, an inferior side, a medial side, a lateral side, a posterior side, and an anterior side;

a trajectory port that extends through the body, the trajectory port configured to guide a tool for forming a bone tunnel in a foot bone of a patient, the trajectory port defined at least partially on a bone model of at least a portion of the foot bone, the bone model based on medical imaging of the foot bone of the patient; and a bone engagement surface on the inferior side of the body, the bone engagement surface configured to engage a surface of the foot bone such that the bone engagement surface positions the tendon trajectory guide at a desired position on the foot bone;

an inserter having:

a proximal end;

a distal end;

an elongated body between the proximal end and the distal end; and wherein the distal end comprises a point and the proximal end comprises an opening; and a handle comprising a first coupler configured to removably engage with a second coupler connected to the tendon trajectory guide.

17. The tendon transfer system of claim 16, further comprising a plurality of appendages that extend laterally from the body, each appendage having an appendage inferior surface and comprising a bone engagement surface on the appendage inferior surface.

18. A bone tunnel guide for forming a bone tunnel in a bone of a patient for a soft tissue transfer procedure, the bone tunnel guide comprising:

a body having a superior side, an inferior side, a medial side, a lateral side, a posterior side, and an anterior side;

a trajectory port that extends through the body, the trajectory port configured to guide a tool for forming a bone tunnel in a bone of a patient, the bone tunnel configured to receive soft tissue during the soft tissue transfer procedure, the trajectory port defined at least partially based on a bone model of at least a portion of the bone, the bone model based on medical imaging of the bone of the patient; and a plurality of bone engagement features that extend from the body, the plurality of bone engagement features configured to engage at least a portion of the bone and wherein a number of bone engagement features is defined at least in part by user instructions.

19. The bone tunnel guide of claim 18, wherein the bone tunnel guide comprises at least one patient-specific aspect unique to the patient.

20. The bone tunnel guide of claim 19, wherein the patient-specific aspect comprises at least one bone engagement surface on a bone-facing surface of at least one of the plurality of bone engagement features, the at least one bone engagement surface configured to engage at least one landmark of the bone of the patient.

* * * * *